US008574578B2

(12) United States Patent
Loizos et al.

(10) Patent No.: US 8,574,578 B2
(45) Date of Patent: Nov. 5, 2013

(54) ANTIBODIES AGAINST PDGFRα TO INHIBIT TUMOR GROWTH

(75) Inventors: Nick Loizos, Staten Island, NY (US); Jim Huber, Scotch Plains, NJ (US)

(73) Assignee: ImClone LLC, New York, NY (US)

( * ) Notice: Subject to any disclaimer, the term of this patent is extended or adjusted under 35 U.S.C. 154(b) by 0 days.

(21) Appl. No.: 13/276,353

(22) Filed: Oct. 19, 2011

(65) Prior Publication Data
US 2012/0027767 A1 Feb. 2, 2012

Related U.S. Application Data

(62) Division of application No. 11/917,890, filed as application No. PCT/US2006/023856 on Jun. 19, 2006, now Pat. No. 8,128,929.

(51) Int. Cl.
*A61K 39/395* (2006.01)

(52) U.S. Cl.
USPC .......................................................... 424/139.1

(58) Field of Classification Search
USPC .......................................................... 424/139.1
See application file for complete search history.

(56) References Cited

U.S. PATENT DOCUMENTS

| | | | |
|---|---|---|---|
| 4,774,321 A | 9/1988 | Rosner et al. |
| 5,200,509 A | 4/1993 | Spencer et al. |
| 5,262,308 A | 11/1993 | Baserga |
| 5,468,468 A | 11/1995 | LaRochelle |
| 5,597,563 A | 1/1997 | Beschorner |
| 5,620,687 A | 4/1997 | Hart |
| 5,624,805 A | 4/1997 | Spencer et al. |
| 5,670,341 A | 9/1997 | Spencer et al. |
| 5,681,818 A | 10/1997 | Spencer et al. |
| 5,686,572 A | 11/1997 | Wolf |
| 5,688,505 A | 11/1997 | Webb et al. |
| 5,705,157 A | 1/1998 | Greene |
| 5,798,266 A | 8/1998 | Quay et al. |
| 5,833,986 A | 11/1998 | LaRochelle |
| 5,852,174 A | 12/1998 | Vlassara et al. |
| 5,863,739 A | 1/1999 | LaRochelle |
| 5,869,337 A | 2/1999 | Crabtree et al. |
| 5,872,218 A | 2/1999 | Wolf |
| 5,872,220 A | 2/1999 | Kiefer et al. |
| 5,891,652 A | 4/1999 | Wolf |
| 5,891,722 A | 4/1999 | Fuks et al. |
| 5,939,269 A | 8/1999 | Goldfine et al. |
| 5,942,412 A | 8/1999 | Prager et al. |
| 5,965,359 A | 10/1999 | Matsui |
| 5,968,508 A | 10/1999 | Golffine |
| 5,968,758 A | 10/1999 | Fuks et al. |
| 5,976,534 A | 11/1999 | Hart |
| 5,977,307 A | 11/1999 | Friden et al. |
| 5,993,818 A | 11/1999 | Torchilin et al. |
| 6,071,891 A | 6/2000 | Low et al. |
| 6,084,085 A | 7/2000 | Baserga et al. |
| 6,090,383 A | 7/2000 | Dasch et al. |
| 6,228,600 B1 | 5/2001 | Matsui |
| 6,316,462 B1 | 11/2001 | Bishop et al. |
| 6,368,826 B1 | 4/2002 | Ligensa et al. |
| 6,660,488 B2 | 12/2003 | Matsui |
| 6,875,741 B2 | 4/2005 | Pillutla et al. |
| 7,037,498 B2 | 5/2006 | Cohen et al. |
| 7,071,160 B2 | 7/2006 | Yamano et al. |
| 7,071,300 B2 | 7/2006 | Deshayes et al. |
| 7,217,796 B2 | 5/2007 | Wang et al. |
| 7,241,444 B2 | 7/2007 | Goetsch et al. |
| 7,252,929 B2 | 8/2007 | Matsui |
| 7,300,655 B2 | 11/2007 | Hansen et al. |
| 7,329,745 B2 | 2/2008 | Fujita-Yamaguchi |
| 7,371,378 B2 | 5/2008 | Cohen et al. |
| 7,427,671 B1 | 9/2008 | Matsui |
| 7,432,244 B2 | 10/2008 | Deshayes et al. |
| 2003/0021780 A1 | 1/2003 | Smith et al. |
| 2003/0165502 A1 | 9/2003 | Fujita-Yamaguchi |
| 2003/0235582 A1 | 12/2003 | Singh et al. |
| 2004/0057950 A1 | 3/2004 | Waksal et al. |
| 2004/0102360 A1 | 5/2004 | Barnett et al. |
| 2004/0116330 A1 | 6/2004 | Naito et al. |
| 2004/0141958 A1 | 7/2004 | Steinaa et al. |
| 2004/0202651 A1 | 10/2004 | Cohen et al. |
| 2004/0202655 A1 | 10/2004 | Morton et al. |
| 2004/0228859 A1 | 11/2004 | Graus et al. |
| 2004/0265307 A1 | 12/2004 | Singh et al. |
| 2005/0008642 A1 | 1/2005 | Graus et al. |
| 2005/0079184 A1 | 4/2005 | Hsing-Chang et al. |
| 2005/0084906 A1 | 4/2005 | Goetsch et al. |
| 2005/0136063 A1 | 6/2005 | Wang et al. |

(Continued)

FOREIGN PATENT DOCUMENTS

| | | |
|---|---|---|
| EP | 0294021 | 12/1988 |
| EP | 0369943 | 5/1990 |

(Continued)

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Dolloff, et al., Bone-metastatic potential of human prostate cancer cells correlates with Akt/PKB activation by alpha platelet-derived growth factor receptor, Oncogene 24:6848-6854 (2005).

(Continued)

*Primary Examiner* — Lynn Bristol
(74) *Attorney, Agent, or Firm* — Nicole S. Woods

(57) ABSTRACT

The invention provides antibodies that bind to human PDGFRα and neutralize activation of the receptor. The invention further provides methods for neutralizing activation of PDGFRα and methods of treating a mammal with a neoplastic disease using the antibodies alone or in combination with other agents.

3 Claims, 15 Drawing Sheets

(56) References Cited

U.S. PATENT DOCUMENTS

| | | |
|---|---|---|
| 2005/0186203 A1 | 8/2005 | Singh et al. |
| 2005/0244408 A1 | 11/2005 | Cohen et al. |
| 2005/0249728 A1 | 11/2005 | Singh et al. |
| 2005/0249730 A1 | 11/2005 | Goetsch et al. |
| 2005/0281812 A1 | 12/2005 | Cohen et al. |
| 2006/0106203 A1 | 5/2006 | Winter et al. |
| 2006/0134172 A1 | 6/2006 | Shepard et al. |
| 2006/0149033 A1 | 7/2006 | Deshayes et al. |
| 2006/0193772 A1 | 8/2006 | Ochiai et al. |
| 2006/0233814 A1 | 10/2006 | Goldmakher et al. |
| 2007/0009970 A1 | 1/2007 | Heller et al. |
| 2007/0196376 A1 | 8/2007 | Raeber et al. |
| 2012/0034244 A1* | 2/2012 | Loizos et al. ............ 424/174.1 |

FOREIGN PATENT DOCUMENTS

| | | |
|---|---|---|
| EP | 0375438 | 6/1990 |
| EP | 1661582 | 5/2006 |
| WO | 8906692 | 7/1989 |
| WO | 9213867 | 8/1992 |
| WO | 9419016 | 9/1994 |
| WO | 9744352 | 11/1997 |
| WO | 02053596 | 7/2002 |
| WO | 03059951 | 7/2003 |
| WO | 03100008 | 12/2003 |
| WO | 03106621 | 12/2003 |
| WO | 2004071529 | 8/2004 |
| WO | 2004083248 | 9/2004 |
| WO | 2004087756 | 10/2004 |
| WO | 2005005635 | 1/2005 |
| WO | 2005016967 | 2/2005 |
| WO | 2005016970 | 2/2005 |
| WO | 2005052005 | 6/2005 |
| WO | 2005082415 | 9/2005 |
| WO | 2006008639 | 1/2006 |
| WO | 2006013472 | 2/2006 |
| WO | 2006060419 | 6/2006 |
| WO | 2006069202 | 6/2006 |
| WO | 2007000328 | 1/2007 |
| WO | 2007012614 | 2/2007 |
| WO | 2007031875 | 3/2007 |

OTHER PUBLICATIONS

Board, et al., Drug Resistance Updates 8(1-2):75-83 (2005).
Deevi, et al., Proceedings of the American Association for Cancer Research #3729 47:877 (Apr. 5, 2006).
Kim, et al., Cancer Research 64(12):4201-4208 (2004).
Lev, et al., Clinical Cancer Research 11(1):306-314 (2005).
Scotlandi, et al., Cancer Research 58(18):4127-4131 (1998).
Shen, et al., Journal of Biological Chemistry 281(16):10706-10714 (2006).
Uehara, et al., Journal of the National Cancer Institute 95(6):458-470 (2003).
Wu, et al., Clinical Cancer Research 11(8):3065-3074 (2005).
Baroni, et al., N Engl J Med 354(25):2667-2676 (2006).
Burtrum, et al., Cancer Research 63:8912-8921 (2003).
Dolloff, et al., Cancer Res 67(2):555-62 (2007).
Fleming, et al., Cancer Res 52(16):4550-4553 (1992).
George, Adv Exp Med Biol, (New Trends in Cancer for the 21st Century) 532:141-151 (2003), edited by Llombart-Bosch and Felipo, Kluwer Academic/Plenum Publishers.
Heinrich, et al., Science 299(5607):708-10 (2003).
Loizos, et al., Mol Cancer Ther 4(3):369-379 (2005).
Matei, et al., Oncogene 25(14):2060-2069 (2006).
Matsuyama, et al., Cancer Research 63:7791-7798 (2003).
Ostman, et al., Adv Cancer Res 80:1-38 (2001).
Scotlandi, et al., Cancer Research 65(9):3868-3876 (2005).
Shao, et al., Oncogene 19(38):4337-4345 (2000).
Stock, et al., Mol Cancer Ther 6(7):1932-1941 (2007).

* cited by examiner a.

b.

SEQUENCE LISTING

<160> NUMBER OF SEQ ID NOS: 63

<210> SEQ ID NO 1
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 1 agt agt agt tac tac                                         15
Ser Ser Ser Tyr Tyr
1               5

<210> SEQ ID NO 2
<211> LENGTH: 5
<212> TYPE: PRT
<213> ORGANISM: Homo sapiens

<400> SEQUENCE: 2

Ser Ser Ser Tyr Tyr
1               5

<210> SEQ ID NO 3
<211> LENGTH: 48
<212> TYPE: DNA
<213> ORGANISM: Homo sapiens
<220> FEATURE:
<221> NAME/KEY: CDS
<222> LOCATION: (1)..(48)

<400> SEQUENCE: 3 agt ttc ttt tat act ggg agc acc tac tac aac ccg tcc ctc agg agt    48
Ser Phe Phe Tyr Thr Gly Ser Thr Tyr Tyr Asn Pro Ser Leu Arg Ser
1               5                   10                  15

<210> SEQ ID NO 4
<211> LENGTH: 16
<212> TYPE: PRT
<213> ORGANISM: Homo sapiens

<400> SEQUENCE: 4

Ser Phe Phe Tyr Thr Gly Ser Thr Tyr Tyr Asn Pro Ser Leu Arg Ser
1               5                   10                  15

<210> SEQ ID NO 5
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 5 cag tcc acg tat tac tat ggt tcg ggg aat tat tat ggc tgg ttc gac    48
Gln Ser Thr Tyr Tyr Tyr Gly Ser Gly Asn Tyr Tyr Gly Trp Phe Asp
1               5                   10                  15 cgc                                                                51
Arg

<210> SEQ ID NO 6
<211> LENGTH: 17
<212> TYPE: PRT
<213> ORGANISM: Homo sapiens

-continued

```
<400> SEQUENCE: 6

Gln Ser Thr Tyr Tyr Tyr Gly Ser Gly Asn Tyr Tyr Gly Trp Phe Asp
1               5                   10                  15

Arg

<210> SEQ ID NO 7
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 7 cag ctg cag ctg cag gag tcg ggc cca gga ctg gtg aag cct tcg gag      48
Gln Leu Gln Leu Gln Glu Ser Gly Pro Gly Leu Val Lys Pro Ser Glu
1               5                   10                  15 acc ctg tcc ctc acc tgc act gtc tct ggt ggc tcc atc aac agt agt      96
Thr Leu Ser Leu Thr Cys Thr Val Ser Gly Gly Ser Ile Asn Ser Ser
            20                  25                  30 agt tac tac tgg ggc tgg ctc cgc cag tcc cca ggg aag ggg ctg gag     144
Ser Tyr Tyr Trp Gly Trp Leu Arg Gln Ser Pro Gly Lys Gly Leu Glu
        35                  40                  45 tgg att ggg agt ttc ttt tat act ggg agc acc tac tac aac ccg tcc     192
Trp Ile Gly Ser Phe Phe Tyr Thr Gly Ser Thr Tyr Tyr Asn Pro Ser
    50                  55                  60 ctc agg agt cga ctc acc ata tcc gta gac acg tcc aag aac cag ttc     240
Leu Arg Ser Arg Leu Thr Ile Ser Val Asp Thr Ser Lys Asn Gln Phe
65                  70                  75                  80 tcc ctg atg ctg agt tct gtg acc gcc gca gac acg gct gta tat tac     288
Ser Leu Met Leu Ser Ser Val Thr Ala Ala Asp Thr Ala Val Tyr Tyr
                85                  90                  95 tgt gcg aga cag tcc acg tat tac tat ggt tcg ggg aat tat tat ggc     336
Cys Ala Arg Gln Ser Thr Tyr Tyr Tyr Gly Ser Gly Asn Tyr Tyr Gly
            100                 105                 110 tgg ttc gac cgc tgg gac cag gga acc ctg gtc acc gtc tcc tca         381
Trp Phe Asp Arg Trp Asp Gln Gly Thr Leu Val Thr Val Ser Ser
        115                 120                 125

<210> SEQ ID NO 8
<211> LENGTH: 127
<212> TYPE: PRT
<213> ORGANISM: Homo sapiens

<400> SEQUENCE: 8

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Ser
            20                  25                  30

Ser Tyr Tyr Trp Gly Trp Leu Arg Gln Ser Pro Gly Lys Gly Leu Glu
        35                  40                  45

Trp Ile Gly Ser Phe Phe Tyr Thr Gly Ser Thr Tyr Tyr Asn Pro Ser
    50                  55                  60

Leu Arg Ser Arg Leu Thr Ile Ser Val Asp Thr Ser Lys Asn Gln Phe
65                  70                  75                  80

Ser Leu Met Leu Ser Ser Val Thr Ala Ala Asp Thr Ala Val Tyr Tyr
                85                  90                  95

Cys Ala Arg Gln Ser Thr Tyr Tyr Tyr Gly Ser Gly Asn Tyr Tyr Gly
            100                 105                 110
```

Trp Phe Asp Arg Trp Asp Gln Gly Thr Leu Val Thr Val Ser Ser
            115                 120                 125

<210> SEQ ID NO 9
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 9 agg gcc agt cag agt gtt agc agc tac tta gcc                     33
Arg Ala Ser Gln Ser Val Ser Ser Tyr Leu Ala
1               5                   10

<210> SEQ ID NO 10
<211> LENGTH: 11
<212> TYPE: PRT
<213> ORGANISM: Homo sapiens

<400> SEQUENCE: 10

Arg Ala Ser Gln Ser Val Ser Ser Tyr Leu Ala
1               5                   10

<210> SEQ ID NO 11
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 11 gat gca tcc aac agg gcc act                                     21
Asp Ala Ser Asn Arg Ala Thr
1               5

<210> SEQ ID NO 12
<211> LENGTH: 7
<212> TYPE: PRT
<213> ORGANISM: Homo sapiens

<400> SEQUENCE: 12

Asp Ala Ser Asn Arg Ala Thr
1               5

<210> SEQ ID NO 13
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 13 cag cag cgt agc aac tgg cct ccg gcg                             27
Gln Gln Arg Ser Asn Trp Pro Pro Ala
1               5

<210> SEQ ID NO 14
<211> LENGTH: 9
<212> TYPE: PRT
<213> ORGANISM: Homo sapiens

<400> SEQUENCE: 14

Gln Gln Arg Ser Asn Trp Pro Pro Ala
1               5

<210> SEQ ID NO 15
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 15

```
gaa att gtg ttg aca cag tct cca gcc acc ctg tct ttg tct cca ggg    48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac    96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc   144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc   192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct   240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ccg   288
Glu Asp Phe Ala Val Tyr Tyr Cys Gln Gln Arg Ser Asn Trp Pro Pro
                85                  90                  95 gcg ttc ggc caa ggg acc aag gtg gaa atc aaa                       321
Ala Phe Gly Gln Gly Thr Lys Val Glu Ile Lys
            100                 105
```

<210> SEQ ID NO 16
<211> LENGTH: 107
<212> TYPE: PRT
<213> ORGANISM: Homo sapiens

<400> SEQUENCE: 16

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gln Gly Thr Lys Val Glu Ile Lys
            100                 105
```

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser Gly Gly Gly Gly Ser
1               5                   10

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgaaacacc tgtggttctt c                                             21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgccaggggg aagaccgatg g                                             21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atggaarccc cagcgcagct tctc                                          24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgggaagatg aagacagatg                                          20

<210> SEQ ID NO 24
<211> LENGTH: 19
<212> TYPE: PRT
<213> ORGANISM: Mus musculus

<400> SEQUENCE: 24

Met Gly Trp Ser Cys Ile Ile Leu Phe Leu Val Ala Thr Ala Thr Gly
1               5                   10                  15

Val His Ser

<210> SEQ ID NO 25
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagaagcttg ccgccaccat gggatggtca tgtatcatcc ttttctagt agc         53

<210> SEQ ID NO 26
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 tccttttct agtagcaact gcaactggag tacattcaca gctgcagctg caggagtc     58

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgcgctagct gaggagacgg tgaccagggt tccctgg                          37

<210> SEQ ID NO 28
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 tccttttct agtagcaact gcaactggag tacattcaga aattgtgttg acacagtc     58

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcgcgtacgt ttgatttcca ccttggtccc ttggccg                          37

<210> SEQ ID NO 30
<211> LENGTH: 1431
<212> TYPE: DNA
<213> ORGANISM: Homo sapiens
<220> FEATURE:
<221> NAME/KEY: CDS
<222> LOCATION: (1)..(1431)

<400> SEQUENCE: 30

| | | | | | | | | | | | | | | | | |
|---|---|---|---|---|---|---|---|---|---|---|---|---|---|---|---|---|
| atg | gga | tgg | tca | tgt | atc | atc | ctt | ttt | cta | gta | gca | act | gca | act | gga | 48 |
| Met | Gly | Trp | Ser | Cys | Ile | Ile | Leu | Phe | Leu | Val | Ala | Thr | Ala | Thr | Gly | |
| 1 | | | | 5 | | | | | 10 | | | | | 15 | | |
| gta | cat | tca | cag | ctg | cag | ctg | cag | gag | tcg | ggc | cca | gga | ctg | gtg | aag | 96 |
| Val | His | Ser | Gln | Leu | Gln | Leu | Gln | Glu | Ser | Gly | Pro | Gly | Leu | Val | Lys | |
| | | | 20 | | | | | 25 | | | | | 30 | | | |
| cct | tcg | gag | acc | ctg | tcc | ctc | acc | tgc | act | gtc | tct | ggt | ggc | tcc | atc | 144 |
| Pro | Ser | Glu | Thr | Leu | Ser | Leu | Thr | Cys | Thr | Val | Ser | Gly | Gly | Ser | Ile | |
| | | 35 | | | | | 40 | | | | | 45 | | | | |
| aac | agt | agt | agt | tac | tac | tgg | ggc | tgg | ctc | cgc | cag | tcc | cca | ggg | aag | 192 |
| Asn | Ser | Ser | Ser | Tyr | Tyr | Trp | Gly | Trp | Leu | Arg | Gln | Ser | Pro | Gly | Lys | |
| 50 | | | | | 55 | | | | | 60 | | | | | | |
| ggg | ctg | gag | tgg | att | ggg | agt | ttc | ttt | tat | act | ggg | agc | acc | tac | tac | 240 |
| Gly | Leu | Glu | Trp | Ile | Gly | Ser | Phe | Phe | Tyr | Thr | Gly | Ser | Thr | Tyr | Tyr | |
| 65 | | | | 70 | | | | | 75 | | | | | 80 | | |
| aac | ccg | tcc | ctc | agg | agt | cga | ctc | acc | ata | tcc | gta | gac | acg | tcc | aag | 288 |
| Asn | Pro | Ser | Leu | Arg | Ser | Arg | Leu | Thr | Ile | Ser | Val | Asp | Thr | Ser | Lys | |
| | | | 85 | | | | | 90 | | | | | 95 | | | |
| aac | cag | ttc | tcc | ctg | atg | ctg | agt | tct | gtg | acc | gcc | gca | gac | acg | gct | 336 |
| Asn | Gln | Phe | Ser | Leu | Met | Leu | Ser | Ser | Val | Thr | Ala | Ala | Asp | Thr | Ala | |
| | | | 100 | | | | | 105 | | | | | 110 | | | |
| gta | tat | tac | tgt | gcg | aga | cag | tcc | acg | tat | tac | tat | ggt | tcg | ggg | aat | 384 |
| Val | Tyr | Tyr | Cys | Ala | Arg | Gln | Ser | Thr | Tyr | Tyr | Tyr | Gly | Ser | Gly | Asn | |
| | | 115 | | | | | 120 | | | | | 125 | | | | |
| tat | tat | ggc | tgg | ttc | gac | cgc | tgg | gac | cag | gga | acc | ctg | gtc | acc | gtc | 432 |
| Tyr | Tyr | Gly | Trp | Phe | Asp | Arg | Trp | Asp | Gln | Gly | Thr | Leu | Val | Thr | Val | |
| | 130 | | | | | 135 | | | | | 140 | | | | | |
| tcc | tca | gct | agc | acc | aag | ggc | cca | tcg | gtc | ttc | ccc | ctg | gca | ccc | tcc | 480 |
| Ser | Ser | Ala | Ser | Thr | Lys | Gly | Pro | Ser | Val | Phe | Pro | Leu | Ala | Pro | Ser | |
| 145 | | | | | 150 | | | | | 155 | | | | | 160 | |
| tcc | aag | agc | acc | tct | ggg | ggc | aca | gcg | gcc | ctg | ggc | tgc | ctg | gtc | aag | 528 |
| Ser | Lys | Ser | Thr | Ser | Gly | Gly | Thr | Ala | Ala | Leu | Gly | Cys | Leu | Val | Lys | |
| | | | | 165 | | | | | 170 | | | | | 175 | | |
| gac | tac | ttc | ccc | gaa | ccg | gtg | acg | gtg | tcg | tgg | aac | tca | ggc | gcc | ctg | 576 |
| Asp | Tyr | Phe | Pro | Glu | Pro | Val | Thr | Val | Ser | Trp | Asn | Ser | Gly | Ala | Leu | |
| | | | 180 | | | | | 185 | | | | | 190 | | | |
| acc | agc | ggc | gtg | cac | acc | ttc | ccg | gct | gtc | cta | cag | tcc | tca | gga | ctc | 624 |
| Thr | Ser | Gly | Val | His | Thr | Phe | Pro | Ala | Val | Leu | Gln | Ser | Ser | Gly | Leu | |
| | | 195 | | | | | 200 | | | | | 205 | | | | |
| tac | tcc | ctc | agc | agc | gtg | gtg | acc | gtg | ccc | tcc | agc | agc | ttg | ggc | acc | 672 |
| Tyr | Ser | Leu | Ser | Ser | Val | Val | Thr | Val | Pro | Ser | Ser | Ser | Leu | Gly | Thr | |
| | 210 | | | | | 215 | | | | | 220 | | | | | |
| cag | acc | tac | atc | tgc | aac | gtg | aat | cac | aag | ccc | agc | aac | acc | aag | gtg | 720 |
| Gln | Thr | Tyr | Ile | Cys | Asn | Val | Asn | His | Lys | Pro | Ser | Asn | Thr | Lys | Val | |
| 225 | | | | | 230 | | | | | 235 | | | | | 240 | |
| gac | aag | aga | gtt | gag | ccc | aaa | tct | tgt | gac | aaa | act | cac | aca | tgc | cca | 768 |
| Asp | Lys | Arg | Val | Glu | Pro | Lys | Ser | Cys | Asp | Lys | Thr | His | Thr | Cys | Pro | |
| | | | | 245 | | | | | 250 | | | | | 255 | | |
| ccg | tgc | cca | gca | cct | gaa | ctc | ctg | ggg | gga | ccg | tca | gtc | ttc | ctc | ttc | 816 |
| Pro | Cys | Pro | Ala | Pro | Glu | Leu | Leu | Gly | Gly | Pro | Ser | Val | Phe | Leu | Phe | |
| | | | 260 | | | | | 265 | | | | | 270 | | | |

```
ccc cca aaa ccc aag gac acc ctc atg atc tcc cgg acc cct gag gtc      864
Pro Pro Lys Pro Lys Asp Thr Leu Met Ile Ser Arg Thr Pro Glu Val
        275                 280                 285 aca tgc gtg gtg gtg gac gtg agc cac gaa gac cct gag gtc aag ttc      912
Thr Cys Val Val Val Asp Val Ser His Glu Asp Pro Glu Val Lys Phe
    290                 295                 300 aac tgg tac gtg gac ggc gtg gag gtg cat aat gcc aag aca aag ccg      960
Asn Trp Tyr Val Asp Gly Val Glu Val His Asn Ala Lys Thr Lys Pro
305                 310                 315                 320 cgg gag gag cag tac aac agc acg tac cgt gtg gtc agc gtc ctc acc     1008
Arg Glu Glu Gln Tyr Asn Ser Thr Tyr Arg Val Val Ser Val Leu Thr
                325                 330                 335 gtc ctg cac cag gac tgg ctg aat ggc aag gag tac aag tgc aag gtc     1056
Val Leu His Gln Asp Trp Leu Asn Gly Lys Glu Tyr Lys Cys Lys Val
            340                 345                 350 tcc aac aaa gcc ctc cca gcc ccc atc gag aaa acc atc tcc aaa gcc     1104
Ser Asn Lys Ala Leu Pro Ala Pro Ile Glu Lys Thr Ile Ser Lys Ala
        355                 360                 365 aaa ggg cag ccc cga gaa cca cag gtg tac acc ctg ccc cca tcc cgg     1152
Lys Gly Gln Pro Arg Glu Pro Gln Val Tyr Thr Leu Pro Pro Ser Arg
    370                 375                 380 gag gag atg acc aag aac cag gtc agc ctg acc tgc ctg gtc aaa ggc     1200
Glu Glu Met Thr Lys Asn Gln Val Ser Leu Thr Cys Leu Val Lys Gly
385                 390                 395                 400 ttc tat ccc agc gac atc gcc gtg gag tgg gag agc aat ggg cag ccg     1248
Phe Tyr Pro Ser Asp Ile Ala Val Glu Trp Glu Ser Asn Gly Gln Pro
                405                 410                 415 gag aac aac tac aag acc acg cct ccc gtg ctg gac tcc gac ggc tcc     1296
Glu Asn Asn Tyr Lys Thr Thr Pro Pro Val Leu Asp Ser Asp Gly Ser
            420                 425                 430 ttc ttc ctc tat agc aag ctc acc gtg gac aag agc agg tgg cag cag     1344
Phe Phe Leu Tyr Ser Lys Leu Thr Val Asp Lys Ser Arg Trp Gln Gln
        435                 440                 445 ggg aac gtc ttc tca tgc tcc gtg atg cat gag gct ctg cac aac cac     1392
Gly Asn Val Phe Ser Cys Ser Val Met His Glu Ala Leu His Asn His
    450                 455                 460 tac acg cag aag agc ctc tcc ctg tcc ccg ggt aaa tga                  1431
Tyr Thr Gln Lys Ser Leu Ser Leu Ser Pro Gly Lys
465                 470                 475
```

<210> SEQ ID NO 31
<211> LENGTH: 476
<212> TYPE: PRT
<213> ORGANISM: Homo sapiens

<400> SEQUENCE: 31

```
Met Gly Trp Ser Cys Ile Ile Leu Phe Leu Val Ala Thr Ala Thr Gly
1               5                   10                  15

Val His Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Asn Ser Ser Ser Tyr Tyr Trp Gly Trp Leu Arg Gln Ser Pro Gly Lys
    50                  55                  60

Gly Leu Glu Trp Ile Gly Ser Phe Phe Tyr Thr Gly Ser Thr Tyr Tyr
65                  70                  75                  80

Asn Pro Ser Leu Arg Ser Arg Leu Thr Ile Ser Val Asp Thr Ser Lys
                85                  90                  95

Asn Gln Phe Ser Leu Met Leu Ser Ser Val Thr Ala Ala Asp Thr Ala
            100                 105                 110
```

Val Tyr Tyr Cys Ala Arg Gln Ser Thr Tyr Tyr Gly Ser Gly Asn
            115                 120                 125

Tyr Tyr Gly Trp Phe Asp Arg Trp Asp Gln Gly Thr Leu Val Thr Val
130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
            165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
            195                 200                 205

Tyr Ser Leu Ser Ser Val Val Thr Val Pro Ser Ser Ser Leu Gly Thr
            210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
            370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
            450                 455                 460

Tyr Thr Gln Lys Ser Leu Ser Leu Ser Pro Gly Lys
465                 470                 475

```
<210> SEQ ID NO 32
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 32
```

| | | | | | | | | | | | | | | | |
|---|---|---|---|---|---|---|---|---|---|---|---|---|---|---|---|
| atg | gga | tgg | tca | tgt | atc | atc | ctt | ttt | cta | gta | gca | act | gca | act | gga | 48 |
| Met | Gly | Trp | Ser | Cys | Ile | Ile | Leu | Phe | Leu | Val | Ala | Thr | Ala | Thr | Gly | |
| 1 | | | | 5 | | | | | 10 | | | | | 15 | | |

| gta | cat | tca | gaa | att | gtg | ttg | aca | cag | tct | cca | gcc | acc | ctg | tct | ttg | 96 |
| Val | His | Ser | Glu | Ile | Val | Leu | Thr | Gln | Ser | Pro | Ala | Thr | Leu | Ser | Leu | |
| | | | 20 | | | | | 25 | | | | | 30 | | | |

| tct | cca | ggg | gaa | aga | gcc | acc | ctc | tcc | tgc | agg | gcc | agt | cag | agt | gtt | 144 |
| Ser | Pro | Gly | Glu | Arg | Ala | Thr | Leu | Ser | Cys | Arg | Ala | Ser | Gln | Ser | Val | |
| | | 35 | | | | | 40 | | | | | 45 | | | | |

| agc | agc | tac | tta | gcc | tgg | tac | caa | cag | aaa | cct | ggc | cag | gct | ccc | agg | 192 |
| Ser | Ser | Tyr | Leu | Ala | Trp | Tyr | Gln | Gln | Lys | Pro | Gly | Gln | Ala | Pro | Arg | |
| 50 | | | | | 55 | | | | | 60 | | | | | | |

| ctc | ctc | atc | tat | gat | gca | tcc | aac | agg | gcc | act | ggc | atc | cca | gcc | agg | 240 |
| Leu | Leu | Ile | Tyr | Asp | Ala | Ser | Asn | Arg | Ala | Thr | Gly | Ile | Pro | Ala | Arg | |
| 65 | | | | 70 | | | | | 75 | | | | | 80 | | |

| ttc | agt | ggc | agt | ggg | tct | ggg | aca | gac | ttc | act | ctc | acc | atc | agc | agc | 288 |
| Phe | Ser | Gly | Ser | Gly | Ser | Gly | Thr | Asp | Phe | Thr | Leu | Thr | Ile | Ser | Ser | |
| | | | | 85 | | | | | 90 | | | | | 95 | | |

| cta | gag | cct | gaa | gat | ttt | gca | gtt | tat | tac | tgt | cag | cag | cgt | agc | aac | 336 |
| Leu | Glu | Pro | Glu | Asp | Phe | Ala | Val | Tyr | Tyr | Cys | Gln | Gln | Arg | Ser | Asn | |
| | | | 100 | | | | | 105 | | | | | 110 | | | |

| tgg | cct | ccg | gcg | ttc | ggc | caa | ggg | acc | aag | gtg | gaa | atc | aaa | cgt | acg | 384 |
| Trp | Pro | Pro | Ala | Phe | Gly | Gln | Gly | Thr | Lys | Val | Glu | Ile | Lys | Arg | Thr | |
| | | 115 | | | | | 120 | | | | | 125 | | | | |

| gtg | gct | gca | cca | tct | gtc | ttc | atc | ttc | ccg | cca | tct | gat | gag | cag | ttg | 432 |
| Val | Ala | Ala | Pro | Ser | Val | Phe | Ile | Phe | Pro | Pro | Ser | Asp | Glu | Gln | Leu | |
| | 130 | | | | | 135 | | | | | 140 | | | | | |

| aaa | tct | gga | act | gcc | tct | gtt | gtg | tgc | ctg | ctg | aat | aac | ttc | tat | ccc | 480 |
| Lys | Ser | Gly | Thr | Ala | Ser | Val | Val | Cys | Leu | Leu | Asn | Asn | Phe | Tyr | Pro | |
| 145 | | | | | 150 | | | | | 155 | | | | | 160 | |

| aga | gag | gcc | aaa | gta | cag | tgg | aag | gtg | gat | aac | gcc | ctc | caa | tcg | ggt | 528 |
| Arg | Glu | Ala | Lys | Val | Gln | Trp | Lys | Val | Asp | Asn | Ala | Leu | Gln | Ser | Gly | |
| | | | 165 | | | | | 170 | | | | | 175 | | | |

| aac | tcc | cag | gag | agt | gtc | aca | gag | cag | gac | agc | aag | gac | agc | acc | tac | 576 |
| Asn | Ser | Gln | Glu | Ser | Val | Thr | Glu | Gln | Asp | Ser | Lys | Asp | Ser | Thr | Tyr | |
| | | 180 | | | | | 185 | | | | | 190 | | | | |

| agc | ctc | agc | agc | acc | ctg | acg | ctg | agc | aaa | gca | gac | tac | gag | aaa | cac | 624 |
| Ser | Leu | Ser | Ser | Thr | Leu | Thr | Leu | Ser | Lys | Ala | Asp | Tyr | Glu | Lys | His | |
| | | 195 | | | | | 200 | | | | | 205 | | | | |

| aaa | gtc | tac | gcc | tgc | gaa | gtc | acc | cat | cag | ggc | ctg | agc | tcg | ccc | gtc | 672 |
| Lys | Val | Tyr | Ala | Cys | Glu | Val | Thr | His | Gln | Gly | Leu | Ser | Ser | Pro | Val | |
| | 210 | | | | | 215 | | | | | 220 | | | | | |

| aca | aag | agc | ttc | aac | agg | gga | gag | tgt | tag | | | | | | | 702 |
| Thr | Lys | Ser | Phe | Asn | Arg | Gly | Glu | Cys | | | | | | | | |
| 225 | | | | | 230 | | | | | | | | | | | |

<210> SEQ ID NO 33
<211> LENGTH: 233
<212> TYPE: PRT
<213> ORGANISM: Homo sapiens

<400> SEQUENCE: 33

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

```
Leu Leu Ile Tyr Asp Ala Ser Asn Arg Ala Thr Gly Ile Pro Ala Arg
 65                  70                  75                  80

Phe Ser Gly Ser Gly Ser Gly Thr Asp Phe Thr Leu Thr Ile Ser Ser
                 85                  90                  95

Leu Glu Pro Glu Asp Phe Ala Val Tyr Tyr Cys Gln Gln Arg Ser Asn
            100                 105                 110

Trp Pro Pro Ala Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 34
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 34 agc tat gct atc agc                                              15
Ser Tyr Ala Ile Ser
1               5

<210> SEQ ID NO 35
<211> LENGTH: 5
<212> TYPE: PRT
<213> ORGANISM: Homo sapiens

<400> SEQUENCE: 35

Ser Tyr Ala Ile Ser
1               5

<210> SEQ ID NO 36
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 36 ggg atc atc cct atc ttt ggt aca gca aac tac gca cag aag ttc cag    48
Gly Ile Ile Pro Ile Phe Gly Thr Ala Asn Tyr Ala Gln Lys Phe Gln
1               5                   10                  15 ggc                                                               51
Gly

<210> SEQ ID NO 37
```

```
<211> LENGTH: 17
<212> TYPE: PRT
<213> ORGANISM: Homo sapiens

<400> SEQUENCE: 37

Gly Ile Ile Pro Ile Phe Gly Thr Ala Asn Tyr Ala Gln Lys Phe Gln
1               5                   10                  15

Gly

<210> SEQ ID NO 38
<211> LENGTH: 63
<212> TYPE: DNA
<213> ORGANISM: Homo sapiens
<220> FEATURE:
<221> NAME/KEY: CDS
<222> LOCATION: (1)..(63)

<400> SEQUENCE: 38 gcg cca tta cga ttt ttg gag tgg tcc acc caa gac cac tac tac tac      48
Ala Pro Leu Arg Phe Leu Glu Trp Ser Thr Gln Asp His Tyr Tyr Tyr
1               5                   10                  15 tac tac atg gac gtc                                                   63
Tyr Tyr Met Asp Val
            20

<210> SEQ ID NO 39
<211> LENGTH: 21
<212> TYPE: PRT
<213> ORGANISM: Homo sapiens

<400> SEQUENCE: 39

Ala Pro Leu Arg Phe Leu Glu Trp Ser Thr Gln Asp His Tyr Tyr Tyr
1               5                   10                  15

Tyr Tyr Met Asp Val
            20

<210> SEQ ID NO 40
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 40 gag gtc cag ctg gtg cag tct ggg gct gag gtg aag aag cct ggg tcc      48
Glu Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
                20                  25                  30 gct atc agc tgg gtg cga cag gcc cct gga caa ggg ctt gag tgg atg      144
Ala Ile Ser Trp Val Arg Gln Ala Pro Gly Gln Gly Leu Glu Trp Met
            35                  40                  45 gga ggg atc atc cct atc ttt ggt aca gca aac tac gca cag aag ttc      192
Gly Gly Ile Ile Pro Ile Phe Gly Thr Ala Asn Tyr Ala Gln Lys Phe
        50                  55                  60 cag ggc aga gtc acg att acc gcg gac aaa tcc acg agc aca gcc tac      240
Gln Gly Arg Val Thr Ile Thr Ala Asp Lys Ser Thr Ser Thr Ala Tyr
65                  70                  75                  80 atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95 gcg aga gcg cca tta cga ttt ttg gag tgg tcc acc caa gac cac tac      336
```

| | | | | | | | | | | | | | | | |
|---|---|---|---|---|---|---|---|---|---|---|---|---|---|---|---|
| Ala | Arg | Ala | Pro | Leu | Arg | Phe | Leu | Glu | Trp | Ser | Thr | Gln | Asp | His | Tyr |
| | | | 100 | | | | 105 | | | | 110 | | | | |

```
tac tac tac tac atg gac gtc tgg ggc aaa ggg acc acg gtc acc gtc       384
Tyr Tyr Tyr Tyr Met Asp Val Trp Gly Lys Gly Thr Thr Val Thr Val
            115                 120                 125 tca agc                                                                390
Ser Ser
    130
```

<210> SEQ ID NO 41
<211> LENGTH: 130
<212> TYPE: PRT
<213> ORGANISM: Homo sapiens

<400> SEQUENCE: 41

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser
    130
```

<210> SEQ ID NO 42
<211> LENGTH: 1440
<212> TYPE: DNA
<213> ORGANISM: Homo sapiens
<220> FEATURE:
<221> NAME/KEY: CDS
<222> LOCATION: (1)..(1440)

<400> SEQUENCE: 42

```
atg gga tgg tca tgt atc atc ctt ttt cta gta gca act gca act gga        48
Met Gly Trp Ser Cys Ile Ile Leu Phe Leu Val Ala Thr Ala Thr Gly
1               5                   10                  15 gta cat tca gag gtc cag ctg gtg cag tct ggg gct gag gtg aag aag        96
Val His Ser Glu Val Gln Leu Val Gln Ser Gly Ala Glu Val Lys Lys
            20                  25                  30 cct ggg tcc tcg gtg aag gtc tcc tgc aag gct tct gga ggc acc ttc       144
Pro Gly Ser Ser Val Lys Val Ser Cys Lys Ala Ser Gly Gly Thr Phe
        35                  40                  45 agc agc tat gct atc agc tgg gtg cga cag gcc cct gga caa ggg ctt       192
Ser Ser Tyr Ala Ile Ser Trp Val Arg Gln Ala Pro Gly Gln Gly Leu
50                  55                  60 gag tgg atg gga ggg atc atc cct atc ttt ggt aca gca aac tac gca       240
Glu Trp Met Gly Gly Ile Ile Pro Ile Phe Gly Thr Ala Asn Tyr Ala
65                  70                  75                  80 cag aag ttc cag ggc aga gtc acg att acc gcg gac aaa tcc acg agc       288
Gln Lys Phe Gln Gly Arg Val Thr Ile Thr Ala Asp Lys Ser Thr Ser
                85                  90                  95
```

```
aca gcc tac atg gag ctg agc agc ctg aga tct gag gac acg gcc gtg      336
Thr Ala Tyr Met Glu Leu Ser Ser Leu Arg Ser Glu Asp Thr Ala Val
            100                 105                 110 tat tac tgt gcg aga gcg cca tta cga ttt ttg gag tgg tcc acc caa      384
Tyr Tyr Cys Ala Arg Ala Pro Leu Arg Phe Leu Glu Trp Ser Thr Gln
        115                 120                 125 gac cac tac tac tac tac tac atg gac gtc tgg ggc aaa ggg acc acg      432
Asp His Tyr Tyr Tyr Tyr Tyr Met Asp Val Trp Gly Lys Gly Thr Thr
    130                 135                 140 gtc acc gtc tca agc gcc tcc acc aag ggc cca tcg gtc ttc ccc ctg      480
Val Thr Val Ser Ser Ala Ser Thr Lys Gly Pro Ser Val Phe Pro Leu
145                 150                 155                 160 gca ccc tcc tcc aag agc acc tct ggg ggc aca gcg gcc ctg ggc tgc      528
Ala Pro Ser Ser Lys Ser Thr Ser Gly Gly Thr Ala Ala Leu Gly Cys
                165                 170                 175 ctg gtc aag gac tac ttc ccc gaa ccg gtg acg gtg tcg tgg aac tca      576
Leu Val Lys Asp Tyr Phe Pro Glu Pro Val Thr Val Ser Trp Asn Ser
            180                 185                 190 ggc gcc ctg acc agc ggc gtg cac acc ttc ccg gct gtc cta cag tcc      624
Gly Ala Leu Thr Ser Gly Val His Thr Phe Pro Ala Val Leu Gln Ser
        195                 200                 205 tca gga ctc tac tcc ctc agc agc gtg gtg acc gtg ccc tcc agc agc      672
Ser Gly Leu Tyr Ser Leu Ser Ser Val Val Thr Val Pro Ser Ser Ser
    210                 215                 220 ttg ggc acc cag acc tac atc tgc aac gtg aat cac aag ccc agc aac      720
Leu Gly Thr Gln Thr Tyr Ile Cys Asn Val Asn His Lys Pro Ser Asn
225                 230                 235                 240 acc aag gtg gac aag aaa gtt gag ccc aaa tct tgt gac aaa act cac      768
Thr Lys Val Asp Lys Lys Val Glu Pro Lys Ser Cys Asp Lys Thr His
                245                 250                 255 aca tgc cca ccg tgc cca gca cct gaa ctc ctg ggg gga ccg tca gtc      816
Thr Cys Pro Pro Cys Pro Ala Pro Glu Leu Leu Gly Gly Pro Ser Val
            260                 265                 270 ttc ctc ttc ccc cca aaa ccc aag gac acc ctc atg atc tcc cgg acc      864
Phe Leu Phe Pro Pro Lys Pro Lys Asp Thr Leu Met Ile Ser Arg Thr
        275                 280                 285 cct gag gtc aca tgc gtg gtg gtg gac gtg agc cac gaa gac cct gag      912
Pro Glu Val Thr Cys Val Val Val Asp Val Ser His Glu Asp Pro Glu
    290                 295                 300 gtc aag ttc aac tgg tac gtg gac ggc gtg gag gtg cat aat gcc aag      960
Val Lys Phe Asn Trp Tyr Val Asp Gly Val Glu Val His Asn Ala Lys
305                 310                 315                 320 aca aag ccg cgg gag gag cag tac aac agc acg tac cgg gtg gtc agc     1008
Thr Lys Pro Arg Glu Glu Gln Tyr Asn Ser Thr Tyr Arg Val Val Ser
                325                 330                 335 gtc ctc acc gtc ctg cac cag gac tgg ctg aat ggc aag gag tac aag     1056
Val Leu Thr Val Leu His Gln Asp Trp Leu Asn Gly Lys Glu Tyr Lys
            340                 345                 350 tgc aag gtc tcc aac aaa gcc ctc cca gcc ccc atc gag aaa acc atc     1104
Cys Lys Val Ser Asn Lys Ala Leu Pro Ala Pro Ile Glu Lys Thr Ile
        355                 360                 365 tcc aaa gcc aaa ggg cag ccc cga gaa cca cag gtg tac acc ctg ccc     1152
Ser Lys Ala Lys Gly Gln Pro Arg Glu Pro Gln Val Tyr Thr Leu Pro
    370                 375                 380 cca tcc cgg gag gag atg acc aag aac cag gtc agc ctg acc tgc ctg     1200
Pro Ser Arg Glu Glu Met Thr Lys Asn Gln Val Ser Leu Thr Cys Leu
385                 390                 395                 400 gtc aaa ggc ttc tat ccc agc gac atc gcc gtg gag tgg gag agc aat     1248
Val Lys Gly Phe Tyr Pro Ser Asp Ile Ala Val Glu Trp Glu Ser Asn
                405                 410                 415
```

```
ggg cag ccg gag aac aac tac aag acc acg cct ccc gtg ctg gac tcc   1296
Gly Gln Pro Glu Asn Asn Tyr Lys Thr Thr Pro Pro Val Leu Asp Ser
            420                 425                 430 gac ggc tcc ttc ttc ctc tac agc aag ctc acc gtg gac aag agc agg   1344
Asp Gly Ser Phe Phe Leu Tyr Ser Lys Leu Thr Val Asp Lys Ser Arg
            435                 440                 445 tgg cag cag ggg aac gtc ttc tca tgc tcc gtg atg cat gag gct ctg   1392
Trp Gln Gln Gly Asn Val Phe Ser Cys Ser Val Met His Glu Ala Leu
450                 455                 460 cac aac cac tac acg cag aag agc ctc tcc ctg tct ccg ggt aaa tga   1440
His Asn His Tyr Thr Gln Lys Ser Leu Ser Leu Ser Pro Gly Lys
465                 470                 475
```

<210> SEQ ID NO 43
<211> LENGTH: 479
<212> TYPE: PRT
<213> ORGANISM: Homo sapiens

<400> SEQUENCE: 43

```
Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ala Pro Leu Arg Phe Leu Glu Trp Ser Thr Gln
        115                 120                 125

Asp His Tyr Tyr Tyr Tyr Met Asp Val Trp Gly Lys Gly Thr Thr
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285
```

```
Pro Glu Val Thr Cys Val Val Asp Val Ser His Glu Asp Pro Glu
    290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Glu Tyr Lys
            340                 345                 350
Cys Lys Val Ser Asn Lys Ala Leu Pro Ala Pro Ile Glu Lys Thr Ile
        355                 360                 365
Ser Lys Ala Lys Gly Gln Pro Arg Glu Pro Gln Val Tyr Thr Leu Pro
    370                 375                 380
Pro Ser Arg Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Lys Leu Thr Val Asp Lys Ser Arg
        435                 440                 445
Trp Gln Gln Gly Asn Val Phe Ser Cys Ser Val Met His Glu Ala Leu
    450                 455                 460
His Asn His Tyr Thr Gln Lys Ser Leu Ser Leu Ser Pro Gly Lys
465                 470                 475

<210> SEQ ID NO 44
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 44 caa gga gac agc ctc aga agc tat tat gca acc                    33
Gln Gly Asp Ser Leu Arg Ser Tyr Tyr Ala Thr
1               5                   10

<210> SEQ ID NO 45
<211> LENGTH: 11
<212> TYPE: PRT
<213> ORGANISM: Homo sapiens

<400> SEQUENCE: 45

Gln Gly Asp Ser Leu Arg Ser Tyr Tyr Ala Thr
1               5                   10

<210> SEQ ID NO 46
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 46 ggt gaa aat aag cgg ccc tca                                    21
Gly Glu Asn Lys Arg Pro Ser
1               5

<210> SEQ ID NO 47
<211> LENGTH: 7
```

```
<212> TYPE: PRT
<213> ORGANISM: Homo sapiens

<400> SEQUENCE: 47

Gly Glu Asn Lys Arg Pro Ser
1               5

<210> SEQ ID NO 48
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 48 aaa tct cgg gat ggc agt ggt caa cat ctg gtg                     33
Lys Ser Arg Asp Gly Ser Gly Gln His Leu Val
1               5                   10

<210> SEQ ID NO 49
<211> LENGTH: 11
<212> TYPE: PRT
<213> ORGANISM: Homo sapiens

<400> SEQUENCE: 49

Lys Ser Arg Asp Gly Ser Gly Gln His Leu Val
1               5                   10

<210> SEQ ID NO 50
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 50 tct tct gag ctg act cag gac cct gct gtg tct gtg gcc ttg gga cag     48
Ser Ser Glu Leu Thr Gln Asp Pro Ala Val Ser Val Ala Leu Gly Gln
1               5                   10                  15 aca gtc agg atc aca tgc caa gga gac agc ctc aga agc tat tat gca     96
Thr Val Arg Ile Thr Cys Gln Gly Asp Ser Leu Arg Ser Tyr Tyr Ala
                20                  25                  30 acc tgg tac cag cag aag cca gga cag gcc cct att ctt gtc atc tat    144
Thr Trp Tyr Gln Gln Lys Pro Gly Gln Ala Pro Ile Leu Val Ile Tyr
            35                  40                  45 ggt gaa aat aag cgg ccc tca ggg atc cca gac cga ttc tct ggc tcc    192
Gly Glu Asn Lys Arg Pro Ser Gly Ile Pro Asp Arg Phe Ser Gly Ser
        50                  55                  60 agc tca gga aac aca gct tcc ttg acc atc act ggg gct cag gca gaa    240
Ser Ser Gly Asn Thr Ala Ser Leu Thr Ile Thr Gly Ala Gln Ala Glu
65                  70                  75                  80 gat gag gct gac tac tat tgt aaa tct cgg gat ggc agt ggt caa cat    288
Asp Glu Ala Asp Tyr Tyr Cys Lys Ser Arg Asp Gly Ser Gly Gln His
                85                  90                  95 ctg gtg ttc ggc gga ggg acc aag ctg acc gtc cta ggt                327
Leu Val Phe Gly Gly Gly Thr Lys Leu Thr Val Leu Gly
                100                 105

<210> SEQ ID NO 51
<211> LENGTH: 109
<212> TYPE: PRT
<213> ORGANISM: Homo sapiens

<400> SEQUENCE: 51
```

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly
            100                 105
```

```
<210> SEQ ID NO 52
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 52 atg gga tgg tca tgt atc atc ctt ttt cta gta gca act gca act gga         48
Met Gly Trp Ser Cys Ile Ile Leu Phe Leu Val Ala Thr Ala Thr Gly
1               5                   10                  15 gta cat tca tct tct gag ctg act cag gac cct gct gtg tct gtg gcc         96
Val His Ser Ser Ser Glu Leu Thr Gln Asp Pro Ala Val Ser Val Ala
            20                  25                  30 ttg gga cag aca gtc agg atc aca tgc caa gga gac agc ctc aga agc        144
Leu Gly Gln Thr Val Arg Ile Thr Cys Gln Gly Asp Ser Leu Arg Ser
        35                  40                  45 tat tat gca acc tgg tac cag cag aag cca gga cag gcc cct att ctt        192
Tyr Tyr Ala Thr Trp Tyr Gln Gln Lys Pro Gly Gln Ala Pro Ile Leu
    50                  55                  60 gtc atc tat ggt gaa aat aag cgg ccc tca ggg atc cca gac cga ttc        240
Val Ile Tyr Gly Glu Asn Lys Arg Pro Ser Gly Ile Pro Asp Arg Phe
65                  70                  75                  80 tct ggc tcc agc tca gga aac aca gct tcc ttg acc atc act ggg gct        288
Ser Gly Ser Ser Ser Gly Asn Thr Ala Ser Leu Thr Ile Thr Gly Ala
                85                  90                  95 cag gca gaa gat gag gct gac tac tat tgt aaa tct cgg gat ggc agt        336
Gln Ala Glu Asp Glu Ala Asp Tyr Tyr Cys Lys Ser Arg Asp Gly Ser
            100                 105                 110 ggt caa cat ctg gtg ttc ggc gga ggg acc aag ctg acc gtc cta ggt        384
Gly Gln His Leu Val Phe Gly Gly Gly Thr Lys Leu Thr Val Leu Gly
        115                 120                 125 cag ccc aag gct gcc ccc tcg gtc act ctg ttc ccg ccc tcc tct gag        432
Gln Pro Lys Ala Ala Pro Ser Val Thr Leu Phe Pro Pro Ser Ser Glu
    130                 135                 140 gag ctt caa gcc aac aag gcc aca ctg gtg tgt ctc ata agt gac ttc        480
Glu Leu Gln Ala Asn Lys Ala Thr Leu Val Cys Leu Ile Ser Asp Phe
145                 150                 155                 160 tac ccg gga gcc gtg aca gtg gcc tgg aag gca gat agc agc ccc gtc        528
Tyr Pro Gly Ala Val Thr Val Ala Trp Lys Ala Asp Ser Ser Pro Val
                165                 170                 175 aag gcg gga gtg gag acc acc aca ccc tcc aaa caa agc aac aac aag        576
Lys Ala Gly Val Glu Thr Thr Thr Pro Ser Lys Gln Ser Asn Asn Lys
            180                 185                 190
```

```
tac gcg gcc agc agc tat ctg agc ctg acg cct gag cag tgg aag tcc    624
Tyr Ala Ala Ser Ser Tyr Leu Ser Leu Thr Pro Glu Gln Trp Lys Ser
            195                 200                 205 cac aga agc tac agc tgc cag gtc acg cat gaa ggg agc acc gtg gag    672
His Arg Ser Tyr Ser Cys Gln Val Thr His Glu Gly Ser Thr Val Glu
210                 215                 220 aag aca gtg gcc cct gca gaa tgc tct tga                            702
Lys Thr Val Ala Pro Ala Glu Cys Ser
225                 230
```

<210> SEQ ID NO 53
<211> LENGTH: 233
<212> TYPE: PRT
<213> ORGANISM: Homo sapiens

<400> SEQUENCE: 53

```
Met Gly Trp Ser Cys Ile Ile Leu Phe Leu Val Ala Thr Ala Thr Gly
1               5                   10                  15

Val His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Ser
        35                  40                  45

Tyr Tyr Ala Thr Trp Tyr Gln Gln Lys Pro Gly Gln Ala Pro Ile Leu
    50                  55                  60

Val Ile Tyr Gly Glu Asn Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Lys Ser Arg Asp Gly Ser
            100                 105                 110

Gly Gln His Leu Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Ala Glu Cys Ser
225                 230
```

<210> SEQ ID NO 54
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 54

```
caa gga gac agc ctc aga agc tat tat gca agc                        33
Gln Gly Asp Ser Leu Arg Ser Tyr Tyr Ala Ser
1               5                   10
```

```
<210> SEQ ID NO 55
<211> LENGTH: 11
<212> TYPE: PRT
<213> ORGANISM: Homo sapiens

<400> SEQUENCE: 55

Gln Gly Asp Ser Leu Arg Ser Tyr Tyr Ala Ser
1               5                   10

<210> SEQ ID NO 56
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 56 ggt aaa aac aac cgg ccc tca                                    21
Gly Lys Asn Asn Arg Pro Ser
1               5

<210> SEQ ID NO 57
<211> LENGTH: 7
<212> TYPE: PRT
<213> ORGANISM: Homo sapiens

<400> SEQUENCE: 57

Gly Lys Asn Asn Arg Pro Ser
1               5

<210> SEQ ID NO 58
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 58 aac tcc cgg gac aac agt gat aac cgt ctg ata                    33
Asn Ser Arg Asp Asn Ser Asp Asn Arg Leu Ile
1               5                   10

<210> SEQ ID NO 59
<211> LENGTH: 11
<212> TYPE: PRT
<213> ORGANISM: Homo sapiens

<400> SEQUENCE: 59

Asn Ser Arg Asp Asn Ser Asp Asn Arg Leu Ile
1               5                   10

<210> SEQ ID NO 60
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 60 tct tct gag ctg act cag gac cct gct gtg tct gtg gcc ttg gga cag    48
Ser Ser Glu Leu Thr Gln Asp Pro Ala Val Ser Val Ala Leu Gly Gln
1               5                   10                  15
```

```
aca gtc agg atc aca tgc caa gga gac agc ctc aga agc tat tat gca      96
Thr Val Arg Ile Thr Cys Gln Gly Asp Ser Leu Arg Ser Tyr Tyr Ala
         20                  25                  30 agc tgg tac cag cag aag cca gga cag gcc cct gta ctt gtc atc tat     144
Ser Trp Tyr Gln Gln Lys Pro Gly Gln Ala Pro Val Leu Val Ile Tyr
     35                  40                  45 ggt aaa aac aac cgg ccc tca ggg atc cca gac cga ttc tct ggc tcc     192
Gly Lys Asn Asn Arg Pro Ser Gly Ile Pro Asp Arg Phe Ser Gly Ser
 50                  55                  60 agc tca gga aac aca gct tcc ttg acc atc act ggg gct cag gcg gaa     240
Ser Ser Gly Asn Thr Ala Ser Leu Thr Ile Thr Gly Ala Gln Ala Glu
65                  70                  75                  80 gat gag gct gac tat tac tgt aac tcc cgg gac aac agt gat aac cgt     288
Asp Glu Ala Asp Tyr Tyr Cys Asn Ser Arg Asp Asn Ser Asp Asn Arg
             85                  90                  95 ctg ata ttt ggc ggc ggg acc aag ctg acc gtc ctc agt                 327
Leu Ile Phe Gly Gly Gly Thr Lys Leu Thr Val Leu Ser
            100                 105

<210> SEQ ID NO 61
<211> LENGTH: 109
<212> TYPE: PRT
<213> ORGANISM: Homo sapiens

<400> SEQUENCE: 61

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Ser Asp Asn Arg
                85                  90                  95

Leu Ile Phe Gly Gly Gly Thr Lys Leu Thr Val Leu Ser
            100                 105

<210> SEQ ID NO 62
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 62 atg gga tgg tca tgt atc atc ctt ttt cta gta gca act gca act gga      48
Met Gly Trp Ser Cys Ile Ile Leu Phe Leu Val Ala Thr Ala Thr Gly
1               5                   10                  15 gta cat tca tct tct gag ctg act cag gac cct gct gtg tct gtg gcc     96
Val His Ser Ser Ser Glu Leu Thr Gln Asp Pro Ala Val Ser Val Ala
            20                  25                  30 ttg gga cag aca gtc agg atc aca tgc caa gga gac agc ctc aga agc    144
Leu Gly Gln Thr Val Arg Ile Thr Cys Gln Gly Asp Ser Leu Arg Ser
        35                  40                  45 tat tat gca agc tgg tac cag cag aag cca gga cag gcc cct gta ctt    192
Tyr Tyr Ala Ser Trp Tyr Gln Gln Lys Pro Gly Gln Ala Pro Val Leu
    50                  55                  60
```

```
gtc atc tat ggt aaa aac aac cgg ccc tca ggg atc cca gac cga ttc      240
Val Ile Tyr Gly Lys Asn Asn Arg Pro Ser Gly Ile Pro Asp Arg Phe
 65                  70                  75                  80 tct ggc tcc agc tca gga aac aca gct tcc ttg acc atc act ggg gct      288
Ser Gly Ser Ser Ser Gly Asn Thr Ala Ser Leu Thr Ile Thr Gly Ala
                 85                  90                  95 cag gcg gaa gat gag gct gac tat tac tgt aac tcc cgg gac aac agt      336
Gln Ala Glu Asp Glu Ala Asp Tyr Tyr Cys Asn Ser Arg Asp Asn Ser
            100                 105                 110 gat aac cgt ctg ata ttt ggc ggc ggg acc aag ctg acc gtc ctc agt      384
Asp Asn Arg Leu Ile Phe Gly Gly Gly Thr Lys Leu Thr Val Leu Ser
        115                 120                 125 cag ccc aag gct gcc ccc tcg gtc act ctg ttc ccg ccc tcc tct gag      432
Gln Pro Lys Ala Ala Pro Ser Val Thr Leu Phe Pro Pro Ser Ser Glu
    130                 135                 140 gag ctt caa gcc aac aag gcc aca ctg gtg tgt ctc ata agt gac ttc      480
Glu Leu Gln Ala Asn Lys Ala Thr Leu Val Cys Leu Ile Ser Asp Phe
145                 150                 155                 160 tac ccg gga gcc gtg aca gtg gcc tgg aag gca gat agc agc ccc gtc      528
Tyr Pro Gly Ala Val Thr Val Ala Trp Lys Ala Asp Ser Ser Pro Val
                165                 170                 175 aag gcg gga gtg gag acc acc aca ccc tcc aaa caa agc aac aac aag      576
Lys Ala Gly Val Glu Thr Thr Thr Pro Ser Lys Gln Ser Asn Asn Lys
            180                 185                 190 tac gcg gcc agc agc tat ctg agc ctg acg cct gag cag tgg aag tcc      624
Tyr Ala Ala Ser Ser Tyr Leu Ser Leu Thr Pro Glu Gln Trp Lys Ser
        195                 200                 205 cac aga agc tac agc tgc cag gtc acg cat gaa ggg agc acc gtg gag      672
His Arg Ser Tyr Ser Cys Gln Val Thr His Glu Gly Ser Thr Val Glu
    210                 215                 220 aag aca gtg gcc cct gca gaa tgc tct tga                              702
Lys Thr Val Ala Pro Ala Glu Cys Ser
225                 230

<210> SEQ ID NO 63
<211> LENGTH: 233
<212> TYPE: PRT
<213> ORGANISM: Homo sapiens

<400> SEQUENCE: 63

Met Gly Trp Ser Cys Ile Ile Leu Phe Leu Val Ala Thr Ala Thr Gly
1               5                   10                  15

Val His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Ser
        35                  40                  45

Tyr Tyr Ala Ser Trp Tyr Gln Gln Lys Pro Gly Gln Ala Pro Val Leu
    50                  55                  60

Val Ile Tyr Gly Lys Asn Asn Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Asn Ser
            100                 105                 110

Asp Asn Arg Leu Ile Phe Gly Gly Gly Thr Lys Leu Thr Val Leu Ser
        115                 120                 125

Gln Pro Lys Ala Ala Pro Ser Val Thr Leu Phe Pro Pro Ser Ser Glu
    130                 135                 140
```

-continued

```
Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
                180                 185                 190

Tyr Ala Ala Ser Ser Tyr Leu Ser Leu Thr Pro Glu Gln Trp Lys Ser
            195                 200                 205

His Arg Ser Tyr Ser Cys Gln Val Thr His Glu Gly Ser Thr Val Glu
        210                 215                 220

Lys Thr Val Ala Pro Ala Glu Cys Ser
225                 230
```

ANTIBODIES AGAINST PDGFRα TO INHIBIT TUMOR GROWTH

This application is a divisional of U.S. application Ser. No. 11/917,890 filed on Oct. 15, 2008, now U.S. Pat. No. 8,128,929, which is a §371 of PCT/US2006/023856 filed Jun. 19, 2006.

FIELD OF THE INVENTION

The invention provides methods of treating bone cancer, particularly metastatic bone cancer, by administering an IGF-IR antagonist and/or a PDGFRα antagonist. The invention also provides antibodies that bind to human PDGFRα and neutralize activation of the receptor. The invention further provides a methods for neutralizing activation of PDGFRα, and a methods of treating a mammal with a neoplastic disease using the antibodies alone or in combination with other agents.

BACKGROUND OF THE INVENTION

Prostate cancer is the most common cancer among men, with approximately 220,000 cases and 29,000 deaths annually in the United States. A significant proportion of men diagnosed with prostate cancer have metastatic disease. Further, metastases eventually develop in many other prostate cancer patients despite treatment with surgery or radiotherapy. Bone is the most common site of prostate cancer metastasis, and is also a site to which breast cancers and lung cancers often metastasize. Most prostate cancer metastases are androgen-dependent, so that there is a rapid response to surgical or medical castration, but in virtually all patients, the tumor eventually becomes androgen-independent, leading to significant morbidity and mortality. Once bone metastases occur, currently available therapies have limited effect. The most effective approved therapy that has been described for metastatic prostate cancer (administration of docetaxel) extends median survival approximately three months. (Petrylak et al., 2004, N. Engl. J. Med. 351:1513; Tannock et al., 2004, N. Engl. J. Med. 351:1502) Accordingly, new therapies for metastatic bone cancers are urgently needed.

The insulin-like growth factor receptor (IGF-IR) is a ubiquitous transmembrane tyrosine kinase receptor that is essential for normal fetal and post-natal growth and development. IGF-IR is located on the cell surface of most cell types and serves as the signaling molecule for growth factors IGF-I and IGF-II (collectively termed henceforth IGFs). IGF-IR can stimulate cell proliferation, cell differentiation, changes in cell size, and protect cells from apoptosis. It has also been considered to be quasi-obligatory for cell transformation (reviewed in Adams et al., *Cell. Mol. Life Sci.* 57:1050-93 (2000); Baserga, *Oncogene* 19:5574-81 (2000)). High levels of expression of IGF-IR have been reported in tissue samples from prostate cancer bone metastases. Bone contains the largest store of IGFs in the body.

IGF-IR is a pre-formed hetero-tetramer containing two alpha and two beta chains covalently linked by disulfide bonds. The receptor subunits are synthesized as part of a single polypeptide chain of 180 kd, which is then proteolytically processed into alpha (130 kd) and beta (95 kd) subunits. The entire alpha chain is extracellular and contains the site for ligand binding. The beta chain possesses the transmembrane domain, the tyrosine kinase domain, and a C-terminal extension that is necessary for cell differentiation and transformation, but is dispensable for mitogen signaling and protection from apoptosis.

IGF-IR is highly similar to the insulin receptor (IR), particularly within the beta chain sequence (70% homology). Because of this homology, recent studies have demonstrated that these receptors can form hybrids containing one IR dimer and one IGF-IR dimer (Pandini et al., *Clin. Canc. Res.* 5:1935-19 (1999)). The formation of hybrids occurs in both normal and transformed cells and the hybrid content is dependent upon the concentration of the two homodimer receptors (IR and IGF-IR) within the cell. Although hybrid receptors are composed of IR and IGF-IR pairs, the hybrids bind selectively to IGFs, with affinity similar to that of IGF-IR, and only weakly bind insulin (Siddle and Soos, The IGF System. Humana Press. pp. 199-225. 1999). These hybrids therefore can bind IGFs and transduce signals in both normal and transformed cells.

A second IGF receptor, IGF-IIR, or mannose-6-phosphate (M6P) receptor, also binds IGF-II ligand with high affinity, but lacks tyrosine kinase activity (Oates et al., *Breast Cancer Res. Treat.* 47:269-81 (1998)). Because it results in the degradation of IGF-II, it is considered a sink for IGF-II, antagonizing the growth promoting effects of this ligand. Loss of the IGF-IIR in tumor cells can enhance growth potential through release of its antagonistic effect on the binding of IGF-II with the IGF-IR (Byrd et al., *J. Biol. Chem.* 274:24408-16 (1999)).

Platelet derived growth factor receptors alpha and beta (PDGFRα and PDGFRβ) are type III receptor tyrosine kinases. PDGFRα is critical for development and fulfills important functions into adulthood. For example, mice homozygous for a null mutation die during embryogenesis. At later stages of development, PDGFRα is expressed in many mesenchymal structures, whereas adjacent epithelial cells produce platelet derived growth factors (PDGFs). Tissue samples from normal or hyperplastic prostate glands test negative for PDGFRα, whereas primary prostate tumors and skeletal masses from matched subjects express PDGFRα. Further, of prostate cell lines obtained from different metastatic sites, PDGFRα is found in bone metastasis-derived PC3 cells, but not in cell lines obtained from lymph node (LNCaP) and brain (DU-145) metastases.

The platelet-derived growth factor family of growth factors consists of five different disulphide-linked dimers, PDGF-AA, -BB, -AB, -CC, and -DD, that act via PDGFRα and PDGFRβ. These growth factors are dimeric molecules composed of disulfide-linked polypeptide chains that bind to two receptor proteins simultaneously and induce receptor dimerization, autophosphorylation, and intracellular signaling. PDGFRα and PDGFRβ are structurally similar and can form heterodimers as well as homodimers. Because PDGFRβ does not bind the PDGF-A chain with high affinity, PDGF-AA activates only αα receptor dimers, whereas PDGF-AB and PDGF-CC activates αα and αβ receptor heterodimers.

BRIEF SUMMARY OF THE INVENTION

This invention relates to treatment of primary and metastatic bone tumors, including tumors that originate from prostate, breast, or lung and express insulin-like growth factor-I receptor (IGF-IR) and/or the alpha platelet derived growth factor receptor (PDGFRα).

The tumors to be treated can be hormone/androgen-dependent or hormone/androgen independent, and can have originated, for example, from prostate, breast, or lung.

The invention provides methods of treating a subject having a bone tumor, and methods of inhibiting growth of a bone tumor. The methods comprise administering an effective amount of an IGF-IR antagonist or an effective amount of a PDGFRα antagonist. The receptor antagonists include antibodies and antibody fragments as well as intracellular small molecule inhibitors.

The invention provides anti-IGF-IR or anti-PDGFRα antibodies that bind to their target receptor and inhibit ligand binding. The invention also provides antibodies and other antagonists that neutralize activation of IGF-IR or PDGFRα. Further certain antibodies promotes down-regulation of their target receptor, for example by internalization and/or degradation. Accordingly, the antibodies and small molecule antagonists function to inhibit activation of downstream signaling molecules such as Akt, p42/p44, and MAPK.

The methods include use of IGF-IR or PDGFRα antagonists alone, in combination with each other or in combination with other cancer therapeutics, such as chemotherapeutics and radiation.

The invention also provides antibodies and antibody fragments that bind to PDGFRα as well as nucleotides and host cell for production of the antibodies. The antibodies block ligand binding and neutralize receptor activation. The invention also provides for use of the antibodies alone, in combination with other receptor antagonists or antineoplastic agents, or as conjugates for treatment of neoplastic disease. Anti-PDGFRα antibodies are used to treat, for example, ovarian tumors, breast tumors, lung tumors, hepatocellular tumors, gastrointestinal stromal tumors, melanomas, renal cell carcinomas, prostate tumors, and soft tissue sarcomas.

DETAILED DESCRIPTION OF THE INVENTION

Figure 1:
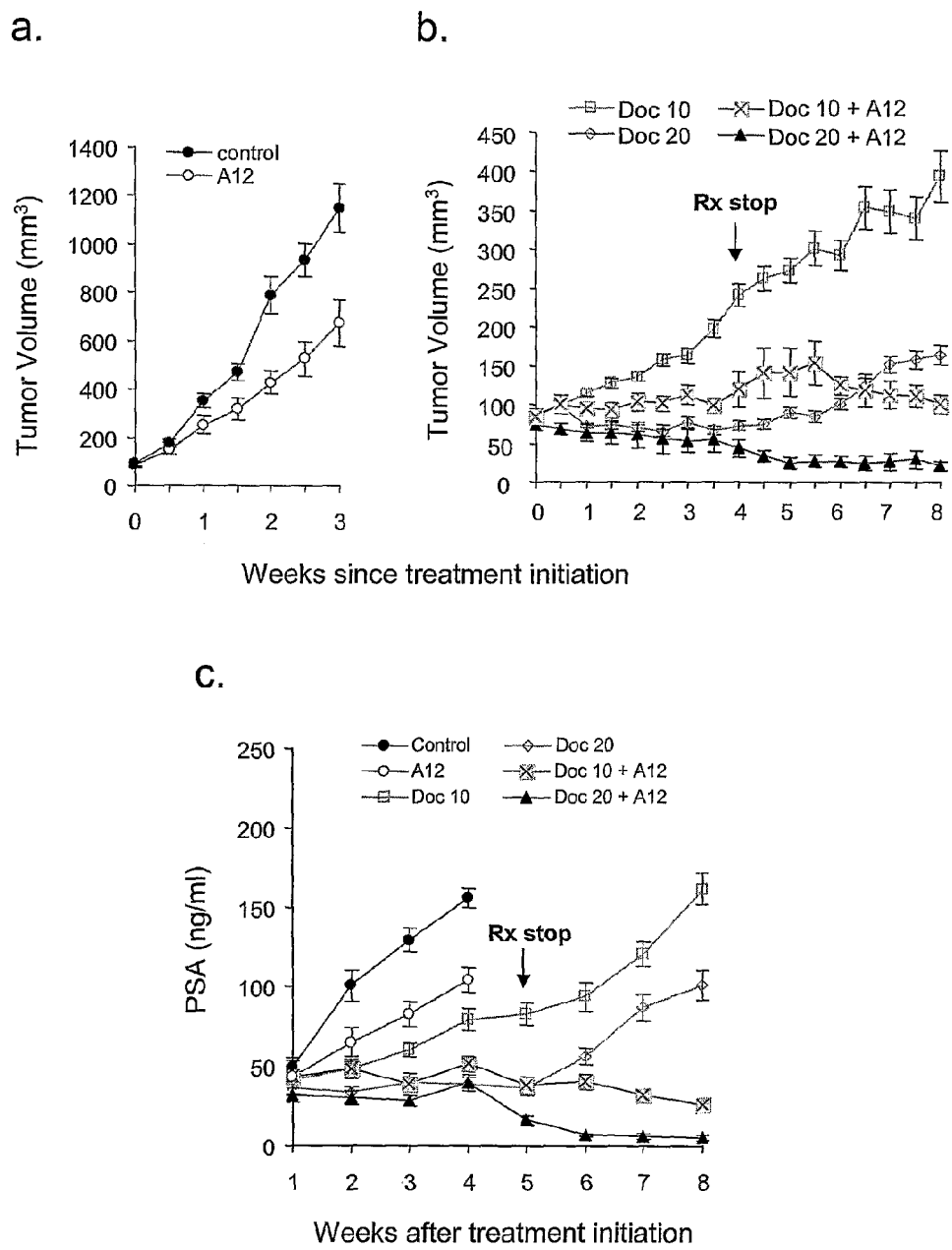
FIG. 1 depicts growth of LuCaP 35V subcutaneous xenograft tumors in castrated SCID mice during a treatment period initiated when the tumors had reached 150-200 mm$^3$. Panel A: untreated controls; Panel B: animals were treated for four weeks with docetaxel (either 10 mg/kg or 20 mg/kg) alone, or in combination with anti-IGF-IR antibodies (40 mg/kg IMC-A12); Panel C: serum PSA levels in untreated and treated SOD mice carrying subcutaneous LuCaP 35V xenograft tumors. Treated mice received docetaxel (20 mg/kg) alone or docetaxel (either 10 mg/kg or 20 mg/kg) in combination with anti-IGF-IR antibodies (40 mg/kg IMC-A12). Treatment was initiated when tumors had reached 150-200 mm$^3$ and terminated after four weeks.

The present invention relates to treatment of bone tumors with antibodies or antibody fragments that bind to insulin-like growth factor-I receptor (IGF-IR). Endocrine expression of IGF-I is regulated primarily by growth hormone and produced in the liver, but other tissue types are also capable of expressing IGF-I, including bone which contains a large store of growth factors. Depending on tumor cell type, IGF-I is involved in endocrine, paracrine, and/or autocrine regulation (Yu, H. and Rohan, *J. Natl. Cancer Inst.* 92:1472-89 (2000)).

It has been discovered that antibodies that bind IGF-IR are useful in therapies for treatment of bone tumors that express IGF-IR. The antibodies can be use alone, or in combination with other cancer therapeutics, particularly chemotherapeutics. Anti-IGF-IR therapy, alone or in combination with therapy with one or more anti-neoplastic agents (such as, for example, chemotherapy or radiation therapy) has significant therapeutic efficacy. Suppression of tumor growth is often accompanied with an increase in apoptosis and persists after all treatment is discontinued and tumors have again begun to grow in animals treated with chemotherapy alone.

It has also been discovered that PDGFRα plays an important role in growth of bone tumors. For example, certain tumor cell lines that express PDGFRα preferentially metastasize to bone. Such cell lines display increased PDGFRα activation and phosphorylation of downstream signaling molecules in response to soluble factors present in bone marrow. PDGFRα activation by bone marrow is reduced or completely inhibited by PDGFRα antagonists, and phosphorylation of downstream signaling molecules that are commonly activated by signaling through PDGFRα and other receptor tyrosine kinase systems is greatly reduced. Certain data suggest that the PI3K/Akt survival pathway is activated by PDGFRα signaling not only by ligands that activate PDGFRα directly, but also by factors present in bone marrow that cause transactivation of the receptor.

Primary bone tumors to be treated according to the invention include, but are not limited to, osteosarcomas, chondrosarcomas, fibrosarcomas, and hemangiosarcomas. Notably, malignant secondary (metastatic) tumors are far more common than primary bone tumors. Metastatic bone tumors to be treated according to the invention can arise from a variety of sources, the most common of which are cancers of the prostate, breast, or lung. The source of a metastatic bone cancer will usually be apparent from a patients history. The tumors can be osteoblastic or osteolytic. The tumors may be dependent on IGF-IR stimulation when they arise, or may transition to IGF-IR dependence. For example, prostate cancers or metastases of prostate cancers that are initially hormone/androgen dependent and controllable by physical or chemical treatments that suppress androgen or hormone production, may become hormone/androgen-independent through increased sensitivity to stimulation through IGF-IR. Further, in addition to providing for treatment of hormone/androgen-independent tumors, the invention can be useful for treating hormone/androgen-dependent bone tumors without reliance on suppression of androgen or hormone production, for example, by coadministering IGF-IR antibodies with anti-neoplastic agents. Such tumors would include metastatic bone tumors that are stimulated through IFG-IR in the IGF-rich environment of the bone, which may be sensitive to hormone stimulation but not sensitive enough to grow without IGF involvement. Hormone ablation might not be necessary for such tumors.

Bone tumors that are PDGF-dependent can also be treated according to the invention, as well as tumors that are "bone marrow" dependent. Bone marrow dependent tumors display PDGFRα activation in response to soluble factors present in bone marrow. For example, as exemplified herein, a human metastatic PDGFRα-expressing cancer cell line undergoes PDGFRα activation and Akt+ phosphorylation upon exposure to bone marrow aspirate. An anti-PDGFRα antibody and a small molecule PDGFRα antagonist each inhibit PDGFRα activation and Akt+ phosphorylation in the cell line. Soluble bone marrow factors that activate PDGFRα include, but are not limited to, PDGF-AA and -BB.

While such bone marrow dependence involves signaling through PDGFRα, it may not involve only binding of PDGFRα of a PDGFRα ligand. For example, as exemplified herein, it is noted that PDGFRα activation by defined ligands (PDGF-AA or -BB) is weaker than activation by bone marrow aspirate. Further, it is observed that in the presence of bone marrow aspirate, Akt+ phosphorylation diminishes with increased incubation time. Taken together, these results suggest that besides responding to binding of PDGFs, PDGFRα may be transactivated (phosphorylated) by other signal transduction elements (e.g., other receptor tyrosine kinases) sensitive to other bone marrow components. In any event, in a cell line suited for metastatic growth in bone (i.e., a cell line that preferentially metastasizes to bone), bone marrow-dependent PDGFRα activation is observed, which is inhibited by PDGFRα antagonists. Further, treatment with a PDGFRα antagonist inhibits bone marrow induced stimulation of the PI3K/Akt anti-apoptotic pathway and mitogen-activated protein kinase (MAPK).

Bone tumors to be treated with a PDGFRα antagonist can arise as metastases of prostate cancer cells, and, as above, may be hormone/androgen dependent, or have transitioned to hormone/androgen independence. Such tumors can arise as metastases of non-prostate cancers as well. One skilled in the art would easily be able to diagnose such conditions and disorders using known, conventional tests.

Treatment means any treatment of a disease in an animal and includes: (1) preventing the disease from occurring in a mammal which may be predisposed to the disease but does not yet experience or display symptoms of the disease; e.g., prevention of the outbreak of the clinical symptoms; (2) inhibiting the disease, e.g., arresting its development; or (3) relieving the disease, e.g., causing regression of the symptoms of the disease. Inhibiting tumor growth includes slowing or stopping growth, as well as causing tumor regression. An effective amount for the treatment of a disease means that amount which, when administered to a mammal in need thereof, is sufficient to effect treatment, as defined above, for that disease. IGF-IR antagonists and PDGFRα antagonist of the invention may be administered alone, in combination with one another, or in combination with one or more antineoplastic agents such as, for example, a chemotherapeutic or radologic agent.

In an embodiment of the invention, it may be desirable to determine the level of expression of IGF-IR and/or PDGFRα in a tumor to be treated. In such cases, tumor biopsies can be collected and analyzed by methods well known in the art. In another embodiment of the invention, an IGF-IR antagonist or PDGFRα antagonist is administered on the basis that the corresponding receptor is commonly expressed or activated in a particular tumor type or invariably becomes expressed of activated as the disease progresses.

An IGF-IR antagonist can be an extracellular antagonist or an intracellular antagonist and more than one antagonist may be employed. Extracellular antagonists include, but are not limited to proteins or other biological molecules that bind to IGF-IR or one or more of its ligands (e.g, IGF-I and IGF-II are natural ligands of IGF-IR). In an embodiment of the invention, an extracellular antagonist inhibits binding of IGF-IR to its ligands. In one embodiment, the antagonist is an anti-IGF-IR antibody, such as, for example, IMC-A12. In another embodiment, the antagonist is a soluble ligand binding fragment of IGF-IR. Intracellular IGF-IR antagonists can be biological molecules, but are usually small molecules. Examples include, but are not limited to, tyrosine kinase inhibitor AG1024 (Calbiochem), insulin-like growth factor-I receptor kinase inhibitor NVP-AEW541 (Novartis), and insulin-like growth factor-I/insulin receptor inhibitor BMS-554417 (Bristol Myers Squibb). It will be appreciated that useful small molecule to be used in the invention are inhibitors of IGF-IR, but need not be completely specific for IGF-IR.

Anti-IGF-IR antibodies to be used according to the present invention exhibit one or more of following properties:

1) The antibodies bind to the external domain of IGF-IR and inhibit binding of IGF-I or IGF-II to IGF-IR. Inhibition can be determined, for example, by a direct binding assay using purified or membrane bound receptor. In this embodiment, the antibodies of the present invention, or fragments thereof, preferably bind IGF-IR at least as strongly as the natural ligands of IGF-IR (IGF-I and IGF-II).

2) The antibodies neutralize IGF-IR. Binding of a ligand, e.g., IGF-I or IGF-II, to an external, extracellular domain of IGF-IR stimulates autophosphorylation of the beta subunit and downstream signaling molecules, including MAPK, Akt, and IRS-1.

Neutralization of IGF-IR includes inhibition, diminution, inactivation and/or disruption of one or more of these activities normally associated with signal transduction. Neutralization can be determined in vivo, ex vivo, or in vitro using, for example, tissues, cultured cell, or purified cellular components. Neutralization includes inhibition of IGF-IR/IR heterodimers as well as IGF-IR homodimers. Thus, neutralizing IGF-IR has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

One measure of IGF-IR neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a western blot. Some assays for tyrosine kinase activity are described in Panek et al., *J. Pharmacol. Exp. Thera.* 283: 1433-44 (1997) and Batley et al., *Life Sci.* 62:143-50 (1998). Antibodies of the invention cause a decrease in tyrosine phosphorylation of IGF-IR of at least about 75%, preferably at least about 85%, and more preferably at least about 90% in cells that respond to ligand.

Another measure of IGF-IR neutralization is inhibition of phosphorylation of downstream substrates of IGF-IR. Accordingly, the level of phosphorylation of MAPK, Akt, or IRS-1 can be measured. The decrease in phosphorylation is at least about 40%, and can be at least about 60%, or at least about 80%.

In addition, methods for detection of protein expression can be utilized to determine IGF-IR neutralization, wherein the proteins being measured are regulated by IGF-IR tyrosine kinase activity. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., *Cancer,* 78:1284-92 (1996); Shimizu et al., *Japan J. Cancer Res.,* 85:567-71 (1994); Sauter et al., *Am. J. Path.,* 148:1047-53 (1996); Collins, *Glia* 15:289-96 (1995); Radinsky et al., *Clin. Cancer Res.* 1:19-31 (1995); Petrides et al., *Cancer Res.* 50:3934-39 (1990); Hoffmann et al., *Anticancer Res.* 17:4419-26 (1997); Wikstrand et al., *Cancer Res.* 55:3140-48 (1995).

Ex vivo assays can also be utilized to determine IGF-IR neutralization. For example, receptor tyrosine kinase inhibition can be observed by mitogenic assays using cell lines stimulated with receptor ligand in the presence and absence of inhibitor. The MCF7 breast cancer line (American Type Culture Collection (ATCC), Rockville, Md.) is such a cell line that expresses IGF-IR and is stimulated by IGF-I or IGF-II. Another method involves testing for inhibition of growth of IGF-IR-expressing tumor cells or cells transfected to express IGF-IR. Inhibition can also be observed using tumor models, for example, human tumor cells injected into a mouse.

The antibodies of the present invention are not limited by any particular mechanism of IGF-IR neutralization. The anti-IGF-IR antibodies of the present invention can bind externally to the IGF-IR cell surface receptor, block binding of ligand (e.g., IGF-I or IGF-II) and subsequent signal transduction mediated via the receptor-associated tyrosine kinase, and prevent phosphorylation of the IGF-IR and other downstream proteins in the signal transduction cascade.

3) The antibodies down modulate IGF-IR. The amount of IGF-IR present on the surface of a cell depends on receptor protein production, internalization, and degradation. The amount of IGF-IR present on the surface of a cell can be measured indirectly, by detecting internalization of the receptor or a molecule bound to the receptor. For example, receptor internalization can be measured by contacting cells that express IGF-IR with a labeled antibody. Membrane-bound antibody is then stripped, collected and counted. Internalized antibody is determined by lysing the cells and detecting label in the lysates.

Another way is to directly measure the amount of the receptor present on the cell following treatment with an anti-IGF-IR antibody or other substance, for example, by fluorescence-activated cell-sorting analysis of cells stained for surface expression of IGF-IR. Stained cells are incubated at 37° C. and fluorescence intensity measured over time. As a control, part of the stained population can be incubated at 4° C. (conditions under which receptor internalization is halted).

Cell surface IGF-IR can be detected and measured using a different antibody that is specific for IGF-IR and that does not block or compete with binding of the antibody being tested. (Burtrum, et al. *Cancer Res.* 63:8912-21 (2003)) Treatment of an IGF-IR expressing cell with an antibody of the invention results in reduction of cell surface IGF-IR. In a preferred embodiment, the reduction is at least about 70%, more preferably at least about 80%, and even more preferably at least about 90% in response to treatment with an antibody of the invention. A significant decrease can be observed in as little as four hours.

Another measure of down-modulation is reduction of the total receptor protein present in a cell, and reflects degradation of internal receptors. Accordingly, treatment of cells (particularly cancer cells) with antibodies of the invention results in a reduction in total cellular IGF-IR. In a preferred embodiment, the reduction is at least about 70%, more preferably at least about 80%, and even more preferably at least about 90%.

For treatment of human subjects, antibodies according to the invention are preferably human. Alternatively, the antibodies can be from non-human primates or other mammals, or be humanized or chimeric antibodies. In an embodiment of the invention, an anti-IGF-IR antibody comprises one, two, three, four, five, and/or six complementarity determining regions (CDRs) selected from the group consisting of SEQ ID NO:35, SEQ ID NO:37, SEQ ID NO:39, SEQ ID NO:45, SEQ ID NO:47, and SEQ ID NO:49 (CDR1H, CDR2H, CDR3H, CDR1L, CDR2L, CDR3L, respectively). In another embodiment, the anti-IGF-IR antibody comprises one, two, three, four, five, and/or six complementarity determining regions (CDRs) selected from the group consisting of SEQ ID NO:35, SEQ ID NO:37, SEQ ID NO:39, SEQ ID NO: 55, SEQ ID NO:57, and SEQ ID NO:59 (CDR1H, CDR2H, CDR3H, CDR1L, CDR2L, CDR3L, respectively). Preferably, the antibodies (or fragments thereof) of the present invention have heavy chain CDRs of SEQ ID NO:35, SEQ ID NO:37 and SEQ ID NO:39. Alternatively and also preferably, the present antibodies including fragments thereof, have light chain CDRs of SEQ ID NO:45, SEQ ID NO:47 and SEQ ID NO:49 or SEQ ID NO:55, SEQ ID NO:57 and SEQ ID NO:59. One such anti-IGF-IR antibody is the human IgG1 antibody IMC-A12 (WO2005016970), having a heavy chain variable domain represented by SEQ ID NO:41 and a light chain variable domain represented by SEQ ID NO:51. Another preferred human antibody is IMC-2F8 (WO2005016970), having a heavy chain variable domain identical to IMC-A12 and a light chain variable domain represented by SEQ ID NO:61. Useful antibodies further include anti-IGF-IR antibodies that compete with IMC-A12 or IMC-2F8 for binding to IGF-IR, as well as antibodies that bind to other epitopes (i.e., antibodies that bind to other epitopes and exhibit properties as previously described such as ligand blocking, receptor internalization, etc., but do not compete with IMC-A12 or IMC-2F8).

According to the invention, PDGFRα antagonists can also be used for treatment. A PDGFRα antagonist can be an extracellular antagonist or an intracellular antagonist and more than one antagonist may be employed. Extracellular antagonists include, but are not limited to proteins or other biological molecules that bind to PDGFRα or one or more of its ligands (e.g, PDGF-AA, -AB, -BB, -CC). In an embodiment of the invention, an extracellular antagonist is inhibits binding of PDGFRα to its ligands. In one embodiment, the antagonist is an anti-PDGFRα antibody, such as, for example, IMC-3G3. In another embodiment, the binding protein is a soluble ligand binding fragment of PDGFRα. Intracellular IGF-IR antagonists can be biological molecules, but are usually small molecules. In one embodiment, the intracellular PDGFRα antagonist is AG1296. AG1296 (Calbiochem) is an inhibitor of PDGFα, PDGFβs, and c-KIT, and also reacts with Flt3. Other small molecules that target PDGFRs include STI-571 (imatinib mesylate, Gleevec®, Novartis) and SU11248 (sunitinib malate, SUTENT®, Pfizer).

In an embodiment of the invention, an anti-PDGFRα antibody comprises one, two, three, four, five, and/or six complementarity determining regions (CDRs) selected from the group consisting of SEQ ID NO:2, SEQ ID NO:4, SEQ ID NO:6, SEQ ID NO:10, SEQ ID NO:12, and SEQ ID NO:14 (CDR1H; CDR2H, CDR3H, CDR1L, CDR2L, CDR3L, respectively). Preferably, the antibodies (or fragments thereof) of the present invention have CDRs of SEQ ID NO:2, SEQ ID NO:4 and SEQ ID NO:6. Alternatively and also preferably, the present antibodies, or fragments thereof, have CDRs of SEQ ID NO:10, SEQ ID NO:12 and SEQ ID NO:14. The amino acid sequences of the CDRs are set forth below in Table 1.

TABLE 1

CDRs of IMC-3G3

Heavy Chain

| CDR1 | SSSYY | SEQ ID NO: 2 |
| CDR2 | SFFYTGSTYYNPSLRS | SEQ ID NO: 4 |
| CDR3 | QSTYYYGSGNYYGWFDR | SEQ ID NO: 6 |

Light Chain

| CDR1 | RASQSVSSYLA | SEQ ID NO: 10 |
| CDR2 | DASNRAT | SEQ ID NO: 12 |
| CDR3 | QQRSNWPPA | SEQ ID NO: 14 |

In another embodiment, the anti-PDGFRα antibody, or fragment thereof, has a human heavy chain variable region of SEQ ID NO:8 and/or a human light chain variable region of SEQ ID NO:16. IMC-3G3 is such an antibody and is exemplified in the present invention.

Preferably, the antibodies, or fragments thereof, of the present invention neutralize PDGFRα. Binding of a ligand, e.g., PDGF-AA, PDGF-AB, PDGF-BB or PDGF-CC, to an extracellular domain of PDGFRα stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. The anti-PDGFRα antibodies typically block ligand binding and/or receptor dimerization, and inhibit one or more of autophosphorylation, activation of tyrosine kinase activity and signal transduction. The anti-PDGFRα antibodies of the present invention can be specific for the extracellular ligand binding region of PDGFRα and prevent binding of a ligand of PDGFRα. Preferably, such anti-PDGFRα antibodies, or fragments thereof, bind PDGFRα at least as strongly as the natural ligands of PDGFRα. Alternatively or additionally, the antibodies can be specific for a region of the receptor monomer that would otherwise form a receptor dimer interface. Such antibodies block dimer formation, though ligand binding to a receptor monomer might or might not be blocked.

As described above for anti-IGF-IR antibodies, receptor neutralization can be determined by a variety of in vivo, in vitro, and ex vivo methods. In one embodiment of the invention, the anti-PDGFRα antibodies reduce phosphorylation of PDGFRα by at least about 75%. In other embodiments, phosphorylation is reduced by at least about 85% or at least about 90%. In an embodiment of the invention, as a result of inhibition of PDGFRα signal transduction, phosphorylation or a downstream signal transduction pathway component (e.g., Akt, p42/p44, etc.) is reduced by at least about 40%, at least about 60%, or at least about 80%. Receptor neutralization can be determined using defined ligands (e.g., PDGF-AA, -AB, -BB, -CC), mixtures of such ligands, or preparations such as bone marrow aspirates that comprise PDGFs as well as other stimulatory growth factors.

Neutralization of PDGFRα includes inhibition, diminution, inactivation and/or disruption of one or more of these activities normally associated with signal transduction. Thus, neutralizing PDGFRα has various effects, including inhibition, diminution, inactivation and/or disruption of growth (proliferation and differentiation), angiogenesis (blood vessel recruitment, invasion, and metastasis), and cell motility and metastasis (cell adhesion and invasiveness).

Ex vivo assays, as described above, can also be utilized to determine PDGFRα neutralization. For example, human SKLMS-1 leiomyosarcoma cells (American Type Culture Collection (ATCC), Rockville, Md.; ATCC HTB-88™) or U118 glioblastoma cells (ATCC HTB-15™) stimulated with PDGF-AA can be used to assay PDGFRα inhibition. Growth inhibition can be ascertained using PDGFRα-expressing human tumor cells injected into a SCID mouse.

The present invention is not limited by any particular mechanism of PDGFRα neutralization. The anti-PDGFRα antibodies of the present invention bind externally to the PDGFRα cell surface receptor, block binding of ligand (e.g., PDGF-AA, PDGF-AB, PDGF-BB, PDGF-CC), inhibit phosphorylation of the PDGFRα, inhibit signal transduction mediated via the receptor-associated tyrosine kinase, and modulate activity of downstream signal transduction components. The receptor-antibody complex can also be internalized and degraded, resulting in cell surface receptor down-regulation. Matrix metalloproteinases, which function in tumor cell invasion and metastasis, can also be downregulated by the antibodies of the present invention. Moreover, antibodies of the present invention may exhibit inhibition of growth factor production and angiogenesis.

As described above, PDGFRα antagonists of the invention are useful for treating bone tumors, including metastatic bone tumors. Other tumor types that express PDGFRα and can be treated according to the invention include, but are not limited to, ovarian tumors, breast tumors, lung tumors, hepatocellular tumors, gastrointestinal stromal tumors, melanoma, renal cell carcinoma, prostate tumors, and soft tissue sarcomas. Soft tissue sarcomas originate in such tissues as fat, muscles, nerves, tendons, and blood and lymph vessels. Typically, the tumor cells overexpress PDGFRα. PDGFRα expression can be determined, for example, by histochemistry or RNA analysis. For example, a scatchard analysis of binding of radiolabeled IMC-3G3 to U118 cells and SKLMS-1 tumor cells indicates the number of PDGFRα molecules on the cells to be about 500 and 2500, respectively.

PDGFRα antagonists function by inhibiting signal transduction by PDGFRα expressed on the tumor cells themselves, or by inhibiting PDGFRα expressed on surrounding stromal cells that otherwise undergo paracrine stimulation by PDGFs expressed from tumor cells. Thus, antibodies such as IMG-3G3 and other PDGFRα antagonists are useful for treating tumors characterized by autocrine and/or paracrine stimulation of PDGFRα.

Antibody fragments according to the invention can be produced by cleaving a whole antibody, or by expressing DNA that encodes the fragment. Fragments of antibodies may be prepared by methods described by Lamoyi et al., *J. Immunol. Methods,* 56: 235-243 (1983) and by Parham, *J. Immunol.* 131: 2895-2902 (1983). Such fragments may contain one or both Fab fragments or the F(ab')$_2$ fragment. Such fragments may also contain single-chain fragment variable region antibodies, i.e. scFv, dibodies, or other antibody fragments. Methods of producing such functional equivalents are disclosed in PCT Application WO 93/21319, European Patent Application No. EP 239400; PCT Application WO 89/09622; European Patent Application EP 338745; and European Patent Application EP 332424.

Preferred host cells for transformation of vectors and expression of the antibodies of the present invention are mammalian cells, e.g., COS-7 cells, Chinese hamster ovary (CHO) cells, and cell lines of lymphoid origin such as lymphoma, myeloma (e.g. NS0), or hybridoma cells. Other eukaryotic hosts, such as yeasts, can be alternatively used.

Where it is desired to express a gene construct in yeast, a suitable selection gene for use in yeast is the trp1 gene present in the yeast plasmid YRp7. Stinchcomb et al. *Nature,* 282: 39 (1979); Kingsman et al., *Gene,* 7: 141 (1979). The trp1 gene provides a selection marker for a mutant strain of yeast lacking the ability to grow in tryptophan, for example, ATCC No. 44076 or PEP4-1. Jones, *Genetics,* 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

The transformed host cells are cultured by methods known in the art in a liquid medium containing assimilable sources of carbon (carbohydrates such as glucose or lactose), nitrogen (amino acids, peptides, proteins or their degradation products such as peptones, ammonium salts or the like), and inorganic salts (sulfates, phosphates and/or carbonates of sodium, potassium, magnesium and calcium). The medium furthermore contains, for example, growth-promoting substances, such as trace elements, for example iron, zinc, manganese and the like.

High affinity anti-PDGFRα and anti-IGF-IR antibodies according to the present invention can be isolated from a phage display library constructed from human heavy chain and light chain variable region genes. For example, a variable domain of the invention can be obtained from a peripheral blood lymphocyte that contains a rearranged variable region gene. Alternatively, variable domain portions, such as CDR and FW regions, can be obtained from different sources and recombined. Further, portions of the variable domains (e.g., FW regions) can be synthetic consensus sequences.

Antibodies and antibody fragments of the present invention can be obtained, for example, from naturally occurring antibodies, or Fab or scFv phage display libraries. It is understood that, to make a single domain antibody from an antibody comprising a $V_H$ and a $V_L$ domain, certain amino acid substitutions outside the CDRs can be desired to enhance binding, expression or solubility. For example, it can be desirable to modify amino acid residues that would otherwise be buried in the $V_H$-$V_L$ interface.

Further, antibodies and antibody fragments of the invention can be obtained by standard hybridoma technology (Harlow & Lane, ed., Antibodies: A Laboratory Manual, Cold Spring Harbor, 211-213 (1998), which is incorporated by reference herein) using transgenic mice (e.g., KM mice from Medarex, San Jose, Calif.) that produce human immunoglobulin gamma heavy and kappa light chains. In a preferred embodiment, a substantial portion of the human antibody producing genome is inserted into the genome of the mouse, and is rendered deficient in the production of endogenous murine antibodies. Such mice may be immunized subcutaneously (s.c.) with PDGFRα (usually in complete Freund's adjuvant) with boosts as needed. Immunization methods are well known in the art.

The protein used to identify IGF-IR binding antibodies of the invention is preferably IGF-IR and, more preferably, is the extracellular domain of IGF-IR. The protein used to identify PDGFRα binding antibodies of the invention is preferably PDGFRα and, more preferably, is the extracellular domain of PDGFRα. Such extracellular domains can be free or conjugated to other molecules.

The present invention also provides isolated polynucleotides encoding the antibodies, or fragments thereof, described previously. Details of the IMC-A12 anti-IGF-IR antibody are disclosed in WO2005016970. Table 2 sets forth the nucleic acid sequences for IMC-3G3.

TABLE 2

Nucleotide sequences encoding CDRs of IMC-3G3

Heavy Chain

```
CDR1  agtagtagtt actac                                            SEQ ID NO: 1
CDR2  agtttctttt atactgggag cacctactac aacccgtccc tcaggagt        SEQ ID NO: 3
CDR3  cagtccacgt attactatgg ttcggggaat tattatggct ggttcgaccg c    SEQ IS NO: 5
```

Light Chain

```
CDR1  agggccagtc agagtgttag cagctactta gcc                        SEQ ID NO: 9
CDR2  gatgcatcca acagggccac t                                     SEQ ID NO: 11
CDR3  cagcagcgta gcaactggcc tccggcg                               SEQ ID NO: 13
```

DNA encoding human antibodies can be prepared by recombining DNA encoding human constant regions and variable regions, other than the CDRs, derived substantially or exclusively from the corresponding human antibody regions and DNA encoding CDRs derived from a human (SEQ ID NOS:1, 3, and 5 for the heavy chain variable domain CDRs and SEQ ID NOS:9, 11, and 13 for the light chain variable domain CDRs).

Suitable sources of DNAs that encode fragments of antibodies include any cell, such as hybridomas and spleen cells, that express the full-length antibody. The fragments may be used by themselves as antibody equivalents, or may be recombined into equivalents, as described above. The DNA deletions and recombinations described in this section may be carried out by known methods, such as those described in the publications listed above with regard to equivalents of antibodies and/or other standard recombinant DNA techniques, such as those described below. Another source of DNAs are single chain antibodies produced from a phage display library, as is known in the art.

Additionally, the present invention provides expression vectors containing the polynucleotide sequences previously described operably linked to an expression sequence, a promoter and an enhancer sequence. A variety of expression vectors for the efficient synthesis of antibody polypeptide in prokaryotic, such as bacteria and eukaryotic systems, including but not limited to yeast and mammalian cell culture systems have been developed. The vectors of the present invention can comprise segments of chromosomal, non-chromosomal and synthetic DNA sequences.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. An example of a vector useful in yeast is the 2μ plasmid. Suitable vectors for expression in mammalian cells include well-known derivatives of SV40, adenovirus, retrovirus-derived DNA sequences and shuttle vectors derived from combination of functional mammalian vectors, such as those described above, and functional plasmids and phage DNA.

Additional eukaryotic expression vectors are known in the art (e.g., P. J. Southern and P. Berg, J. Mol. Appl. Genet., 1, 327-341 (1982); Subramani et al., Mol. Cell. Biol., 1: 854-864 (1981); Kaufmann and Sharp, "Amplification And Expression of Sequences Cotransfected with a Modular Dihydrofolate Reductase Complementary DNA Gene," J. Mol. Biol. 159, 601-621 (1982); Kaufmann and Sharp, Mol. Cell. Biol. 159, 601-664 (1982); Scahill et al., "Expression And Characterization Of The Product Of A Human Immune Interferon DNA Gene In Chinese Hamster Ovary Cells," Proc. Nat'l Acad. Sci. USA 80, 4654-4659 (1983); Urlaub and Chasin, Proc. Nat'l Acad. Sci. USA 77, 4216-4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The present invention also provides recombinant host cells containing the expression vectors previously described. Antibodies of the present invention can be expressed in cell lines other than in hybridomas. Nucleic acids, which comprise a sequence encoding a polypeptide according to the invention, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, NS0 cells, Chinese Hamster Ovary (CHO) cells, Baby Hamster Kidney (BHK) cells and many others. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCI, *Pseudomonas, Bacillus*, such as *Bacillus subtilis*, and *Streptomyces*.

These present recombinant host cells can be used to produce an antibody, or fragment thereof, by culturing the cells under conditions permitting expression of the antibody or fragment thereof and purifying the antibody or fragment thereof from the host cell or medium surrounding the host cell. Targeting of the expressed antibody or fragment for secretion in the recombinant host cells can be facilitated by inserting a signal or secretory leader peptide-encoding sequence (see, Shokri et al., Appl Microbiol Biotechnol. 60(6):654-64 (2003), Nielsen et al., Prot. Eng. 10:1-6 (1997) and von Heinje et al., Nucl. Acids Res. 14:4683-4690 (1986)) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The antibodies of this invention can be fused to additional amino acid residues. Such amino acid residues can be a peptide tag, perhaps to facilitate isolation. Other amino acid residues for homing of the antibodies to specific organs or tissues are also contemplated.

In another embodiment, an antibody of the present invention is made by expressing a nucleic acid encoding the antibody in a transgenic animal, such that the antibody is expressed and can be recovered. For example, the antibody can be expressed in a tissue specific manner that facilitates recovery and purification. In one such embodiment, an antibody of the invention is expressed in the mammary gland for secretion during lactation. Transgenic animals, include but are not limited to mice, goat, and rabbit.

Antibodies that can be used according to the invention include complete immunoglobulins, antigen binding fragments of immunoglobulins, as well as antigen binding proteins that comprise antigen binding domains of immunoglobulins. Antigen binding fragments of immunoglobulins include, for example, Fab, Fab', and F(ab')$_2$. Other antibody formats have been developed which retain binding specificity, but have other characteristics that may be desirable, including for example, bispecificity, multivalence (more than two binding sites), compact size (e.g., binding domains alone).

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one $V_H$ and one $V_L$ domain covalently linked by a first peptide linker, can be covalently linked by at least one or more peptide linker to form a multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of amino acid residues is about one hundred.

Two single chain antibodies can be combined to form a diabody, also known as a bivalent dimer. Diabodies have two chains and two binding sites, and can be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a $V_L$ or $V_H$ domain directly fused to the carboxyl terminus of a $V_L$ or $V_H$ domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Thus, antibodies of the invention and fragments thereof include, but are not limited to, naturally occurring antibodies, bivalent fragments such as (Fab)$_2$, monovalent fragments such as Fab, single chain antibodies, single chain Fv (scFv), single domain antibodies, multivalent single chain antibodies, diabodies, triabodies, and the like that bind specifically with antigens.

The anti-IGF-IR and anti-PDGFRα antibodies or antibody fragments, which may be internalized upon binding to cells bearing IGF-IR (WO2005016970) or PDGFRα, can be chemically or biosynthetically linked to anti-tumor agents. Anti-tumor agents linked to such an antibody include any agents which destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods (See, e.g., Hermentin and Seiler, *Behring Inst. Mitt.* 82:197-215 (1988)).

Suitable radioisotopes for use as anti-tumor agents are also known to those skilled in the art. For example, $^{131}$I or $^{211}$At is used. These isotopes are attached to the antibody using conventional techniques (See, e.g., Pedley et al., *Br. J. Cancer* 68, 69-73 (1993)).

Alternatively, the anti-tumor agent which is attached to the antibody is an enzyme which activates a prodrug. In this way, a prodrug is administered which remains in its inactive form until it reaches the target site where it is converted to its cytotoxin form. In practice, the antibody-enzyme conjugate is administered to the patient and allowed to localize in the region of the tissue to be treated. The prodrug is then administered to the patient so that conversion to the cytotoxic drug occurs in the region of the tissue to be treated.

Other anti-tumor agents include cytokines such as interleukin-2 (IL-2), interleukin-4 (IL-4) or tumor necrosis factor alpha (TNF-α). The antibody targets the cytokine to the tumor so that the cytokine mediates damage to or destruction of the tumor without affecting other tissues. The cytokine can be conjugated to the antibody at the DNA level using conventional recombinant DNA techniques.

In certain embodiments of the invention, anti-IGF-IR or anti-PDGFRα antibodies are administered in combination with one or more anti-neoplastic agents. For examples of combination therapies, see, e.g., U.S. Pat. No. 6,217,866 (Schlessinger et al.) (Anti-EGFR antibodies in combination with anti-neoplastic agents); WO 99/60023 (Waksal et al.) (Anti-EGFR antibodies in combination with radiation). Any suitable anti-neoplastic agent can be used, such as a chemotherapeutic agent, radiation or combinations thereof. The anti-neoplastic agent can be an alkylating agent or an anti-metabolite. Examples of alkylating agents include, but are not limited to, cisplatin, cyclophosphamide, melphalan, and dacarbazine. Examples of anti-metabolites include, but not limited to, doxorubicin, daunorubicin, and paclitaxel, gemcitabine.

Useful anti-neoplastic agents also include mitotic inhibitors, such as taxanes docetaxel and paclitaxil. Topoisomerase inhibitors are another class of anti-neoplastic agents that can be used in combination with antibodies of the invention. These include inhibitors of topoisomerase I or topoisomerase II. Topoisomerase I inhibitors include irinotecan (CPT-11), aminocamptothecin, camptothecin, DX-8951f, topotecan. Topoisomerase II inhibitors include etoposide (VP-16), and teniposide (VM-26). Other substances are currently being evaluated with respect to topoisomerase inhibitory activity and effectiveness as anti-neoplastic agents. In a preferred embodiment, the topoisomerase inhibitor is irinotecan (CPT-11).

In an particular embodiment of the invention, an anti-IGF-IR antibody is administered in combination with docetaxel. In another embodiment of the invention, an anti-PDGFRα antibody is administered in combination with doxorubicin.

When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity tumor being treated and the route of administration of the agent. It should be emphasized, however, that the present invention is not limited to any particular dose.

The antibody (anti-IGF-IR or anti-PDGFRα) and antibody plus anti-neoplastic agent treatments can also be used for patients who receive adjuvant hormonal therapy (e.g., for breast cancer) or androgen-deprivation therapy (e.g., for prostate cancer).

Anti-IGF-IR and anti-PDGFRα antagonists of the invention can be coadministered, or administered with receptor antagonists that neutralize other receptors involved in tumor growth or angiogenesis. For example in an embodiment of the invention, an anti-IGF-IR antibody and an anti-PDGFRα antibody are coadministered. In one embodiment, in which a target tumor cell expresses both IGF-IR and PDGFRα, common signal transduction elements are activated by signal transduction through each receptor. Although inhibition of one receptor will generally result in decreased activation of the common downstream components, inhibition of both receptors will decrease activation further. In another embodiment, certain cells in a tumor or surrounding tissue express significant amounts of one receptor, and other cells express significant amounts of the second receptor. Coadministration of the antagonists reduces growth of the tumor cell and paracrine stimulation of surrounding cells.

A bispecific antibody can be provided as an alternative to coadministration. A variety of bispecific antibodies exist that are designed to incorporate various desirable characteristic. For example, bispecific diabodies have minimal size. Bispecific antibodies with four antigen binding sites (two for each binding specificity) have binding avidities that are similar to those of corresponding natural antibodies. Certain bispecific antibodies incorporate Fc regions, thus retaining effector functions (e.g., complement dependent cytoxicity (CDC) and antibody dependent cellular cytoxicity (ADCC)) of natural antibodies. WO 01/90192 describes IgG-like tetravalent antibodies WO2006/020258 describes a tetravalent antibody that incorporates two diabodies and retains effector functions.

In another embodiment, an anti-IGF-IR antibody or an anti-PDGFRα antibody or other antagonist is used in combination with a receptor antagonist that binds specifically to an epidermal growth factor receptor (e.g., EGFR, Her2/erbB2, erbB3, erbB4). Particularly preferred are antigen-binding proteins that bind to the extracellular domain of EGFR and block binding of one or more of its ligands and/or neutralize ligand-induced activation of EGFR. EGFR antagonists also include antibodies that bind to a ligand of EGFR and inhibits binding of EGFR to its ligand. Ligands for EGFR include, for example, EGF, TGF-α, amphiregulin, heparin-binding EGF (HB-EGF) and betacellulin. EGF and TGF-α are thought to be the main endogenous ligands that result in EGFR-mediated stimulation, although TGF-α has been shown to be more potent in promoting angiogenesis. EGFR antagonists also include substances that inhibit EGFR dimerization with other EGFR receptor subunits (i.e., EGFR homodimers) or heterodimerization with other growth factor receptors (e.g., HER2). EGFR antagonists further include biological molecules and small molecules, such as synthetic kinase inhibitors that act directly on the cytoplasmic domain of EGFR to inhibit EGFR-mediated signal transduction. Erbitux® (cetuximab) is an example of an EGFR antagonist that binds to EGFR and blocks ligand binding. One example of a small molecule EGFR antagonist is IRESSA™ (ZD1939), which is a quinozaline derivative that functions as an ATP-mimetic to inhibit EGFR. See U.S. Pat. No. 5,616,582 (Zeneca Limited); WO 96/33980 (Zeneca Limited) at p. 4; see also, Rowinsky et al., Abstract 5 presented at the 37th Annual Meeting of ASCO, San Francisco, Calif., 12-15 May 2001; Anido et al., Abstract 1712 presented at the 37th Annual Meeting of ASCO, San Francisco, Calif., 12-15 May 2001. Another example of a small molecule EGFR antagonist is Tarceva® (OSI-774), which is a 4-(substituted phenylamino)quinozaline derivative [6,7-Bis(2-methoxy-ethoxy)-quinazolin-4-yl]-(3-ethynyl-phenyl)amine hydrochloride] EGFR inhibitor. See WO 96/30347 (Pfizer Inc.) at, for example, page 2, line 12 through page 4, line 34 and page 19, lines 14-17. See also Moyer et al., *Cancer Res.*, 57: 4838-48 (1997); Pollack et al., *J. Pharmacol.*, 291: 739-48 (1999). Tarceva® may function by inhibiting phosphorylation of EGFR and its downstream PI3/Akt and MAP (mitogen activated protein) kinase signal transduction pathways resulting in p27-mediated cell-cycle arrest. See Hidalgo et al., Abstract 281 presented at the 37th Annual Meeting of ASCO, San Francisco, Calif., 12-15 May 2001.

Other small molecules are also reported to inhibit EGFR, many of which are thought to be specific to the tyrosine kinase domain of an EGFR. Some examples of such small molecule EGFR antagonists are described in WO 91/116051, WO 96/30347, WO 96/33980, WO 97/27199 (Zeneca Limited). WO 97/30034 (Zeneca Limited), WO 97/42187 (Zeneca Limited), WO 97/49688 (Pfizer Inc.), WO 98/33798 (Warner Lambert Company), WO 00/18761 (American Cyanamid Company), and WO 00/31048 (Warner Lambert Company). Examples of specific small molecule EGFR antagonists include Cl-1033 (Pfizer), which is a quinozaline (N-[4-(3-chloro-4-fluoro-phenylamino)-7-(3-morpholin-4-yl-propoxy)-quinazolin-6-yl]-acrylamide) inhibitor of tyrosine kinases, particularly EGFR and is described in WO 00/31048 at page 8, lines 22-6; PKI166 (Novartis), which is a pyrrolopyrimidine inhibitor of EGFR and is described in WO 97/27199 at pages 10-12; GW2016 (GlaxoSmithKline), which is an inhibitor of EGFR and HER2; EKB569 (Wyeth), which is reported to inhibit the growth of tumor cells that overexpress EGFR or HER2 in vitro and in vivo; AG-1478 (Tryphostin), which is a quinazoline small molecule that inhibits signaling from both EGFR and erbB-2; AG-1478 (Sugen), which is a bisubstrate inhibitor that also inhibits protein kinase CK2; PD 153035 (Parke-Davis) which is reported to inhibit EGFR kinase activity and tumor growth, induce apoptosis in cells in culture, and enhance the cytotoxicity of cytotoxic chemotherapeutic agents; SPM-924

(Schwarz Pharma), which is a tyrosine kinase inhibitor targeted for treatment of prostate cancer; CP-546,989 (OSI Pharmaceuticals), which is reportedly an inhibitor of angiogenesis for treatment of solid tumors; ADL-681, which is a EGFR kinase inhibitor targeted for treatment of cancer; PD 158780, which is a pyridopyrimidine that is reported to inhibit the tumor growth rate of A4431 xenografts in mice; CP-358,774, which is a quinzoline that is reported to inhibit autophosphorylation in HN5 xenografts in mice; ZD1839, which is a quinzoline that is reported to have antitumor activity in mouse xenograft models including vulvar, NSCLC, prostrate, ovarian, and colorectal cancers; CGP 59326A, which is a pyrrolopyrimidine that is reported to inhibit growth of EGFR-positive xenografts in mice; PD 165557 (Pfizer); CGP54211 and CGP53353 (Novartis), which are dianilnophthalimides. Naturally derived EGFR tyrosine kinase inhibitors include genistein, herbimycin A, quercetin, and erbstatin.

Further small molecules reported to inhibit EGFR and that are therefore within the scope of the present invention are tricyclic compounds such as the compounds described in U.S. Pat. No. 5,679,683; quinazoline derivatives such as the derivatives described in U.S. Pat. No. 5,616,582; and indole compounds such as the compounds described in U.S. Pat. No. 5,196,446.

Another receptor that can be targeted along with IGF-IR or PDGFRα is a vascular endothelial growth factor receptor (VEGFR). In an embodiment of the present invention, an anti-IGF-IR antibody or anti-PDGFRα antibody is used in combination with a VEGFR antagonist. In one embodiment, an antagonist is used that binds specifically to VEGFR-1/Flt-1 receptor. In another embodiment, the VEGFR antagonist binds specifically to VEGFR-2/KDR receptor. Particularly preferred are antigen-binding proteins that bind to the extracellular domain of VEGFR-1 or VEGFR-2 and block binding by their ligands (VEGFR-2 is stimulated most strongly by VEGF; VEGFR-1 is stimulated most strongly by PIGF, but also by VEGF) and/or neutralize ligand-induced induced activation. For example, IMC-1121 is a human antibody that binds to and neutralizes VEGFR-2 (WO 03/075840; Zhu). Another example is MAb 6.12 that binds to soluble and cell surface-expressed VEGFR-1. ScFv 6.12 comprises the $V_L$ and $V_H$ domains of mouse monoclonal antibody MAb 6.12. A hybridoma cell line producing MAb 6.12 has been deposited as ATCC number PTA-3344 under the provisions of the Budapest Treaty on the International Recognition of the Deposit of Microorganisms for the Purposes of Patent Procedure and the regulations thereunder (Budapest Treaty). In another embodiment, the VEGFR antagonist binds to a VEGFR ligand and blocks activation of a VEGFR by the ligand. For example, Avastin® (bevacizumab) is an antibody that binds VEGF.

Other examples of growth factor receptors involved in tumorigenesis are nerve growth factor (NGFR), and fibroblast growth factor (FGFR).

In an additional alternative embodiment, the anti-IGF-IR and anti-PDGFRα antibodies or can be administered in combination with one or more suitable adjuvants, such as, for example, cytokines (IL-10 and IL-13, for example) or other immune stimulators, such as, but not limited to, chemokine, tumor-associated antigens, and peptides. See, e.g., Larrivée et al., supra. It should be appreciated, however, that administration of only an anti-IGF-IR or anti-PDGFRα antibody is sufficient to prevent, inhibit, or reduce the progression of the tumor in a therapeutically effective manner.

In a combination therapy, the anti-IGF-IR or anti-PDGFRα antibody is administered before, during, or after commencing therapy with another agent, as well as any combination thereof, i.e., before and during, before and after, during and after, or before, during and after commencing the anti-neoplastic agent therapy. For example, the antibody antibody can be administered between 1 and 30 days, preferably 3 and 20 days, more preferably between 5 and 12 days before commencing radiation therapy. In a preferred embodiment of the invention, chemotherapy is administered concurrently with or, more preferably, subsequent to antibody therapy.

In the present invention, any suitable method or route can be used to administer antibodies of the invention, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

One of skill in the art would understand that dosages and frequency of treatment depend on the tolerance of the individual patient and on the pharmacological and pharmacokinetic properties of blocking or inhibitory agent used. Ideally, one wishes to achieve saturable pharmacokinetics for the agent used. A loading dose for both the anti-IGF-IR and anti-PDGFRα antibodies can range, for example, from about 10 to about 1000 mg/m$^2$, preferably from about 200 to about 400 mg/m$^2$. This can be followed by several additional daily or weekly dosages ranging, for example, from about 200 to about 400 mg/m$^2$. The patient is monitored for side effects and the treatment is stopped when such side effects are severe.

One of skill in the art would also know how to monitor the progress of the treatment in order to determine an effective dose. For bone metastases from prostate cancer, one such way is to monitor PSA levels. Other ways to monitor bone metastases include bone scans and MRI.

For patients for which cancer-treatment-induced bone loss (CTIBL) is a risk or problematic (e.g., patients who receive adjuvant hormonal therapy for breast cancer or androgen-deprivation therapy for prostate cancer), the any aforementioned treatment may be supplemented by administration of agents for prevention of CTIBL, such as bisphosphonates. Bisphosphonates include, for example, clodronate, risedronate, and zoledronic acid.

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

The following examples further illustrate the invention, but should not be construed to limit the scope of the invention in any way. Detailed descriptions of conventional methods, such as those employed in the construction of vectors and plasmids, and expression of antibodies and antibody fragments can be obtained from numerous publications, including Sambrook, J et al., (1989) Molecular Cloning: A Laboratory Manual, $2^{nd}$ ed., Cold Spring Harbor Laboratory Press; Coligan, J. et al. (1994) Current Protocols in Immunology, Wiley & Sons, Incorporated; Enna, S. J. et al. (1991) Current Protocols in Pharmacology, Wiley & Sons, Bonifacino, J. S. et al. (1999) Current Protocols in Cell Biology, Wiley & Sons. All references mentioned herein are incorporated in their entirety.

EXAMPLES

Example 1

Effects of IMC-A12 and Docetaxel on Tumor Growth

Tumor bits (20 to 30 mm$^3$) of androgen-independent (AI) LuCaP 35V were implanted subcutaneously (s.c.) into 32 six-week-old castrated SCID mice respectively as previously described (4). When the implanted tumor was observed to reach a volume of 150-200 mm$^3$, animals were randomized into four groups for treatment studies. Group 1 animals received docetaxel treatment at a dose of 20 mg/kg. Group 2 animals received docetaxel treatment at a dose of 10 mg/kg. Group 3 animals received combined treatment of 10 mg/kg docetaxel and 40 mg/kg A12. Group 4 animals received combined treatment of 20 mg/kg docetaxel and 40 mg/kg A12. All treatments were administered intraperitoneally (ip). Docetaxel was administered once a week. A12 was administered three times a week. All animals were treated for four weeks and monitored for additional four weeks before euthanization. Tumors were measured twice weekly and tumor volume was estimated by the formula: volume=L×W$^2$/2. Following our University of Washington IACUC approved animal protocol, some animals were euthanized at an earlier time when tumor reached a volume of 1000 mm$^3$ or when animal weight loss exceeded 20% of initial body weight. Animals were weighed twice a week. Blood samples were collected from orbital sinus weekly. Serum was separated and PSA level was determined using the IMx Total PSA Assay (Abott Laboratories, Abott Park, Ill.). BrdU was injected into the tumors 1 h before the animals were euthanized for evaluation of in vivo tumor cell proliferation rate.

After euthanization, tumors were collected and halved. A portion of the tumors were fixed in 10% neutral buffer formalin (NFB) and embedded in paraffin. Five micron sections were prepared for immunohistochemistry (IHC) staining. The remaining portion of the tumors was separated into single cells mechanically by mincing and filtering through 70 µm nylon sieves.

As shown in FIG. 1, LuCaP 35V xenograft grew aggressively in mice at an average growth rate of 362.0±72.0 mm$^3$/week without any treatment. All animals in the non-treated group had to be sacrificed within three weeks after treatment initiation in experimental groups, due to tumor volume exceeds 1000 mm$^3$. When animals were treated with 40 µg/kg A12 alone, tumor growth rate was reduced to 192.7±35.6 mm$^3$/week during treatment. When docetaxel was given to the animals at a dose of 10 mg/kg, LuCaP 35V tumor growth rate was reduced to an average of 29.6±6.1 mm$^3$/week. When docetaxel was given in combination with A12 treatment, LuCaP 35V tumor growth rate was further reduced to an average of 7.9±10 mm$^3$/week (FIG. 1b). The inhibition effect of docetaxel combined with A12 persisted for over four weeks after the termination of treatments. When a higher dose of docetaxel (20 mg/kg) was given to the animals, regardless with or without combined A12 treatment, tumor volume did not increase during the four-week treatment period; in contrast, a tendency of reduced tumor volumes was observed. However, in the four-weeks following the treatment termination, reduction of tumor volumes was continued in the group of animals treated with docetaxel combined with A12. In contrast, tumor volumes were increasing at an average rate of 27.0±16.1 mm$^3$/week in the group of animals treated with docetaxel alone. These results have suggested that, in a given dose of docetaxel, combined treatment with A12 can enhance the inhibitory effect of docetaxel on tumor growth during treatment or after treatment follow-ups.

PSA is a commonly used clinical parameter to assess prostate tumor growth. Serum PSA levels were measured in animals during and after the treatments. As shown in FIG. 1c, in animals treated with A12 and docetaxel or 20 mg/kg docetaxel alone, no significant change was seen in serum levels of PSA during the four-week treatment, consistent with the suppressed tumor growth. After treatment termination, serum PSA level was shown increased in animals treated with docetaxel alone and, in contrast, to be consistent or even decreased in animals treated with docetaxel in combination with A12. These data are consistent with continued post-treatment inhibition of tumor growth in animals treated with docetaxel and A12.

Induction of Apoptosis by Docetaxel Combined with Anti-IGF-IR Antibody.

The combined in vivo effect of docetaxel and A12 treatment on cell cycle and cell survival at the experimental end point was measured by terminal deoxynucleotidyl transferase-mediated nick end labeling (TUNEL) assay and propidium (PI) staining using the Apop-Direct kit (BD Bio-Science) as previously described. Briefly, 1×10$^6$ cells from the single-cell suspension were fixed with 10% neutral buffer formalin (NBF) followed by 70% ethanol alcohol at −20° C. for 30 min. After several washes, cells were permeabilized with 0.1% Triton X-100 and incubated with FITC-conjugated dUTP and terminal deoxynucleotidyl transferase enzyme (TdT) at 37° C. for 1 h, followed by an incubation with PI/RNase buffer (100 µg/ml of PI, 50 µg/ml RNase) at room temperature for 60 min. Samples were analyzed by flow cytometry using a BD FACscan. Data were analyzed with CellQuest$^{PRO}$ software.

Figure 2:
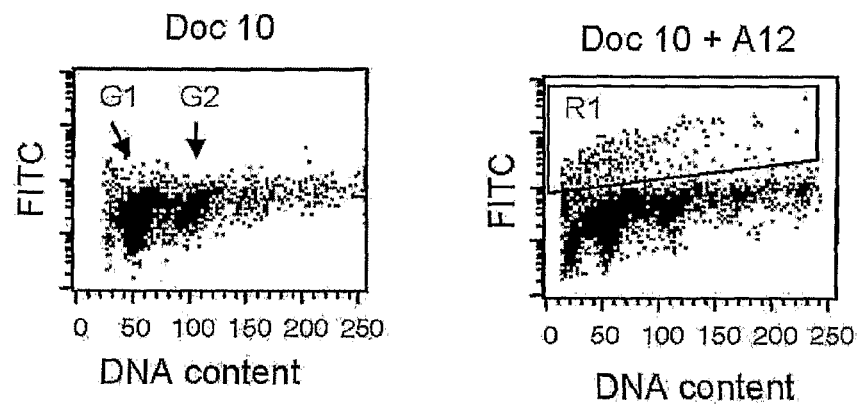
FIG. 2 shows single cell suspensions of LuCaP 35V xenograft tumors treated with docetaxel (10 mg/kg) alone (Panel A) or in combination with anti-IGF-IR antibodies (40 mg/kg IMC-A12) (Panel B). The field labeled R1 corresponds to apoptotic cells with fragmented DNA (increased FITC labeling).

Four weeks after treatment termination, apoptosis was detected in a significant percentage of tumors from animals that had been treated with docetaxel (66.7% in 10 mg/kg docetaxel treated group and 77.8% in 20 mg/kg docetaxel treated group) in combination with A12 (FIG. 2b and Table 1), regardless of the dosage of docetaxel being used. The average apoptotic events in these tumors occurred at a rate of 15.0±4.3%. No apoptosis in tumors was detected in animals that were treated with docetaxel alone. Instead, a majority (88% in 10 mg/kg docetaxel treated group and 100% in 20 mg/kg docetaxel treated group) of the tumors proceeded to normal cell cycle (FIG. 2a and Table 3).

TABLE 3

Tumor cell cycle and survival activities at time of sacrifice

| Treatment | Apoptosis (%) | G1 arrest (%) | G2 arrest (%) | Normal cycle (%) |
|---|---|---|---|---|
| None | 0 | 0 | 0 | 100 |
| Doc (20) | 0 | 0 | 0 | 100 |
| Doc (20) + A12 | 66.7 | 33.3 | 0 | 0 |
| Doc (10) | 0 | 0 | 12 | 88 |
| Doc (10) + A12 | 77.8 | 0 | 0 | 12.2 |

To further evaluate tumor cell proliferation ability after different treatment termination, paraffin-section of stained with anti-BrDu antibody. Tumor samples were fixed in 10% NBF, embedded in paraffin, and sectioned at 5-μm onto slides. After deparaffinization and rehydration, antigens were retrieved with 0.01 M citric acid (pH 6.0) at 95° C. for 2×5 min. Slides were allowed to cool for 30 min, followed by sequential rinsing with PBS. Endogenous peroxidase activity was quenched by an incubation with 0.3% $H_2O_2$ in methanol for 15 min. After blocking with 1.5% normal goat serum in PBS containing 0.05% Tween 20 (PBST) for 1 h, slides were incubated with mouse anti-BrdU antibody (1 μg/ml) for 1 h followed by sequential incubation with biotinylated goat anti-mouse IgG for 30 min, peroxidase-labeled avidin for 30 min (Santa Cruz Biotechnology) and diaminobenzidine (DAB)/hydrogen peroxide chromogen substrate (Vector Laboratories, Burlingame, Calif.) for 5-10 min. All incubation steps were performed at room temperature. Slides were counterstained with hematoxylin (Sigma), and mounted with permount (Fisher Scientific, Fair Lawn, N.J.). For negative control, mouse IgG (Vector Laboratories) was used instead of the primary anti-BrdU antibody. Slides were examined under a Zeiss Microscope and digital images were obtained. Numbers of BrdU-labeled nucleus and total nucleus were collected from 10 random views of each section. Proliferation index was calculated by the number of BrdU-positive nuclei divided by the total number of nuclei. Ten fields were counted per slide. H&E stained were performed by using hematoxylin and eosin (Richard Allen, Kalamazoo, Mich.).

Figure 3:
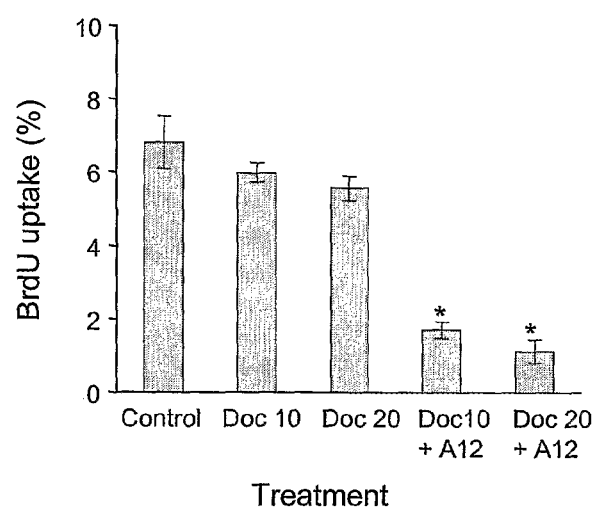
FIG. 3 shows DNA synthesis (BrDu uptake) in tumor xenografts following termination of treatment with docetaxel (10 mg/kg or 20 mg/kg) alone, and in combination with anti-IGF-IR antibodies (40 mg/kg IMC-A12).

In animals that were treated with docetaxel and A12, BrDu uptake was significantly less than those treated with the same dose of docetaxel alone (FIG. 3). These data of BrDu incorporation are consistent with the above observations of cell cycle and apoptosis, suggesting that A12 significant enhanced the cytotoxicity of docetaxel.

Differential Regulation of Gene Expression in Tumors Treated with Docetaxel Combined with Anti-IGF-IR Antibody Vs. Docetaxel Alone.

To determine potential mechanisms for the markedly enhanced effect of docetaxel by A12, IGF-IR expression was examined in all harvested tumors by immunohistochemistry and flow cytometry analysis. There was no difference in surface IGF-IR expression among all the treatment groups or compared to the control group (data not shown). Post-treatment gene expression was examined using cDNA microarray analyses in tumors from animals that had received 20 mg/kg of docetaxel and 20 mg/kg of docetaxel combined with A12. Based on SAM analyses, 49 genes were identified as differentially expressed in tumors that received combined treatment of docetaxel and A12 compared to those received docetaxel alone, with more than 2-fold change and less than 10% false discovery rate (FDR) (data not shown). Thirteen genes were identified that are potentially involved in regulation of apoptosis or cell cycle (Table 4). All 13 genes were at least 2-fold different between the two treatments and had a FDR of less than 0.02%. Nine genes were down-regulated and four genes were up-regulated in tumors treated with docetaxel and A12, as compared to tumors treated with docetaxel alone.

TABLE 4

Post-treatment differential gene expression in tumors treated with docetaxel + A12 compared to tumors treated with docetaxel alone.

| HUGO | Name | GO Function | Fold Change | FDR |
|---|---|---|---|---|
| Down-regualted genes | | | | |
| CDC2 | Cell division cycle 2 | cytokinesis; mitosis; | 3.0 | ≤0.02% |
| CDC6 | CDC6 cell division cycle 6 homolog | negative regulation of cell proliferation | 2.2 | ≤0.02% |
| CCNA2 | Cyclin A2 | regulation of CDK activity | 2.1 | ≤0.02% |
| MYBL2 | V-myb myeloblastosis viral oncogene homolog (avian)-like 2 | anti-apoptosis; development; regulation of cell cycle; | 3.2 | ≤0.02% |
| TUBB | Tubulin beta polypeptide | microtubule-based movement taxane resistance | 2.3 | ≤0.02% |
| K-ALPHA-1 | Tubulin alpha ubiquitous | microtubule-based movement taxane resistance | 2.5 | ≤0.02% |
| BIRC5 | Baculoviral IAP repeat-containing 5 (survivin) | anti-apoptosis | 2.5 | ≤0.02% |
| CDC25B | Cell division cycle 25B | positive regulation of cell proliferation | 2.0 | ≤0.02% |
| MYC | V-myc myelocytomatosis viral oncogene homolog (avian) | cell cycle arrest; | 2.5 | ≤0.02% |
| Up-regulated genes | | | | |
| TOB1 | Transducer of ERBB21 | negative regulation of cell proliferation | 2.2 | ≤0.02% |
| CCNG2 | Cyclin G2 | cell cycle checkpoint | 2.1 | ≤0.02% |
| IGFBP3 | Insulin-like growth factor binding protein 3 | regulation of cell growth, pro-apoptotic | 2.0 | ≤0.02% |
| BIRC3 | Baculoviral IAP repeat-containing 3 | anti-apoptosis; cell surface receptor linked signal transduction | 2.2 | ≤0.02% |

Figure 4:
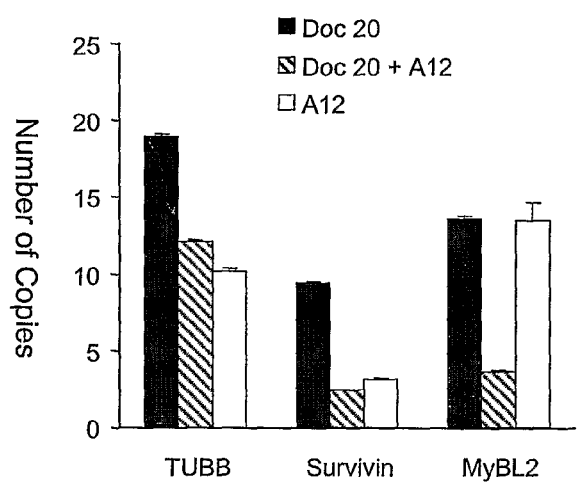
FIG. 4 depicts differential expression of genes associated with prostate tumor aggressiveness (TUBB), resistance to antiandrogen therapy (BIRC 5), and apoptosis induction (IGFBP3) in prostate tumor cells in response to treatment with docetaxel and A12 and docetaxel alone.

For selected genes, the results were confirmed by real-time RT-PCR. A standard PCR fragment of target cDNA was purified. A series of dilutions of the standards from 10 ng/μl to 10 pg/μl were used for real-time RT-PCR to generate standard curves. One μg of total RNA from each group of pooled tumor was used for first-strand cDNA synthesis using Superscript First Strand Synthesis System (Invitrogen). Real-time RT-PCR was performed in 20 μl of reaction mixture containing 1 μl of first strand of cDNA, specific primers sets, and Lightcycler FastStart DNA Master Plus SYBR Green using a Roche Lightcycler following the manufacturer's protocol (Roche, Nutley, N.J.). RT-PCR products were subjected to melting curve analysis using Lightcycler software v3.5. The amplicon sizes were confirmed by agarose gel electrophoresis. Each sample was assayed in duplicate. The results are shown in FIG. 4.

Of the down-regulated genes, TUBB has been shown to result in resistance to docetaxel (Tanaka et al., 2004, Int. J. Cancer 111, 617-26), and increased expression of BIRC 5 (survivin) has been shown to be associated with aggressive prostate cancer and resistance to antiandrogen therapy (de Angelis et al., 2004, Int. J. Oncol. 24, 1279-88; Zhang et al., 2005, Oncogene 24, 2474-82) Further, TUBB is an IGF-IR-regulated gene that is involved with IGF-IR mediated transformation (Loughran et al., 2005, Oncogene 24, 6185-93). Of the four up-regulated genes, IGFBP3 has been shown to inhibit IGF-ligand signaling as well as to induce apoptosis in prostate tumor cells in a ligand dependent manner (Grimberg et al., 2000, J. Cell. Physiol. 183, 1-9).

Post-Treatment Serum Levels of A12.

Figure 5:
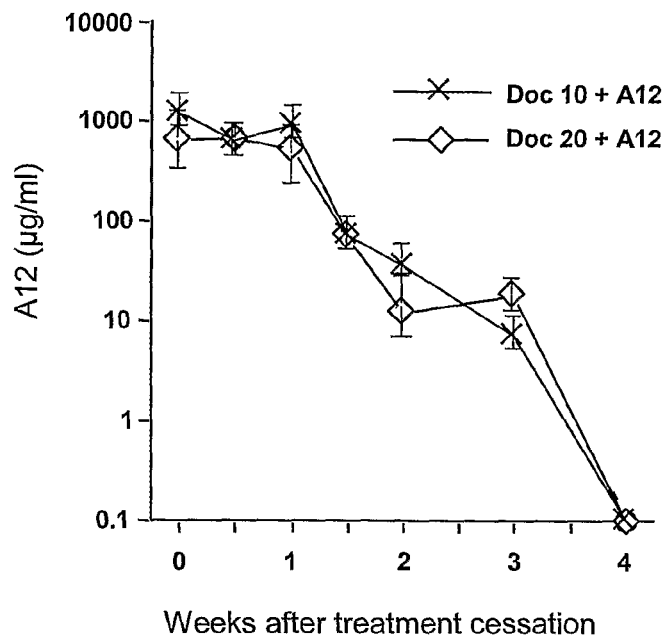
FIG. 5 shows A12 serum levels following cessation of treatment.

Serum levels of A12 were measured in animals that had received docetaxel combined with A12. Serum A12 levels declined 100-fold two weeks after treatment cessation and was detected at a very low level four weeks after treatment cessation (FIG. 5).

Overall Cytotoxicity.

Figure 6:
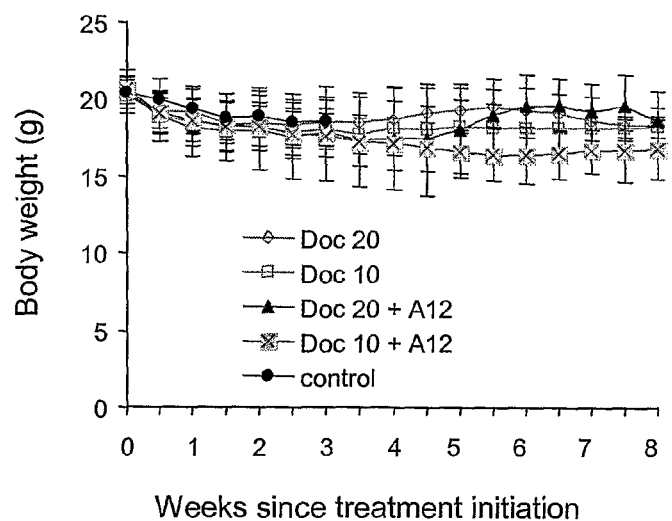
FIG. 6 shows body weight (a measure of overall cytotoxicity) of undiseased animals treated continuously with docetaxel (either 10 mg/kg or 20 mg/kg) alone, or in combination with anti-IGF-IR antibodies (40 mg/kg IMC-A12).

Cytotoxicity of coadministration of docetaxel and IMC-A12 was examined. Although A12 has greater than 95% cross-reactivity with murine IGF-IR, no abnormal daily activity or behavior changes were observed in animals treated with combined reagents or docetaxel alone compared to control tumor-bearing animals. No significant effect on kidney cells was observed in any treatment group by both cell cycle and apoptosis assays (data not shown). No significant change in body weight was observed among the treatment groups (FIG. 6).

Anti-IGF-IR antibody therapy for bone metastases. The effectiveness of treatment with anti-IGF-IR antibodies on metastatic growth of prostate cancer cells in bone was evaluated using prostate cancer cells injected directly into the tibia of SCID mice. By this method, metastatic tumors are established directly without reliance on chemotaxis dependent invasion from the circulation. A variety of tumor lines are available for establishing bone metastases. These include PC-3, LuCaP35, and LnCaP cells which produce osteolytic lesions and LuCaP 23.1 cells which produce osterblastic lesions.

LuCaP 23.1 cells, which express IGF-IR, have a take rate of ~80% in the bone environment and result in osteoblastic reactions. In preliminary experiments, LuCaP 23.1 samples exhibited a significant increase in bone volume vs. tissue volume (% BV/TV) in tumor vs. control tibiae (254-503% of control, p=0.024). All the LuCaP 23.1 tumors in tibiae exhibited new bony trabeculae, which were not present in the normal samples, and a high number of tumor foci, which had replaced the normal bone marrow. In some specimens the tumor and bone growth extended outside the original bone. Increased % BV/TV of LuCaP 23.1 samples was also observed after castration; the % BV/TV of tumored tibiae was 212-354% of that of non-tumored tibiae (p=0.024). The results observed for the intra-tibial xenografts of LuCaP 23.1 are indicative of tumor cell-stimulated de novo bone formation. Further, the tumors show many similarities to human samples of osteoblastic bone metastasis, including large numbers of tumor foci and increased amounts of mineralized bone.

To evaluate the effectiveness of treatment with IMC-A12, LuCaP 23.1 xenograft tumors were engrafted in SCID mice, and serum PSA levels were measured biweekly to evaluate tumor growth. All animals were castrated two weeks prior to tibial tumor cell engraftment. Administration of IMC-A12 to test mice was begun when serum PSA levels reached 5-10 ng/ml (indicating established tumors). 40 mg/kg IMC-A12 was injected i.p. three times a week for six weeks.

Bone mineral density (BMD) of the tumored tibiae and the contralateral tibiae without tumor was measured by Dual X-ray absorptiometry (PIXImus Lunar densitometer) performed on a 2.5 mm×2.5 mm area at the tumor cell injection site, or the corresponding site of the contralateral tibia at the time of engraftment. Biweekly assessment of lesions was made by serum PSA measurements. All animals were sacrificed when the bone lesions in the control group had recurred after castration based on serum PSA levels (LuCaP 35 >60 ng/ml, ng/ml, LuCaP 23.1 >500 ng/ml), radiographical appearance of the bone lesions or when animals became compromised. One hour prior to sacrifice animals were injected with BrdU to monitor tumor cell proliferation. Radiographs were taken prior to sacrifice (FaxitronX-ray MX-20), and BMD of both tibiae were measured at the time of sacrifice.

TABLE 5

Bone mineral density (BMD)

| | Treatment | | | |
|---|---|---|---|---|
| | A12 | | Control | |
| | Tumored Leg | Non-tumored leg | Tumored leg | Non tumored leg |
| Mean | 0.060 | 0.045 | 0.098 | 0.053 |
| P value compared to control tumor | .0057 | | | |
| P value compared to non-tumored leg | .0004 | | .0049 | |

Figure 7:
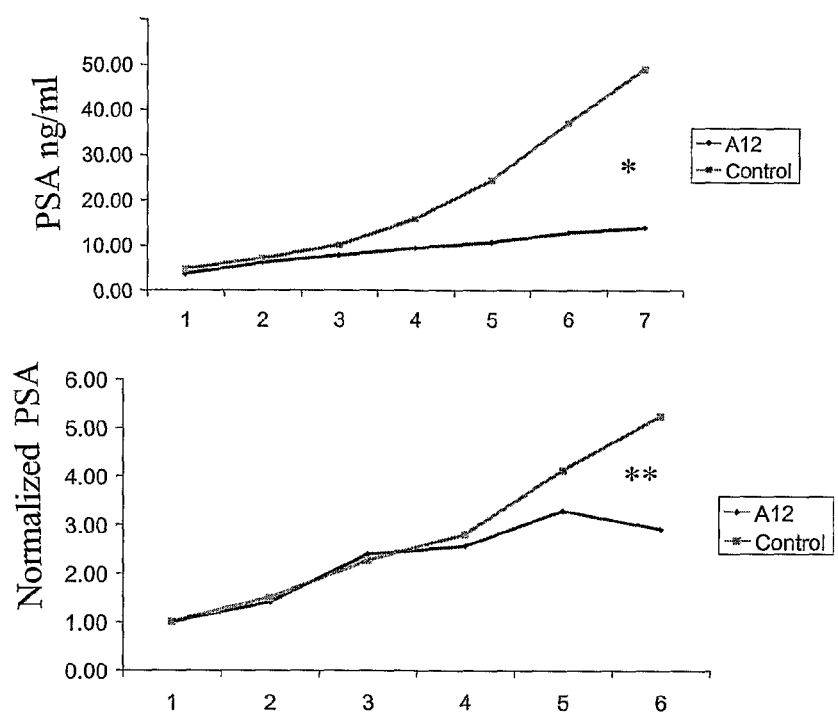
FIG. 7 shows the effect of treatment with an anti-IGF-IR antibody (IMC-A12) on xenograft-produced PSA in SCID mice engrafted with LuCaP 23.1 cells.
Figure 8:
FIG. 8 shows a series of X-ray photographs of SCID mice engrafted with LuCaP 23.1 cells. A12 mice received 40 mg/ml IMC-A12 i.p. three times a week for six weeks. X-ray photographs were made at the time of sacrifice.
Figure 8:
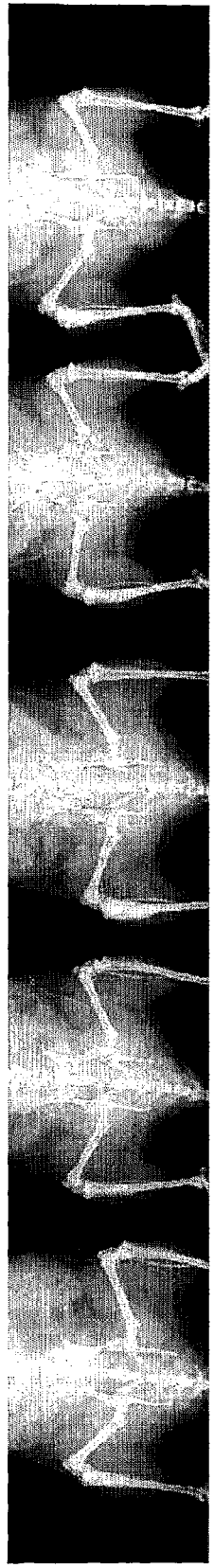

Serum PSA levels were significantly lower in IMC-A12-treated mice (FIG. 7), and the increase in BMD associated with growth of osteoblastic metastatic tumors was significantly reduced as well (Table 5). BMD measurements of the non-tumored legs indicated that IMC-A12 treatment did not cause a loss of bone density (osteoporosis). Radiographs of IMC-A12-treated and untreated mice show that tumor progression was significantly reduced or prevented in treated mice (FIG. 8).

Combination of Anti-IGF-IR Antibody and Docetaxel for Bone Metastases.

SCID mice are castrated 2 weeks prior to tibial tumor injections. Bone metastases are generated by direct injection of LuCaP 23.1 prostate cancer cells into the tibia of the mice, giving rise to osteoblastic lesions. The xenografts express IGF-IR. Serum PSA levels are measured biweekly to evaluate tumor growth. When serum PSA levels reach 5-10 ng/ml indicating established tumor, animals are randomized into four groups.

In two groups, 40 mg/kg of IMC-A12 are injected i.p. three times a week for six weeks with one group receiving IMC-A12+docetaxel 20 mg/kg i.p once a week for 6 weeks and a second group IMC-A12+docetaxel 10 mg i.p. three times a week for 6 weeks. Control groups receive 10 or 20 mg docetaxel i.p. without IMC-A12.

Animals are monitored with weekly PSA measurements. After termination of treatment, animals continue to be monitored with weekly PSA measurements until tumors in the docetaxel only groups show tumor regrowth. As PSA values rise in the docetaxel only groups (albeit at a slower rate that in untreated animals), the PSA levels in the IMC-A12+docataxel-treated mice level off, and in some animals, start to fall. Reductions in PSA levels are observed to continue, even after termination of treatment at six weeks.

As indicated above, BMD measurements are made at the time of engraftment and at sacrifice, and radiographs are taken just prior to sacrifice. The IMC-A12+docataxel-treated groups show little or no increase in BMD, and radiographs show little or no sign of osteoblastic activity.

Combination of Anti-IGF-IR Antibody and Docetaxel for Bone Metastases.

LuCaP 23.1 human prostate tumor bits (20 to 30 mm$^3$) were mechanically digested. 2-5×10$^5$ viable LuCaP 23.1 cells were injected into the tibiae of 6-8 wk old SCID mice. 21 mice randomized into three groups were used for the study. After tumor injection, serum PSA was monitored weekly. Treatment started when serum PSA level reached 5-10 ng/ml, an indication of tumor growth. Group 1 received control vehicle saline buffer. Group 2 received 20 mg/kg of docetaxel i.p once a week for 4 weeks. Group 3 received 20 mg/kg of docetaxel once a week and 40 mg/kg of A12 i.p. three times a week for 4 weeks. To determine whether the response to treatment was osteoblastic or osteolytic, BMD was measured by Dexa-scan and x-rays of the animals at the end point of all treatments.

Figure 9:
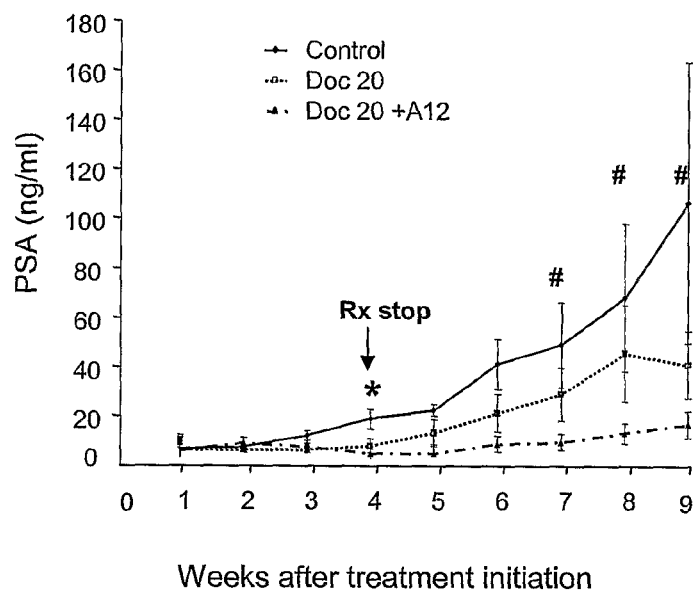
FIG. 9 shows PSA levels (a) and representative radiographs (b) from SCID mice with intratibial xenografts of LuCaP 23.1 human prostate cells.
Figure 9:
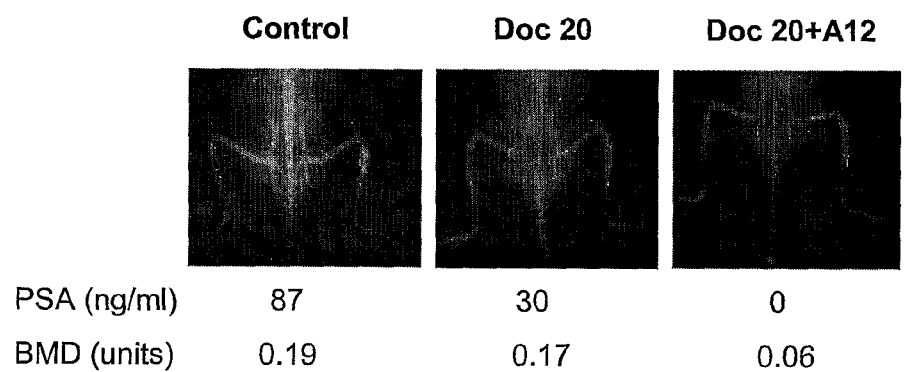

Docetaxel alone or docetaxel combined with A12 significantly inhibited LuCaP 23.1 tumor growth as reflected by suppression of serum PSA levels (FIG. 9a), with no significant difference between the two treatments. However, after treatment cessation, serum PSA began to increase in animals that had been treated with docetaxel alone, indicating a regrowth of the tumor; whereas continued suppression of serum PSA levels were observed in animals that received combined treatment, indicating a prolonged period of post-treatment tumor quiescence. Serum PSA levels were shown to correlate with bone density (BMD) and radiographed tumored bone sizes (FIG. 9b). At week five, the average bone density in the control, docetaxel 20, and docetaxel 20 combined with A12 treated animals was 0.112±0.01, 0.09±0.02, and 0.05±0.009 (mean±SEM), respectively. There was an apparent trend towards a decrease in bone density with treatment.

Example 2

Bone Marrow Aspirate-Induced Akt Phosphorylation

Bone marrow samples from normal male donors (ages 18-45) were supplied by Cambrex (Poietics™ Donor Program). Samples were centrifuged at 1,500 rpm in order to separate the soluble and cellular phases. The supernatant was filtered using 0.8 µm and 0.22 µm filters in succession. 50 µl of bone marrow aspirate was administered to cells in 1 ml of medium (1:20 final dilution).

For experiments performed in the presence of serum, cells were cultured in DMEM supplemented with 10% FBS and 50 µg/ml gentamycin for 24 hours prior to exposure to bone marrow. For experiments in the absence of serum (starved cells), cells were washed twice with PBS, the growth medium was replaced with serum-free DMEM, and the cells were incubated for 4 hours prior to exposure to bone marrow preparations. When used, AG-1296, a specific inhibitor of PDGF receptors (Rice et al., 1999, *Amer. J. Path*. 155, 213-21) was added to cultures 30 min. prior to exposure to bone marrowaspirate. IMC-3G3 antibodies were administered as described at pre-treatment times as stated below.

Figure 10:
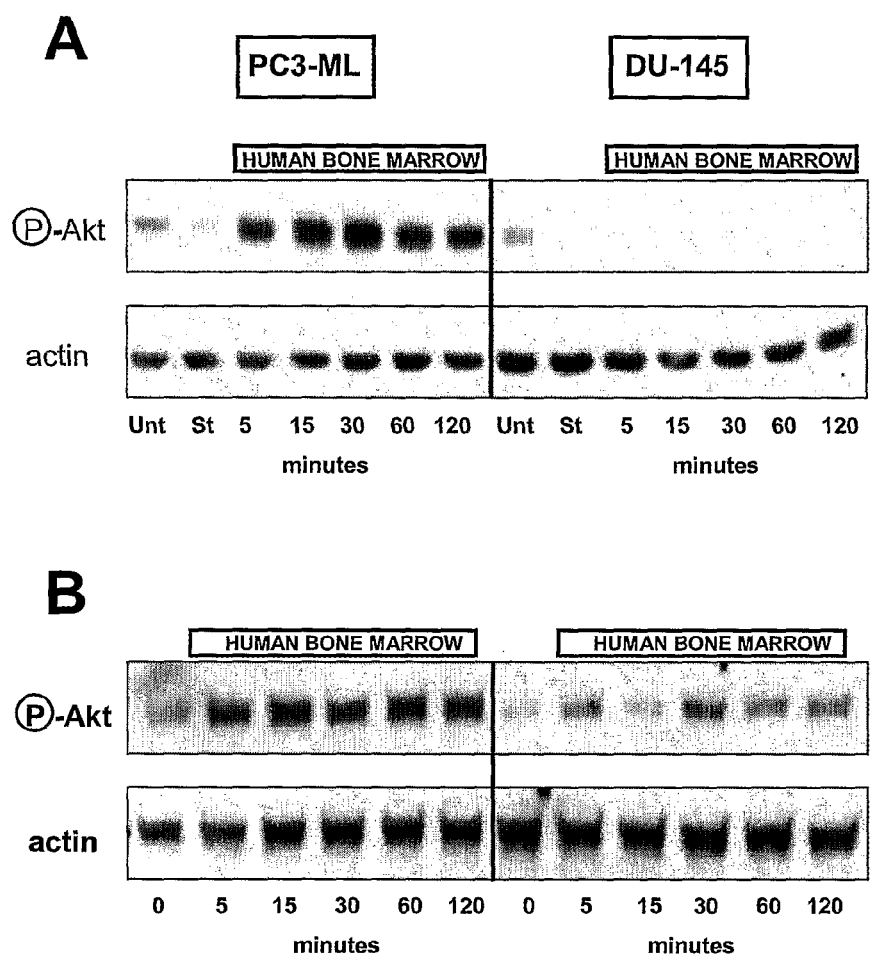
FIG. 10 depicts the effect of human bone marrow aspirate on Akt activity in prostate cancer cells. Cell lysates were subject to SDS-PAGE. For Western blot analysis, membranes were blotted with antibodies targeting phospho-Akt (Ser-473, cell signaling Technology), PDGFRα (R&D Systems) and actin (Sigma). Primary antibody binding was detected using HRP-conjugated protein A or protein G (Sigma).

Bone marrow activation of Akt was detected in PC3-ML cells, which express PDGFRα, but not in DU-145 cells, which lack the receptor. In one experiment, to minimize the effect of serum components on Akt activation, cells were preincubated for 4 hours in serum free media. Addition of bone marrow extracts resulted in robust Akt phosphorylation in PC3-ML cells, but not DU-145 cells. (FIG. 10A). To evaluate the significance of the response, a second experiment was conducted with serum. Robust stimulation of Akt phosphorylation in PC3-ML cells by bone marrow aspirate was also observed in the presence of serum. (FIG. 10B). Only a small response was elicited in DU-145 cells.

PDGFRα-Mediated Akt Phosphorylation.

Figure 11:
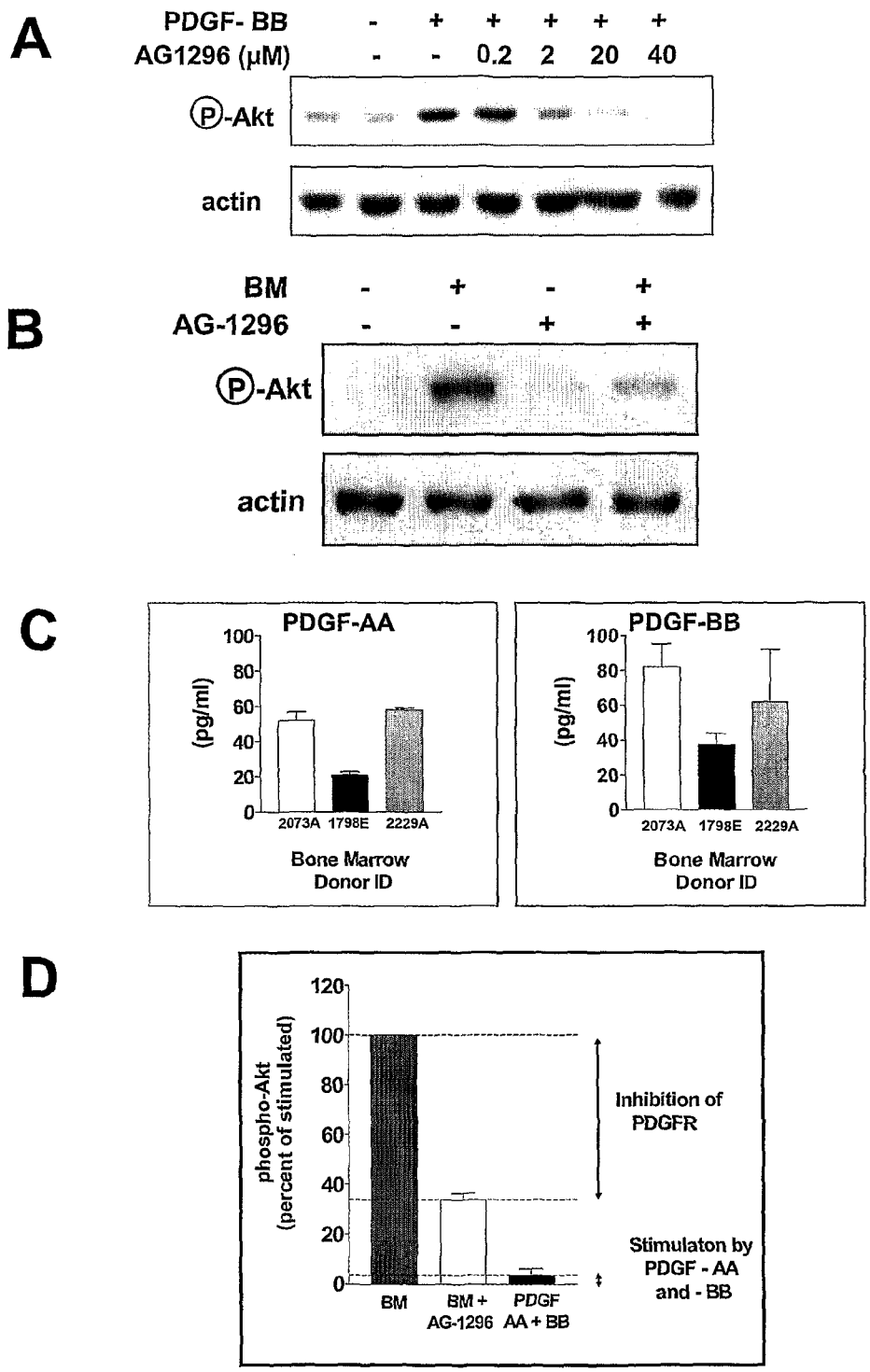
FIG. 11 depicts induction and inhibition of AKT-phosphorylation in PC3-ML cells. Panel A shows the AG-1296 dose dependent inhibition of Akt phosphorylation in cells exposed to 30 ng/ml PDFG-BB. Panel B shows bone aspirate Akt phosphorylation and inhibition by 20 µM AG-1296. Panel C show the potency of bone marrow aspirate to induce Akt phosphorylation as compared to the potency of a combination of 100 pg/ml PDGF-AA and 100 pg/ml PDGF-BB. Panel D compares the magnitudes of bone marrow aspirate induced Akt-phosphorylation, inhibition of bone marrow induced Akt-phosphorylation by AG-1296, and Akt-phosphorylation induced by PDFG-AA+PDFG-BB.

Osteoblasts and osteoclasts, which secrete both PDGF-AA and PDGF-BB, are thought to provide these growth factors in the soluble milieu of bone marrow. To determine whether the responsiveness of PC3-ML cells to bone marrow extracts was related to signal transduction through PDGFRα, PC3-ML cells were exposed to bone marrow aspirate in the absence or presence of 20 µM AG-1296. This concentration of AG-1296 completely inhibits PDGF-BB induced Akt activation. (FIG. 11A) AG-1296 inhibited bone marrow aspirate induced Akt activation by more than 40%. (FIGS. 11B and D). This indicates that PDGFRα signaling is responsible for a significant proportion of bone marrow induced Akt activation.

The direct contribution of PDGF-AA and -BB to PDGFRα signaling relative to other components of bone marrow aspirates was also evaluated. It was determined that the concentrations of PDGF-AA and -BB in bone marrow aspirates from three different donors ranged from 400 pg/ml to 2 ng/ml. Given the 20-fold dilution of the bone marrow aspirates, test cells were actually being exposed to PDGF-AA and -BB concentrations between 20 and 100 pg/ml. Accordingly, PC3-ML cells were treated with 100 pg/ml each of PDGF-AA and -BB. Akt phosphorylation was less than 10% of that obtained with bone marrow aspirates. FIGS. 3C and D). Accordingly, it appears that activation of the Akt pathway by PDGFRα signaling may involve PDGFRα ligands other than PDGF-AA and -BB and/or mechanisms other than activation of PDGFRα by direct binding of a ligand.

Inhibition of Akt Phosphorylation by an Anti-PDGFRα Antibody.

Figure 12:
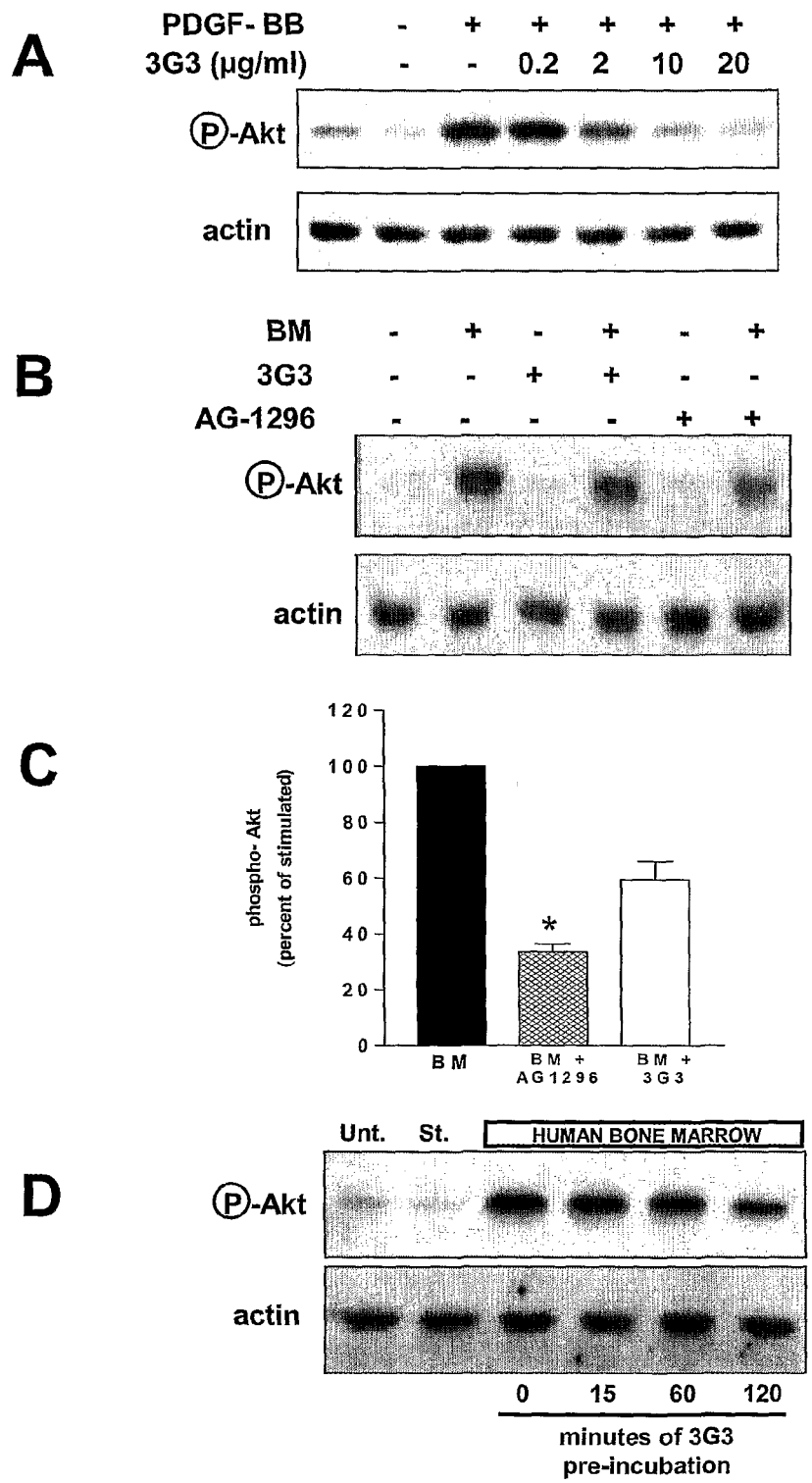
FIG. 12 depicts inhibition of Akt phosphorylation in PC3-ML cells by PDGFRα antagonists. Panel A shows the dose dependent effect of monoclonal antibody IMC-3G3 on Akt phosphorylation induced by 30 ng/ml of PDGF-BB. Panels B and C provide a comparison of the effects of IMC-3G3 and AG1296 on bone marrow induced Akt phosphorylation. Panel D shows that inhibition of Akt phosphorylation is dependent on IMC-3G3 preincubation time.

The neutralizing antibody IMC-3G3, which is specific for human PDGFRα was also tested for its ability to inhibit Akt phosphorylation of in PC3-ML cells. A pre-incubation time of 30 minutes and a concentration of 20 µg/ml neutralized the stimulatory effect of 30 ng/ml of PDGF-BB. (FIG. 12A) Treatment with the antibody also resulted in about 40% inhibition of bone marrow induced Akt phosphorylation (FIGS. 12B and C). It was also observed that the inhibitory effect of IMC-3G3 on Akt phosphorylation was dependent on the duration of the preincubation, with a 120-minute incubation time being significantly more effective (FIG. 12D) than the 30-minute incubation time (FIGS. 12B and C). One possible explanation is that IMC-3G3 induces internalization of PDGFRα, and that its inhibitory effect is related not only to blocking of ligand binding, but also to the removal of the receptor from the plasma membrane.

Example 3

Isolation of Human Anti-PDGFRα Antibodies

Human anti-PDGFRα monoclonal antibodies were generated by a standard hybridoma technology (Harlow & Lane, ed., Antibodies: A Laboratory Manual, Cold Spring Harbor, 211-213 (1998), which is incorporated by reference herein)

using transgenic mice (Medarex Inc., Sunnyvale, Calif.) that express human gamma heavy and kappa light immunoglobulin chains. Human PDGFRα extracellular domain (ECD) was purchased from purchased from R&D Systems (Minneapolis, Minn.). KM mice were immunized subcutaneously (s.c.) with $3 \times 10^7$ porcine aortic endothelial cells stably expressing PDGFRα (PAE Rα). After 4 weeks, mice were boosted s.c. with 50 μg PDGFRα ECD in complete Freund's adjuvant plus $3 \times 10^7$ PAE Rα cells given i.p. Mice were boosted two more times, 3 weeks apart, with 25 μg PDGFRα ECD in incomplete Freund's adjuvant.

Splenocytes from mice with high serum binding and blocking titers were isolated and fused with myeloma cells. Hybridoma cultures displaying blocking activity were subcloned and antibodies from these hybridomas were purified by protein G chromatography.

IgGs were evaluated for binding to PDGFRα in a direct binding assay. PDGFRα ECD in PBS was immobilized onto a 96-well plate (100 ng/well). Plates were then washed with PBST (PBS+0.05% Tween 20) and blocked with PBSM (3% milk in PBS, 200 μL/well) for 2 hours at 25° C. IgGs diluted in PBSM were incubated with the immobilized PDGFRα ECD for 1 hr at 25° C., and the plates were washed with PBST. A secondary antibody (goat F(ab')$_2$ antihuman IgG-horseradish peroxidase conjugate; BioSource International, Camarillo, Calif.) diluted 1:5,000 in PBSM was added for 1 hour at 25° C. After the plates were washed with PBST, a TMB peroxidase substrate (KPL, Gaithersburg, Md.) was added and the reaction was stopped with 100 μL of 1 mol/L $H_2SO_4$. Plates were read at A450 nm using a microplate reader (Molecular Devices, Sunnyvale, Calif.).

PDGF blocking was evaluated using a solid-phase PDGF blocking assay (see Duan et al., 1991, J. Biol. Chem. 266: 413-8, which is incorporated by reference). PDGFRα ECD was diluted in PBS and coated on 96-well microtiter plates (Immulon 2HB flat-bottomed 1×12 Removawell strips of irradiated protein binding polystyrene; Dynex Technologies, Chantilly, Va.). Each well was coated with 60 ng PDGFRα for 3 hours at 25° C. in a total volume of 100 L. Plates were then washed twice and blocked overnight at 4° C. with 25 mmol/L HEPES (pH 7.45), 0.5% gelatin, 100 mmol/L NaCl, and 0.1% Tween 20. Plates were then warmed to 25° C. for 20 minutes and washed once with binding buffer (25 mmol/L HEPES (pH 7.45), 0.3% gelatin, 100 mmol/L NaCl, 0.01% Tween 20). Fifty microliters of IgGs were added to each well and incubated at 25° C. for 30 minutes. Iodinated PDGF was diluted in binding buffer and added (50 μL of a 1 nmol/L solution) to each well. Plates were incubated for 2 hours at 25° C. and then washed five times with binding buffer. Each well was counted in a gamma counter. A cell-based blocking assay was done as described in Heldin et al., 1988, EMBO J. 7, 1387-93.

The kinetics of antibody binding to PDGFRα was measured using a BIAcore 3000 instrument (BIAcore, Inc., Piscataway, N.J.). PDGFRα ECD was immobilized onto a sensor chip and antibody was injected at various concentrations. Sensograms were obtained at each concentration and evaluated using the BIA Evaluation 2.0 program to determine the rate constants. The affinity constant, $K_d$, was calculated from the ratio of rate constants $K_{off}/K_{on}$.

Figure 13:
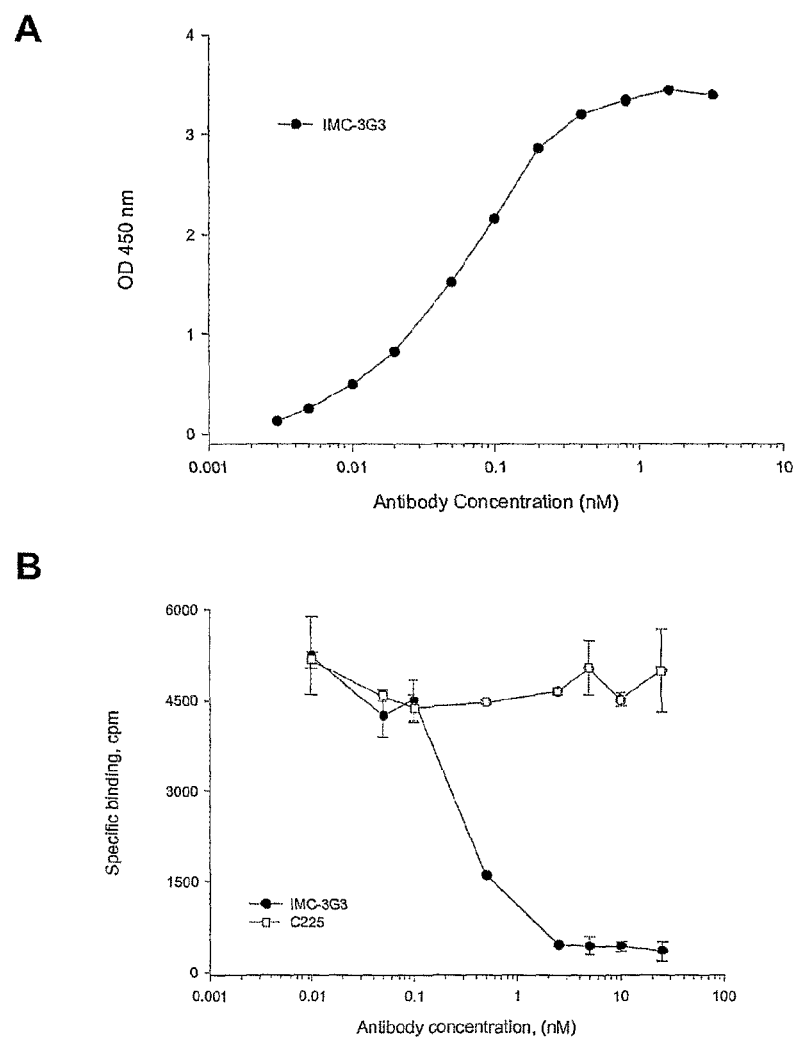
FIG. 13 shows binding of antibody to PDGFRα. A: direct binding of anti-PDGFRα antibody to the immobilized extracellular domain of PDGFRα. B: inhibition of [$^{125}$I]PDGF-AA binding to immobilized PDGFRα.

FIG. 13 shows dose-dependent binding of the human monoclonal antibody IMC-3G3 to immobilized PDGFRα ECD in the ELISA. The antibody concentration required for 50% maximum binding to PDGFRα ECD was 0.06 nmol/L (Table 6). The $ED_{50}$ is consistent with the Kd for the antibody as determined by surface plasmon resonance on a BIAcore instrument (Table 1). The monoclonal antibody also blocked [$^{125}$I]PDGF-BB binding to immobilized receptor, with an $IC_{50}$ of 0.43 nmol/L. The binding sites for PDGF-AA and PDGF-BB on PDGFRα are not structurally coincident. The data suggests that the epitope for 3G3 spatially overlaps both growth factor binding sites.

TABLE 6

Binding characteristics of anti-PDGFRα antibody

| PDGFRα binding | PDGF blocking | | Binding kinetics | | |
|---|---|---|---|---|---|
| $ED_{50}$, nmol/L | Solid phase $IC_{50}$, nmol/L | Cell based $IC_{50}$, nmol/L | $K_{on}$ ($10^5$ mol/ $L^{-1}s^{-1}$) | $K_{off}$ ($10^{-4}s^{-1}$) | $K_d$ ($10^{-9}$ mol/L) |
| 0.06 | 0.24 | 0.58 | 11.50 | 0.47 | 0.04 |

Inhibition of Receptor Phosphorylation and Activation of Downstream Effector Molecules.

The effects on PDGF-induced intracellular signaling by IMC-3G3 was determined using PAE Rα cells. Cells were seeded in six-well Falcon tissue culture plates (250,000 cells per well) and allowed to grow overnight. Wells were then rinsed and incubated in serum-free medium. After an overnight incubation to render cells quiescent, the cells were treated with antibodies for 30 minutes at 37° C. followed by addition of PDGF-AA or PDGF-BB and incubation for an additional 10 minutes at 37° C. Cells were then detached and lysed in 200 μL lysis buffer (50 mmol/L Tris-HCl (pH 8.0), 1% Triton X-100, 150 mmol/L NaCl, 1 mmol/L EDTA, 0.1% SDS, 1 mmol/L sodium orthovanadate, and protease inhibitors (Complete Mini, Roche, Mannheim, Germany)). Cell lysates were analyzed by SDS-PAGE and Western blotting using enhanced chemiluminescence reagents and Hyperfilm (Amersham Biosciences).

Figure 14:
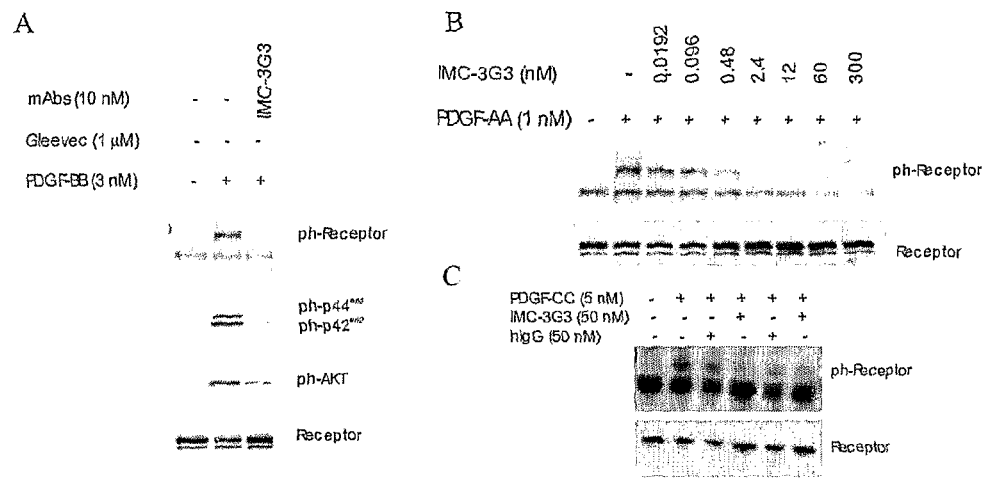
FIG. 14 shows specific inhibition of phosphorylation of PDGFRα and downstream effector molecules.

The antibody was tested for the ability to inhibit ligand-induced receptor tyrosine phosphorylation. PDGF-AA and PDGF-BB increase PDGFRα tyrosine phosphorylation about 5-fold at 1 and 3 nmol/L concentrations, respectively. Higher concentrations of ligand (10 nmol/L) resulted in less phosphorylated receptor possibly due to ligand-induced degradation. The antibody inhibited PDGF-BB-induced receptor to near background levels (FIG. 14A, top row). Similar data were obtained using PDGF-AA to induce receptor phosphorylation.

PDGFs transduce mitogenic signals and exert antiapoptotic effects on receptor-expressing cells through downstream effector protein. Accordingly, the monoclonal antibody was tested for its ability to inhibit activation of MAPKs p44/p42 and Akt (involved in cell growth and antiapoptotic pathways, respectively). The anti-PDGFRα antibody inhibited phosphorylation of both MAPKs and Akt in response to PDGF-BB (FIG. 2A) and PDGF-AA (not shown). Inhibition of PDGFRα phosphorylation was dose dependent, with 50% inhibition achieved at 0.25 nmol/L (FIG. 14B).

Antimitogenic Activity.

The ant-PDGFRα monoclonal antibody was tested for its ability to block PDGFAA-induced mitogenesis of PAE Rα cells. Cells were seeded in 96-well tissue culture plates ($1 \times 10^4$ cells per well) and grown overnight in 100 μL medium per well. The wells were then rinsed with serum-free medium and cells were serum starved overnight with 75 μL serum-free medium added to each well. IgG was added (25 μL/well) and the plates were incubated for 30 minutes at 37° C. PDGF-AA or PDGF-BB (25 μL/well) was then added and plates were incubated for 18 to 20 hours at 37° C. Plates were incubated for an additional 4 hours after each well received 0.25 μCi

[³H]thymidine (25 μL/well). Antibody, PDGF, and [³H]thymidine were all diluted in serum-free medium. Cells were then washed with PBS plus 1% bovine serum albumin and detached by treatment with trypsin (100 μL/well). The cells were collected onto a filter and washed thrice with double-distilled water using a MACH III cell harvester (Tomtec, Inc., Hamden, Conn.). After processing the filter, DNA incorporated radioactivity was determined on a scintillation counter (Wallac Microbeta, model 1450).

Figure 15:
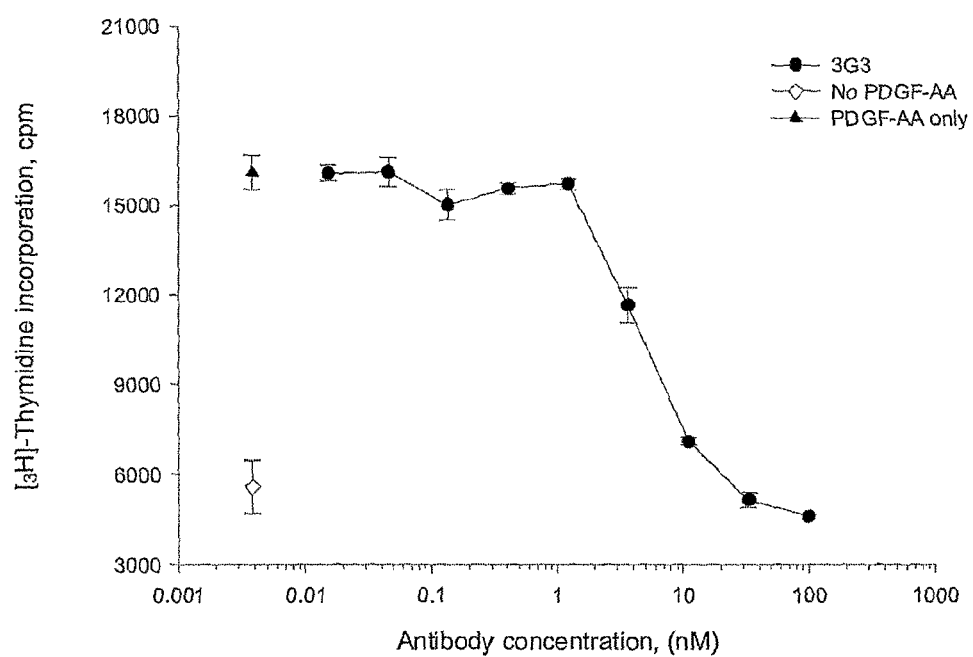
FIG. 15 shows inhibition of PDGF-AA-stimulated [$^3$H] thymidine incorporation in PAE Rα cells by mAbs.

When IMC-3G3 was added to serum-starved PAE Rα cells, PDGF-AA induced thymidine incorporation was specifically inhibited (FIG. 15) with an $EC_{50}$ of 8.3 nmol/L. The antibody also inhibited the 3 nmol/L PDGF-BB-induced mitogenesis of PAE Rα cells with an $EC_{50}$ of 1.25 nmol/L (data not shown).

Growth Inhibition of Human Tumor Cell Lines Expressing PDGFRα.

Human tumor cell lines expressing PDGFRα were tested to determine the affects of the human anti-PDGFRα antibody on malignant growth in in vitro and in vivo systems. Two such tumor cell lines that express PDGFRα as determined by flow cytometry are SKLMS-1 (leiomyosarcoma) and U118 (glioblastoma). These cell lines also respond to ligand in mitogenic assays and form tumors in mice. SKLMS-1 has the potential for not only paracrine but also autocrine stimulation. SKLMS-1 was shown to express PDGF-AA protein when grown in culture using a quantitative sandwich enzyme immunoassay technique (R&D Systems).

Figure 16:
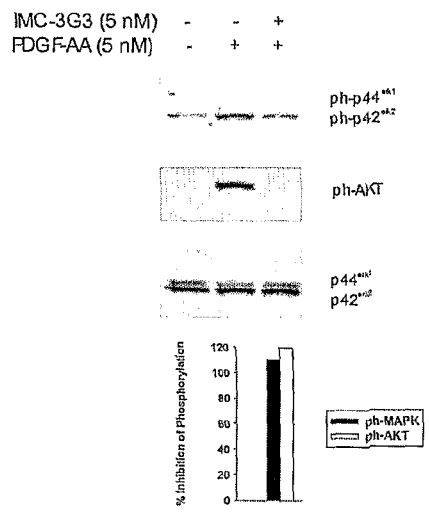
FIG. 16 shows inhibition of PDGF-AA-induced downstream-effector molecule activation in SKLMS-1 (A) and U118 (B) cells.
Figure 16:
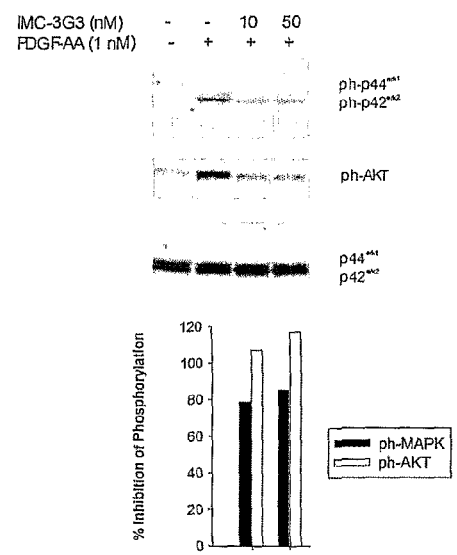
Figure 17:
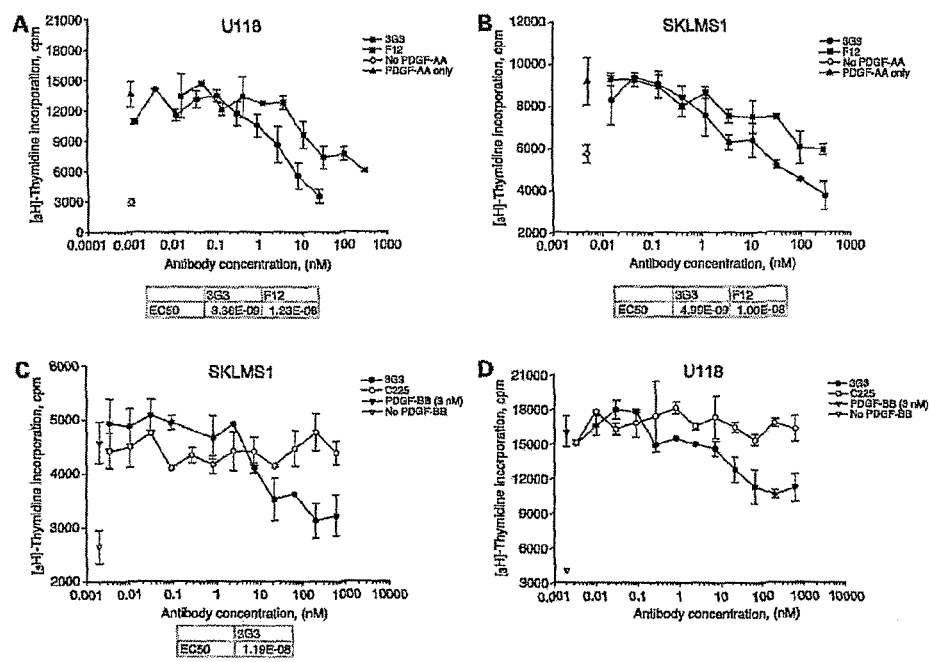
FIG. 17 shows inhibition of PDGF-AA-stimulated [$^3$H] thymidine incorporation in U118 (A) and SKLMS-1 (B) cells by mAbs. Inhibition of PDGF-BB-stimulated [$^3$H]thymidine incorporation is also shown for SKLMS-1 (C) and U118 (D) cells.

As can be seen in FIG. 16A, IMC-3G3 inhibited the phosphorylation of both Akt and MAPKs in response to PDGF-AA stimulation of SKLMS-1 cells. The inhibition of Akt phosphorylation was 100% and that of MAPKs was about 80%. The antibody is also an effective inhibitor of phosphorylation in U118 cells (FIG. 16B). Ligand-induced mitogenesis of tumor cells was also blocked. When the anti-PDGFRα antibody was added to serum-starved U118 cells, PDGF-AA-induced thymidine incorporation was specifically inhibited (FIG. 17A) with an $EC_{50}$ of 3.4 nmol/L. The antibody also inhibited the PDGF-AA-induced mitogenic response of SKLMS-1 cells with an $EC_{50}$ of 5 nmol/L (FIG. 17B), as well as the PDGF-BB-stimulated mitogenic response (FIG. 17C). Only partial inhibition (40% at 66 nmol/L; FIG. 17D) of the PDGF-BB-stimulated mitogenic response was observed for U118 cells. This is attributed to the expression of both PDGFRα and PDGFRβ in those cells (data not shown).

Inhibition of Tumor Xenograft Growth.

IMC-3G3 was tested in vivo in glioblastoma (U118) and leiomyosarcoma (SKLMS-1) subcutaneous (s.c.) xenograft models in athymic nude mice. S.c. tumor xenografts were established by injecting 10×10⁶ SKLMS-1 or U118 cells mixed in Matrigel (Collaborative Research Biochemicals, Bedford, Mass.) into female athymic nude mice (Crl:NU/NU-nuBR, Charles River Laboratories, Wilmington, Mass.). Tumors were allowed to reach a mean tumor volume (π/6× longest length×perpendicular width²) of about 400 mm³. The mice were randomized into five groups (n=12) and treated by i.p. injection twice weekly for the duration of the study. Group 1 mice were treated with vehicle control (0.9% NaCl, USP for Irrigation, B/Braun). Groups 2 to 4 mice were treated with 6, 20, and 60 mg/kg of the instant anti-PDGFRα antibody. Group 5 mice were treated with 60 mg/kg human IgG (Sigma). Groups treated with 6, 20, or 60 mg/kg anti-PDGFRα antibody or human IgG were given 21.4, 71.4, and 214 mg/kg loading doses, respectively. The loading doses were calculated to achieve a steady state plasma concentration from the first dose (elimination half-life, 7 days) using a dosing regimen of twice weekly. Tumor volumes were evaluated twice weekly and tumor growth in the treatment groups was compared with a repeated measures ANOVA.

Figure 18:
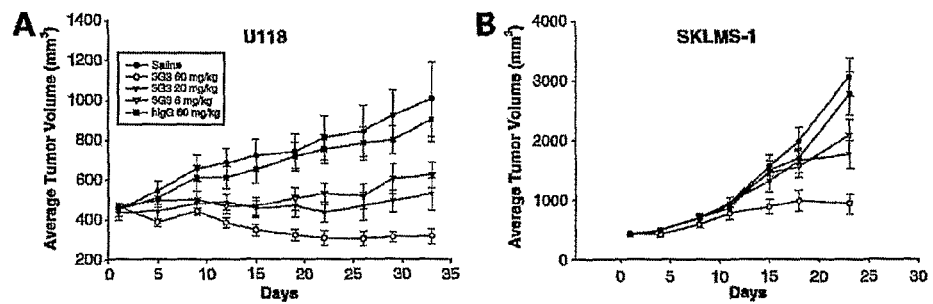
FIG. 18 shows dose dependent effects for treatment of established U118 (glioblastoma; panel A) and SKLMS-1 (leiomyosarcoma; panel B) tumor xenografts in nude mice.

As shown in FIG. 18A, human IgG had no effect on glioblastoma growth compared with saline treated mice (P=0.74), whereas the anti-PDGFRα antibody significantly inhibited tumor growth at 6 (P=0.06), 20 (P=0.03), and 60 (P=0.0004) mg/kg doses. At the end of the U118 study, the % T/C [(average tumor volume for the 3G3-treated group at conclusion of study/average tumor volume at beginning of treatment)/(average tumor volume for control-treated group at conclusion of study/average tumor volume at beginning of treatment)× 100] values were 67%, 63%, and 35% for 6, 20, and 60 mg/kg 3G3-treated dose groups, respectively. Further, tumor regression was observed in 4 of 12, 5 of 11, and 10 of 12 animals in the 6, 20, and 60 mg/kg treatment groups. There were no regressions in either control group.

FIG. 18B shows that leiomyosarcoma growth was also significantly inhibited by treatment at 6 (P=0.02), 20 (P=0.003), and 60 (P<0.0001) mg/kg. The final % TIC values were 66%, 57%, and 31% for the 6, 20, and 60 mg/kg treatment groups, respectively with no tumor regressions.

Histologic examination of xenografts at the end of treatment showed marked differences in tumors from treated animals as compared with tumors from animals receiving control therapy. Resected tumors were fixed in QDL fixative at 4° C. for 24 hours. After paraffin embedding and sectioning at 4 μm, formalin-fixed sections were stained with Mayer's H&E (Richard Allen, Kalamazoo, Mich.).

In the U118 group treated with the highest dose (60 mg/kg), fewer viable tumor cells were found and there were substantially more cell-sparse regions compared with the saline-control group (FIG. 18C). Treated SKLMS-1 xenografts at day 25 also showed a reduction in the amount of viable tumor cells and cellular packing compared with the saline-control group (FIG. 18D).

In Vitro Inhibition of PDGFRα-Mediated Stimulation of a Glioblastoma Line.

Figure 19:
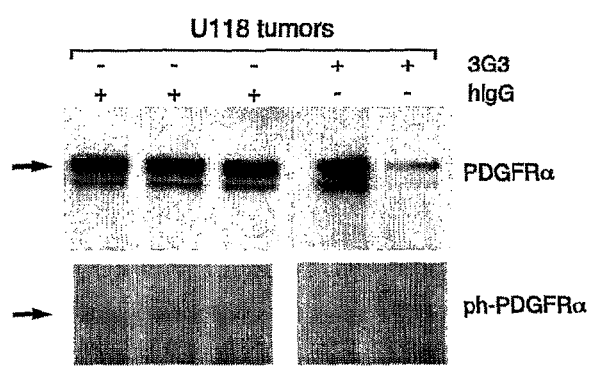
FIG. 19 shows reduction of PDGFRα phosphorylation in vivo in U118 tumors treated with anti-PDGFRα antibody, as compared to treatment with nonspecific human IgG.

The level of receptor phosphotyrosine in U118 tumors was evaluated one week after treatment with anti-PDGFRα antibody or human IgGt. Mice with established U118 tumors (500 mm³) were treated with a 214 mg/kg loading dose followed 72 hours later by a 60 mg/kg maintenance dose of antibody. Tumors were harvested from mice one week (168 hours) after the first antibody injection (at a time before tumor regression is observed on average; see FIG. 18A) and homogenized in phosphorylation assay lysis buffer (see above). The lysates were centrifuged twice at 14,000 rpm and the protein concentration for the collected supernatant was determined (Bio-Rad protein assay, Bio-Rad, Hercules, Calif.). Lysate (4 mg) from each sample was immunoprecipitation using anti-PDGFRα antibody. Immunoprecipitated human PDGFRα was then immunoblotted with either an anti-PDGFR or anti-phosphotyrosine antibody. FIG. 19 shows that administration of anti-PDGFRα antibody resulted in reduction in the level of PDGFRα phosphotyrosine relative to a human IgG control in these tumors.

Cell Line Engineering.

First, the genes encoding the heavy and light chain variable domains of the human anti-PDGFRα antibody were cloned and sequenced. A primer series was obtained from MEDAREX that anneals to the 5' and 3' flanking sequences of the human immunoglobulin variable region sequences within MEDAREX-derived hybridomas. The heavy chain variable region amplified with primer pair AB88 (forward) and AB90 (reverse) (Table 7). Light chain products were amplified with primer pairs containing the forward primer AB182 and reverse primer AB16 (Table 7). The 0.4 kb products of these reactions were cloned into the vector ZeroBlunt (Invitrogen) to produce AB88-1 ($V_H$) and AB 182-3 (Vκ), and the inserts were sequenced with universal T7 and M13R primers.

TABLE 7

Primers for MEDAREX hybridomas

| Oligo | Size | DNA sequence (5'-3') | SEQ ID NO |
|---|---|---|---|
| AB88 | 21 | ATGAAACACCTGTGGTTCTTC | 20 |
| AB90 | 21 | TGCCAGGGGGAAGACCGATGG | 21 |
| AB182 | 24 | ATGGAA(G/A)CCCCAGCGCAGCTTCTC | 22 |
| AB16 | 20 | CGGGAAGATGAAGACAGATG | 23 |

In order to generate plasmid vectors for expressing the complete IgG1 antibody, the cloned variable regions were PCR amplified and ligated in two steps into expression vectors containing constant region genes. Primary PCR heavy chain amplification utilized 25 ng of plasmid AB88-1 as template for primers IPHF5 (forward) and IPHR5 (reverse). Secondary PCR heavy chain amplification utilized 5 µl primary reaction as template and the primers OPSIF and IPHR5. The combination of the two forward primers add a 57 base pair sequence to the 5' end of the immunoglobulin genes encoding a 19 amino acid mouse heavy chain gene signal sequence (MGWSCIILFLVATATGVHS; SEQ ID NO:24) for efficient immunoglobulin processing and secretion. In addition, the forward primer OPSIF adds a consensus "Kozak" sequence (*J. Mol. Biol.* 196:947) for efficient initiation of translation of these genes in mammalian cells and a 5' HindIII restriction endonuclease site for cloning of the amplified product into the suitable expression vector. The heavy chain reverse primer contains an inframe NheI site for cloning into the constant region vector.

PCR was performed in two steps utilizing the Expand PCR kit (Boehringer Mannheim Inc.) according to manufacturer's specifications using Expand Buffer system #3 in 50 µl reactions with the following cycling conditions:

| | |
|---|---|
| 1 cycle | 94°, 2 minutes |
| 5 cycles | 94°, 20 seconds |
| | 48°, 60 seconds |
| | 68°, 2 minutes |
| 20 cycles | 94°, 20 seconds |
| | 65°, 60 seconds |
| | 68°, 2 minutes |
| 1 cycle | 68°, 5 minutes |

After two rounds of PCR, the product was purified following agarose gel electrophoresis and cloned as a HindIII-NheI digested fragment into vector pDFc (FIG. 8), which contains the human gamma 1 constant region.

Primary PCR light chain amplification utilized 25 ng of pAB182-3 plasmid as template primers IPLF4 (forward) and IPLR2 (reverse). Secondary PCR light chain amplification utilized 5 µl primary reaction as template and the primers OPSIF and IPLR2, As for the heavy chain, the two forward primers provide a secretion signal sequence. The light chain reverse primer contains an in-frame BsiWI site for cloning into the kappa constant region vector pLck (FIG. 8). PCR reactions were performed as for the heavy chain above. After two rounds of PCR, the product was purified following agarose gel electrophoresis and cloned into pLck, which contains the human kappa light chain constant region.

TABLE 8

Primers for $V_H$ and Vκ expression vectors

| Oligo | Size | DNA sequence (5'-3') | SEQ ID NO |
|---|---|---|---|
| OPSIF | 53 | GAGAAGCTTGCCGCCACCATGGGATGG TCATGTATCATCCTTTTTCTAGTAGC | 25 |
| IPHF5 | 58 | TCCTTTTTCTAGTAGCAACTGCAACTGGA GTACATTCACAGCTGCAGCTGCAGGAGTC | 26 |
| IPHR5 | 37 | CGCGCTAGCTGAGGAGACG GTGACCAGGGTTCCCTGG | 27 |
| IPLF4 | 58 | TCCTTTTTCTAGTAGCAACTGCAACTGGA GTACATTCAGAAATTGTGTTGACACAGTC | 28 |
| IPLR2 | 37 | GCGCGTACGTTTGATTTCCACCTTGGTCC CTTGGCCG | 29 |

Figure 20:
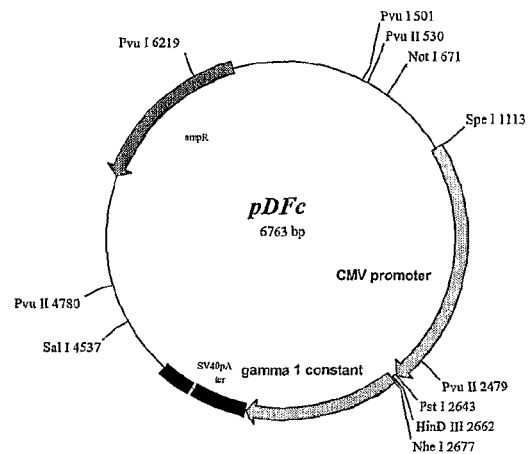
FIG. 20 depicts the GS expression vectors used for cloning hybridoma derived human VH and Vκ variable regions genes and expression of complete human heavy (IgG1) and light chain proteins. The two vectors were recombined as explained in the Examples and the combined vector was transfected into NS0 cells.
Figure 20:
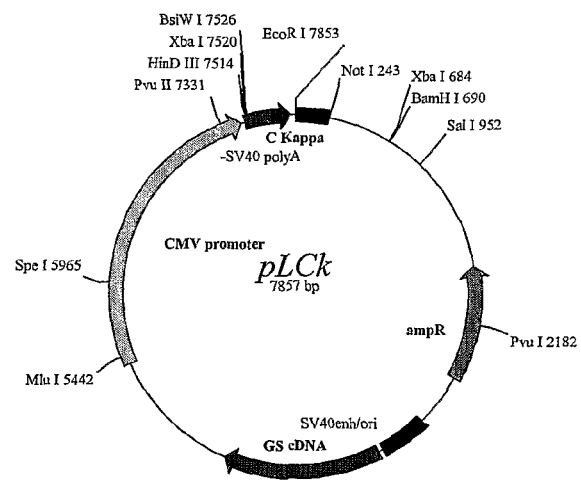

In order to generate a single plasmid vector for stable transfection, the heavy chain expression cassette, containing the CMV promoter, heavy chain coding region, and polyA element were cloned into the light chain vector as a NotI-SalI fragment (FIG. 20).

This construct was then utilized to generate a stable production line in myeloma cell line NS0 cells. NS0 cells were transfected with the expression plasmid via electroporation using the BioRad Gene Pulser II. Prior to transfection, the plasmid DNA was linearized with PvuI, ethanol precipitated, and resuspended at a concentration of 0.4 mg/ml (40 ug in 100 ul M90). Cells were electroporated with the 40 ug of DNA in a final volume of 800 ul by a single pulse of 250 volts, 400 µFd. Electroporated cells were dispersed in 50 ul aliquots in DMEM medium (JRH Biosciences Inc.) containing 10% dialysed fetal calf serum (dFCS) (Hyclone, Lot#: AHA7675) and 2 mM glutamine (Invitrogen/Life Technologies) into wells of approximately eighteen 96 well plates at a density of 5,000-10,000 cells per well. Selection for glutamine synthetase (GS) positive transfectants was initiated 24 hours later by the addition of glutamine free DMEM containing 10% dFCS and supplemented with 1×GS supplement (JRH Biosciences Inc.). Cells were cultured for 2-4 weeks at 37° C., 5% $CO_2$ to enable the growth and expansion of colonies. More than 300 colonies were screened using an anti-human Fc (gamma) ELISA (Horseradish peroxidase detection at A450 nm). Antibody expressing clones (58%) were expanded and retested for productivity over 3-5 days cultivation. To adapt cells into serum free medium, positive cell lines were expanded by the addition of an equal volume of serum free GS-OS cultivation medium at each passage. Strong positives, producing 25 ug/ml or more in 3 day sub-confluent 24 well cultures, were expanded for further analysis to complete adaptation to serum free medium.

It is understood and expected that variations in the principles of invention herein disclosed may be made by one skilled in the art and it is intended that such modifications are to be included within the scope of the present invention.

What is claimed is:

1. A method of inhibiting growth of a primary tumor or a metastatic tumor in a patient in need thereof by administering to the patient an effective amount of an antibody or an antibody fragment thereof specific for human PDGFR alpha and comprising SSSYY (SEQ ID NO:2) at CDRH1; SFFYTGSTYYNPSLRS (SEQ ID NO:4) at CDRH2; QSTYYYGSGNYYGWFDR (SEQ ID NO:6) at CDRH3; RASQSVSSYLA (SEQ ID NO:10) at CDRL1; DASNRAT (SEQ ID NO:12) at CDRL2; and QQRSNWPPA (SEQ ID NO:14) at CDRL3, wherein the tumor is selected from the group consisting of a leiomyosarcoma and a glioblastoma.

2. A method of inhibiting growth of a primary tumor or a metastatic tumor in a patient in need thereof by administering to the patient an effective amount of an antibody or an antibody fragment thereof specific for human PDGFR alpha and comprising a heavy chain variable region having the amino acid sequence:

(SEQ ID NO: 8)
QLQLQESGPGLVKPSETLSLTCTVSGGSINSSSYYWGWLRQSPGKGLEW

IGSFFYTGSTYYNPSLRSRLTISVDTSKNQFSLMLSSVTAADTAVYYCA

RQSTYYYGSGNYYGWFDRWDQGTLVTVSS and a light chain variable region having the amino acid sequence:

(SEQ ID NO: 16)
EIVLTQSPATLSLSPGERATLSCRASQSVSSYLAWYQQKPGQAPRLLIY

DASNRATGIPARFSGSGSGTDFTLTISSLEPEDFAVYYCQQRSNWPPAF

GQGTKVEIK, wherein the tumor is selected from the group consisting of a leiomyosarcoma, and a glioblastoma.

3. The method of claim 2, wherein the antibody comprises a heavy chain of SEQ ID NO:31, and a light chain of SEQ ID NO:33.

* * * * *